United States Patent [19]
Turner et al.

[11] Patent Number: 6,010,885
[45] Date of Patent: *Jan. 4, 2000

[54] EXPRESSION OF HETEROLOGOUS POLYPEPTIDES IN HALOBACTERIA

[75] Inventors: George J. Turner; Mary C. Betlach, both of San Francisco, Calif.

[73] Assignee: The Regents of the University of California, Oakland, Calif.

[*] Notice: This patent issued on a continued prosecution application filed under 37 CFR 1.53(d), and is subject to the twenty year patent term provisions of 35 U.S.C. 154(a)(2).

This patent is subject to a terminal disclaimer.

[21] Appl. No.: 08/767,993

[22] Filed: Dec. 13, 1996

Related U.S. Application Data

[63] Continuation of application No. 08/313,553, Sep. 27, 1994, Pat. No. 5,641,650, which is a continuation of application No. 08/038,662, Mar. 25, 1993, abandoned.

[51] Int. Cl.[7] .............................. C12N 1/21; C12N 15/74; C12P 21/00; C12P 21/02
[52] U.S. Cl. .................... 435/69.7; 435/69.1; 435/252.3; 435/320.1; 435/471; 435/476
[58] Field of Search ................................ 435/69.1, 172.3, 435/252.3, 69.7, 320.1, 471, 476

[56] References Cited

FOREIGN PATENT DOCUMENTS 59-036700  2/1984  Japan .
3151883  6/1991  Japan .

OTHER PUBLICATIONS

Blaseio et al., Proc. Natl. Acad. Sci. USA 87:6772–6776 (1990).
Holmes et al., "A Plasmid Vector with a Selectable Marker for *Halophilic Archaebacteria*," *Journal of Bacteriology,* 172:756–761 (1990).
Ni et al., "An Efficient System for the Synthesis of bacteriorhodopsin in *Halobacterium halobium*," *Gene,* 90:169–172 (1990).
Birge, "Photophysics and Molecular Electronic Applications of the Rhodopsins," *Annu. Rev. Phys. Chem.,* 41:683–733 (1990).
Betlach et al., "Characterization of a halobacterial Gene Affecting Bacterioopsin Gene Expression," *Nucleic Acids Research,* 12:7949–7959 (1984).
Dunn et al., "The Bacteriorhodopsin Gene," *PNAS USA,* 78:6744–6748 (1981).
Dunn et al., "Structure–Function Studies on Bacteriorhdopsin," *J. Biol. Chem.,* 262(19):9246–9254 (1987).
Krebs et al., "Expression of the Bacterioopsin gene in *Halobacterium halobium* Using a Multicopy Plasmid," *PNAS USA,* 88:859–863 (1991).
Derwent Abstract of Japanese Patent 3151883 (Jun. 28, 1991).
Derwent Abstract of Japanese Patent 59036700 (Feb. 28, 1984).
The Patent Office Japanese Government "Patent Abstracts of Japan," 8(126):228 (1984).

*Primary Examiner*—Johnny F. Railey, II
*Attorney, Agent, or Firm*—Flehr Hohbach Test Albritton & Herbert LLP; Robin M. Silva

[57] ABSTRACT

This invention relates to the preparation and use of expression systems capable of producing heterologous polypeptides in halobacterial hosts.

10 Claims, 50 Drawing Sheets

```
ATCTGCAGGA TGGGTGCAAC CGTGAAGTCC GTCACGGCTG CGTCACGACA GGAGCCGACC         60

AGCGACACCC AGAAGGTGCG AACGGTTGAG TGCCGCAACG ATCACGAGTT TTTCGTGCGC        120

TTCGAGTGGT AACACCCGTG CACGCCATCG CTTCACCGCG GGTGTTTCGA CGCCAGCCGG        180

CCGTTGAACC AGCAGGCCAGC GGCCATTTCA CAGCCCGCTGT GGCCCACACA CTCGGTGGGG     240

TGGCTATTT TGGTATGGTT TGGAATCCGC CGTGTCGGCTC CGTGTCTGAC GGTTCATCGG       300

TCTAAATTCC GTCACGAGCC TACCATACTG AGAGTTACAC ACATATCCTC                   360

GTTAGGTACT GTTGC ATG TTG GAG TTA TTG CCA ACA GCA GTG GAG GGG GTA        411
              Met Leu Glu Leu Leu Pro Thr Ala Val Glu Gly Val
                1                 5                        10

TCG CAG GCC CAG ATC ACC GGA CGT CCG GAG TGG CTA GCG CTC                  459
Ser Gln Ala Gln Ile Thr Gly Arg Pro Glu Trp Ile Trp Leu Ala Leu
              15                      20                  25

GGT ACG GCG CTA ATG GGA CTC GGG ACG CTC TAT TTC CTC GTG AAA GGG         507
Gly Thr Ala Leu Met Gly Leu Gly Thr Leu Tyr Phe Leu Val Lys Gly
             30                       35                  40
```

FIG. 2(A)

```
ATG GGC GTC TCG GAC CCA GAT GCA AAG AAA TTC TAC GCC ATC ACG ACG        555
Met Gly Val Ser Asp Pro Asp Ala Lys Lys Phe Tyr Ala Ile Thr Thr
 45                      50                      55                  60

CTC GTC CCA GCC ATC GCG TTC ACG ATG TAC CTC TCG ATG CTG CTG GGG        603
Leu Val Pro Ala Ile Ala Phe Thr Met Tyr Leu Ser Met Leu Leu Gly
                 65                      70                      75

TAT GGC CTC ACA ATG GTA CCG TTC GGT GGG GAG CAG AAC CCC ATC TAC        651
Tyr Gly Leu Thr Met Val Pro Phe Gly Gly Glu Gln Asn Pro Ile Tyr
                 80                      85                      90

TGG GCG CGG TAC GCT GAC TGG CTG TTC ACC ACG CCG CTG TTG TTG TTA        699
Trp Ala Arg Tyr Ala Asp Trp Leu Phe Thr Thr Pro Leu Leu Leu Leu
                 95                     100                     105

GAC CTC GCG TTG GAC GTT GAC GCG GAT CAG GGA ACG ATC CTT GCG CTC        747
Asp Leu Ala Leu Val Asp Ala Asp Gln Gly Thr Ile Leu Ala Leu
         110                     115                     120

GTC GGT GCC GAC GGC ATC ATG ATC GGG ACC GGC CTG GTC GGC GCA CTG        795
Val Gly Ala Asp Gly Ile Met Ile Gly Thr Gly Leu Val Gly Ala Leu
         125                     130                     135                 140
```

FIG. 2(B)

```
ACG AAG GTC TAC TCG TAC CGC TTC GTG TGG GCG ATC AGC ACC GCA    843
Thr Lys Val Tyr Ser Tyr Arg Phe Val Trp Ala Ile Ser Thr Ala
        145                 150                 155

GCG ATG CTG TAC ATC CTG TAC GTG CTG TTC TTC GGG TTC ACC TCG AAG    891
Ala Met Leu Tyr Ile Leu Tyr Val Leu Phe Phe Gly Phe Thr Ser Lys
        160                 165                 170

GCC GAA AGC ATG CGC CCC GAG GTC GCA TCC ACG TTC AAA GTA CTG CGT    939
Ala Glu Ser Met Arg Pro Glu Val Ala Ser Thr Phe Lys Val Leu Arg
        175                 180                 185

AAC GTT ACC GTT GTG GTG TTG TGG TCC GCG TAT CCC GTC GTG CTG ATC    987
Asn Val Thr Val Val Leu Trp Ser Ala Tyr Pro Val Val Trp Leu Ile
        190                 195                 200

GGC AGC GAA GGT GCC GGA ATC GTG CCG CTG AAC ATC GAG ACG CTG CTG   1035
Gly Ser Glu Gly Ala Gly Ile Val Pro Leu Asn Ile Glu Thr Leu Leu
        205                 210                 215                 220

TTC ATG GTG CTT GAC GTG AGC GCG AAG GTC GGC TTC GGG CTC ATC CTC   1083
Phe Met Val Leu Asp Val Ser Ala Lys Val Gly Phe Gly Leu Ile Leu
        225                 230                 235
```

FIG. 2(C)

```
CTG CGC AGT CGT GCG ATC TTC GGC GAA GCC CCG GAG CCG TCC    1131
Leu Arg Ser Arg Ala Ile Phe Gly Glu Ala Pro Glu Pro Ser
            240                 245                 250

GCC GGC GAC GGC GGC GCC GCG ACC AGC GAC TGATCGGCACA CGCAGGACAG    1181
Ala Gly Asp Gly Gly Ala Ala Thr Ser Asp
        255                 260

CCCCACAACC GGGCGGGCTG TGTTCAACGA CACACGATGA GTCCCCCACT CGGTCTTGTA    1241

CTCGGATCCT TTT    1254
```

FIG. 2(D)

POLYLINKER 1 : 12.3/HindIII.SphI.MluI.XhoI.PstI.SalI.XbaI.BamHI.HindIII.XbaI.KpnI.
POLYLINKER 2 : 3.7/SphI.EcoR5.SstI.SmaI.EcoRI.

CYTOPLASMIC SIDE

ARG PRO GLU VAL ALA SER THR PHE
MET SER GLU ALA
PRO GLU PRO ALA GLU ALA GLU GLY
SER SER THR ALA ILE PHE
ALA GLY ASP GLY ALA ALA ARG SER ARG ALA

LYS THR PHE PHE
SER GLY PHE LEU TYR
VAL LEU LEU TYR
ILE LEU MET ALA ILE
MET ALA THR ALA
SER ALA
TRP VAL
TRP PHE
ARG

LYS ARG
VAL ASN
LEU VAL VAL TRP
THR VAL SER PRO
LEU ALA VAL TRP
TYR VAL LEU
VAL ILE SER
GLY GLU ALA
GLY GLY ILE
VAL

LEU LEU
ILE GLY
LEU PHE 216
GLY LYS
VAL ALA VAL
SER ASP
LEU MET
VAL PHE LEU
LEU THR
GLU
ILE

TYR SER  E   F  PRO LEU ASN  G

EXTRACELLULAR SIDE

```
ATCTGCAGGA TGGGTGCAAC CGTGAAGTCC GTCACGGCTG CGTCACGACA GGAGCCGACC    60

AGGACACCC  AGAAGTGCG  AACGGTTGAG TGCCGCAACG ATCACGAGTT TTTCGTGCGC   120

TTCGAGTGGT AACACGCGTG CACGGCATCGA CTTCACCGCG GGTGTTTCGA CGCCAGCCGG   180

CCGTTGAACC AGCAGGCAGC GGGCATTTCA CATCCCGCTGT GGCCCACACA CTCGGTGGGG   240

TGGCCTATTT TGGTATGGTT TGGAATCCGC CGTGTCGGCTC GTGTCTGAC GGTTCATCGG    300

TCTAAATTCC GTCACGAGCG TACCATACTG ATTGGGTCGT AGAGTTACAC ACATATCCTC    360

GTTAGGTACT GTTGC ATG TTG GAG TTA TTG CCA ACA GCA GTG GAG GGG GTA    411
              Met Leu Glu Leu Leu Pro Thr Ala Val Glu Gly Val
                1                 5                      10

TCG CAG GCC CAG ATC CAG GCG CTG ATG AAC ACT TCA GCC CCA CCT GCT      459
Ser Gln Ala Gln Ile Gln Ala Leu Met Asn Thr Ser Ala Pro Pro Ala
            15                  20                  25

GTC AGC CCC AAC ATC ACC GTC CTG GCA CCA GGA AAG GGT CCC TGG CAA      507
Val Ser Pro Asn Ile Thr Val Leu Ala Pro Gly Lys Gly Pro Trp Gln
        30                  35                  40
```

FIG. 6(A)

```
GTG GCC TTC ATT GGG ATC ACC ACG GGC CTC CTG TCG CTA GCC ACA GTG    555
Val Ala Phe Ile Gly Ile Thr Thr Gly Leu Leu Ser Leu Ala Thr Val
 45                  50                  55                  60

ACA GGC AAC CTG CTG GTA CTC ATC TCT TTC AAG GTC AAC ACG GAG CTC    603
Thr Gly Asn Leu Leu Val Leu Ile Ser Phe Lys Val Asn Thr Glu Leu
             65                  70                  75

AAG ACA GTC AAT AAC TAC TTC CTG CTG AGC CTG GCC TGT GCT GAC CTC    651
Lys Thr Val Asn Asn Tyr Phe Leu Leu Ser Leu Ala Cys Ala Asp Leu
         80                  85                  90

ATC ATC GGT ACC TTC TCC ATG AAC CTC TAT ACC ACG TAC CTG CTC ATG    699
Ile Ile Gly Thr Phe Ser Met Asn Leu Tyr Thr Thr Tyr Leu Leu Met
     95                 100                 105

GGC CAC TGG GCT CTG GGC ACG CTG GCT TGT GAC CTC TGG CTG GCC CTG    747
Gly His Trp Ala Leu Gly Thr Leu Ala Cys Asp Leu Trp Leu Ala Leu
110                 115                 120

GAC TAT GTG GCC AGC AAT GCC TCC GTC ATG AAT CTG CTC CTC ATC AGC    795
Asp Tyr Val Ala Ser Asn Ala Ser Val Met Asn Leu Leu Leu Ile Ser
125                 130                 135                 140
```

FIG. 6(B)

| | | | | | | | | | | | | | | | | |
|---|---|---|---|---|---|---|---|---|---|---|---|---|---|---|---|---|
| TTT | GAC | CGC | TAC | TTC | TCC | GTG | ACT | CGG | CCC | CTG | AGC | TAC | CGT | GCC | AAG | 843 |
| Phe | Asp | Arg | Tyr | Phe | Ser | Val | Thr | Arg | Pro | Leu | Ser | Tyr | Arg | Ala | Lys | |
| | | | 145 | | | | | | 150 | | | | | | 155 | |
| CGC | ACA | CCC | CGC | CGC | GCA | GCT | CTG | ATG | ATC | GGC | CTG | GCC | TGG | CTG | GTT | 891 |
| Arg | Thr | Pro | Arg | Arg | Ala | Ala | Leu | Met | Ile | Gly | Leu | Ala | Trp | Leu | Val | |
| | | 160 | | | | | 165 | | | | | 170 | | | | |
| TCC | TTT | GTG | CTC | TGG | GCC | CCA | GCC | ATC | CTC | TTC | TGG | CAA | TAC | CTG | GTA | 939 |
| Ser | Phe | Val | Leu | Trp | Ala | Pro | Ala | Ile | Leu | Phe | Trp | Gln | Tyr | Leu | Val | |
| | 175 | | | | | | 180 | | | | | | 185 | | | |
| GGG | GAG | CGG | ACG | ATG | CTA | GCT | CTG | TAC | ATC | CAG | TTC | CTC | TCC | 987 | | |
| Gly | Glu | Arg | Thr | Met | Leu | Ala | Gly | Gln | Cys | Tyr | Ile | Gln | Phe | Leu | Ser | |
| | 190 | | | | | | 195 | | | | | 200 | | | | |
| CAG | CCC | ATC | ATC | ACC | TTT | GGC | ACA | GCC | ATG | GCT | GCC | TTC | TAC | CTC | CCT | 1035 |
| Gln | Pro | Ile | Ile | Thr | Phe | Gly | Thr | Ala | Met | Ala | Ala | Phe | Tyr | Leu | Pro | |
| 205 | | | | | | 210 | | | | | 215 | | | | 220 | |
| GTC | ACA | GTC | ATG | TGC | ACG | CTC | TAC | TGG | CGC | ATC | TAC | CGG | GAG | ACA | GAG | 1083 |
| Val | Thr | Val | Met | Cys | Thr | Leu | Tyr | Trp | Arg | Ile | Tyr | Arg | Glu | Thr | Glu | |
| | | | | 225 | | | | | 230 | | | | | 235 | | |

FIG. 6(C)

```
AAC CGA GCA CGG GAG CTG GCA GCC CTT CAG GGC TCC GAG ACG CCA GGC    1131
Asn Arg Ala Arg Glu Leu Ala Ala Leu Gln Gly Ser Glu Thr Pro Gly
        240                 245                 250

AAA GGG GGT GGC AGC AGC AGC TCA GAG AGG TCT CAG GGG CCA GGG GCA    1179
Lys Gly Gly Gly Ser Ser Ser Ser Glu Arg Ser Gln Gly Pro Gly Ala
        255                 260                 265

GAG GGC TCA CCA GAG ACT CCT CCA GGC TCA CCT CCA GGC CGC TGT CGT    1227
Glu Gly Ser Pro Glu Thr Pro Pro Gly Ser Pro Pro Gly Arg Cys Cys
        270                 275                 280

GCC CCA AGG CTG CTG CAA GCC TAC AGC TGG AAG GAA GAA GAG GAA GAG    1275
Ala Pro Arg Leu Leu Gln Ala Tyr Ser Trp Lys Glu Glu Glu Glu Glu
        285                 290                 295         300

GAC GAA GGC TCC ATG GAG TCC CTC ACA TCC TCA GAG GGA GAG CCT        1323
Asp Glu Gly Ser Met Glu Ser Leu Thr Ser Ser Glu Gly Glu Pro
        305                 310                 315

GGC TCC GAA GTG GTG ATC AAG ATG CCA ATG GTG GAC CCC GAG GCA CAG    1371
Gly Ser Glu Val Val Ile Lys Met Pro Met Val Asp Pro Glu Ala Gln
        320                 325                 330
```

FIG. 6(D)

```
GCC CCC ACC AAG CAG CCC CCA CGG AGC TCC CCA AAT ACA GTC AAG AGG   1419
Ala Pro Thr Lys Gln Pro Pro Arg Ser Ser Pro Asn Thr Val Lys Arg
            335                 340                 345

CCG ACT AAG AAA GGG CGT GAT CGA GCT GGC AAG GGC CAG AAG CCC CGT   1467
Pro Thr Lys Lys Gly Arg Asp Arg Ala Gly Lys Gly Gln Lys Pro Arg
            350                 355                 360

GGA AAG GAG CAG CTG GCC AAG CGG AAG ACC TTC TCG CTG GTC AAG GAG   1515
Gly Lys Glu Gln Leu Ala Lys Arg Lys Thr Phe Ser Leu Val Lys Glu
            365                 370                 375         380

AAG AAG GCG GCT CGG ACC CTG AGT GCC ATC CTC CTG GCC TTC ATC CTC   1563
Lys Lys Ala Ala Arg Thr Leu Ser Ala Ile Leu Leu Ala Phe Ile Leu
            385                 390                 395

ACC TGG ACA CCG TAC AAC ATC ATG GTG CTG GTG TCC ACC TTC TGC AAG   1611
Thr Trp Thr Pro Tyr Asn Ile Met Val Leu Val Ser Thr Phe Cys Lys
            400                 405                 410

GAC TGT GTT CCC GAG ACC CTG TGG GAG CTG GGC TAC TGG CTG TGC TAC   1659
Asp Cys Val Pro Glu Thr Leu Trp Glu Leu Gly Tyr Trp Leu Cys Tyr
            415                 420                 425
```

FIG. 6(E)

```
GTC AAC AGC ACC ATC AAC CCC ATG TGC TAC GCA CTC TGC AAC AAA GCC      1707
Val Asn Ser Thr Ile Asn Pro Met Cys Tyr Ala Leu Cys Asn Lys Ala
430                             435                         440

TTC CGG GAC ACC TTT CGC CTG CTT TGC CGC TGG GAC AAG AGA CGC          1755
Phe Arg Asp Thr Phe Arg Leu Leu Cys Arg Trp Asp Lys Arg Arg
445                             450                     455      460

TGG CGC AAG ATC CCC AAG CGC CCT GGC TCC GTG CAC CGC ACT CCC TCC      1803
Trp Arg Lys Ile Pro Lys Arg Pro Gly Ser Val His Arg Thr Pro Ser
            465                         470                475

CGC CAA TGC TGATAGTCCC CTCTCCTGCA TCCCTCCACC CCAGCGGCCG              1852
Arg Gln Cys

CGACCAGGGA TTGATCGCAC ACGCAGGACA GCCCCACAAC CGGGCGGGCT GTGTTCAACG    1912

ACACACGATG AGTCCCCCAC TCGGTCTTGT ACTCGGATCC TTTT                     1956
```

FIG. 6(F)

```
ATCTGCAGGA TGGGTGCAAC CGTGAAGTCC CGTCACGACA GGAGCCGACC                    60

AGCCGACACCC AGAAGGTGCG AACGGTTGAG TGCCGCAACG ATCACGAGTT TTTCGTGCGC        120

TTCGAGTGGT AACACGGCGT CACGGCATCGA CTTCACCGCG GGTGTTTCGA CGCCAGCCGG       180

CCGTTGAACC AGCAGGCAGC GGGCATTTCA CATCCGCTGT GGCCCACACA CTCGGTGGGG        240

TGGGCTATTT TGGTATGGTT TGGAATCCGC GTGTCGGCTC CGTGTCTGAC GGTTCATCGG       300

TCTAAATTCC GTCACGAGCG TACCATACTG ATTGGGTCGT AGAGTTACAC ACATATCCTC        360

GTTAGGTACT GTTGC ATG TTG GAG TTA TTG CCA ACA GCA GTG GAG GGG GTA        411
              Met Leu Glu Leu Leu Pro Thr Ala Val Glu Gly Val
               1               5                      10

TCG CAG GCC CAG ATC CAG GCG CTG ATG AAC ACT TCA GCC CCA CCT GCT         459
Ser Gln Ala Gln Ile Gln Ala Leu Met Asn Thr Ser Ala Pro Pro Ala
             15                  20                  25

GTC AGC CCC AAC ATC ACC GTC CTG GCA CCA GGA AAG GGT CCC TGG CAA         507
Val Ser Pro Asn Ile Thr Val Leu Ala Pro Gly Lys Gly Pro Trp Gln
         30                  35                  40

FIG. 8(A)
```

```
GTG GCC TTC ATT GGG ATC ACC ACG GGC CTC CTG TCG CTA GCC ACA GTG      555
Val Ala Phe Ile Gly Ile Thr Thr Gly Leu Leu Ser Leu Ala Thr Val
 45                  50                  55                  60

ACA GGC AAC CTG CTG GTA CTC ATC TCT TTC AAG GTC AAC ACG GAG CTC      603
Thr Gly Asn Leu Leu Val Leu Ile Ser Phe Lys Val Asn Thr Glu Leu
             65                  70                  75

AAG ACA GTC AAT AAC TAC TTC CTG CTG AGC CTG GCC TGT GCT GAC CTC      651
Lys Thr Val Asn Asn Tyr Phe Leu Leu Ser Leu Ala Cys Ala Asp Leu
         80                  85                  90

ATC ATC GGT ACC TTC TCC ATG AAC CTC TAT ACC ACG TAC CTG CTC ATG      699
Ile Ile Gly Thr Phe Ser Met Asn Leu Tyr Thr Thr Tyr Leu Leu Met
     95                 100                 105

GGC CAC TGG GCT CTG GGC ACG CTG GCT TGT GAC CTC TGG CTG GCC CTG      747
Gly His Trp Ala Leu Gly Thr Leu Ala Cys Asp Leu Trp Leu Ala Leu
 110                 115                 120

GAC TAT GTG GCC AGC AAT GCC TCC GTC ATG AAT CTG CTC ATC AGC          795
Asp Tyr Val Ala Ser Asn Ala Ser Val Met Asn Leu Leu Ile Ser
 125                 130                 135                 140
```

FIG. 8(B)

```
TTT GAC CGC TAC TTC TCC GTG ACT CGG CCC CTG AGC TAC CGT GCC AAG      843
Phe Asp Arg Tyr Phe Ser Val Thr Arg Pro Leu Ser Tyr Arg Ala Lys
145                 150                 155

CGC ACA CCC CGC GCA GCT CTG ATG ATC GGC CTG GCC TGG CTG GTT          891
Arg Thr Pro Arg Ala Ala Leu Met Ile Gly Leu Ala Trp Leu Val
    160                 165                 170

TCC TTT GTG CTC TGG GCC CCA GCC ATC CTC TTC TGG CAA TAC CTG GTA      939
Ser Phe Val Leu Trp Ala Pro Ala Ile Leu Phe Trp Gln Tyr Leu Val
            175                 180                 185

GGG GAG CGG ACG ATG CTA GCT GGG CAG TGC TAC ATC CAG TTC CTC TCC      987
Gly Glu Arg Thr Met Leu Ala Gly Gln Cys Tyr Ile Gln Phe Leu Ser
190                 195                 200

CAG CCC ATC ATC ACC TTT GGC ACC ATG GCT GCC ATG GCT GCC TTC TAC CTC CCT   1035
Gln Pro Ile Ile Thr Phe Gly Thr Met Ala Ala Phe Tyr Leu Pro
205                 210                 215                 220

GTC ACA GTC ATG TGC ACG CTC TAC TGG CGC ATC TAC CGG GAG ACA GAG      1083
Val Thr Val Met Cys Thr Leu Tyr Trp Arg Ile Tyr Arg Glu Thr Glu
            225                 230                 235
```

FIG. 8(C)

```
AAC CGA GCA CGG GAG CTG GCA GCC CTT CAG GGC TCC GAG ACG CCA GGC      1131
Asn Arg Ala Arg Glu Leu Ala Ala Leu Gln Gly Ser Glu Thr Pro Gly
        240                 245                 250

AAA AAG GAG AAG AAG GCG GCT CGG ACC CTG AGT GCC ATC CTC CTG GCC      1179
Lys Lys Glu Lys Lys Ala Ala Arg Thr Leu Ser Ala Ile Leu Leu Ala
        255                 260                 265

TTC ATC CTC ACC TGG ACA CCG TAC AAC ATC ATG GTG CTG GTG TCC ACC      1227
Phe Ile Leu Thr Trp Thr Pro Tyr Asn Ile Met Val Leu Val Ser Thr
        270                 275                 280

TTC TGC AAG GAC TGT GTT CCC GAG ACC CTG TGG GAG CTG GGC TAC TGG      1275
Phe Cys Lys Asp Cys Val Pro Glu Thr Leu Trp Glu Leu Gly Tyr Trp
        285                 290                 295                 300

CTG TGC TAC GTC AAC AGC ACC ATC AAC CCC ATG TGC TAC GCA CTC TGC      1323
Leu Cys Tyr Val Asn Ser Thr Ile Asn Pro Met Cys Tyr Ala Leu Cys
        305                 310                 315

AAC AAA GCC TTC CGG GAC ACC TTT CGC CTG CTT CTG TGC CGC TGG GAC      1371
Asn Lys Ala Phe Arg Asp Thr Phe Arg Leu Leu Leu Cys Arg Trp Asp
        320                 325                 330
```

FIG. 8(D)

```
AAG AGA CGC TGG CGC AAG ATC CCC AAG CGC CCT GGC TCC GTG CAC CGC       1419
Lys Arg Arg Trp Arg Lys Ile Pro Lys Arg Pro Gly Ser Val His Arg
            335                     340                     345

ACT CCC TCC CGC CAA TGC TGATAGTCCC CTCTCCTGCA TCCCTCCACC              1467
Thr Pro Ser Arg Gln Cys
        350

CCAGCGGCCG CGACCAGCGA TTGATCGGCAC ACGGAGGACA GCCCCACAAC CGGGCGGGCT    1527

GTGTTCAACG ACACACGATG AGTCCCCCAC TCGGTCTTGT ACTCGGATCC TTTT           1581
```

FIG.8(E)

```
ATCTGCAGGA TGGTGCAAC CGTGAAGTCC CGTCACGACA GGAGCCGACC                                    60

AGGGACACCC AGAAGGTGCG AACGGTTGAG TGCCCGAACG ATCACGAGTT TTTCGTGCGC                         120

TTCGAGTGGT AACACGGCGT CACGGCATCGA CTTCACCGCG CGGTGTTTCGA CGCCAGCCGG                       180

CCGTTGAACC AGCAGGCAGC GGGCATTTCA CATCCGCTGT GGCCCACACA CTCGGTGGGG                         240

TGCGCTATTT TGGTATGGTT TGGAATCCGC CGTGTCGGCTC CGTGTCTGAC GGTTCATCGG                        300

TCTAAATTCC GTCACGAGCG TACCATACTG ATTGGGTCGT AGAGTTACAC ACATATCCTC                         360

GTTAGGTACT GTTGC ATG TTG GAG TTA TTG CCA ACA GCA GTG GAG GGG GTA                          411
              Met Leu Glu Leu Leu Pro Thr Ala Val Glu Gly Val
              1               5                        10

TCG CAG GCC CAG ATC CAG GCG CTG GAC TAC AAG GAC GAT GAC GTC                               459
Ser Gln Ala Gln Ile Gln Ala Leu Asp Tyr Lys Asp Asp Asp Val
            15                  20                  25

GAC ACT TTT AAT TCC TCC GAT GGT GGA CGC TTG TTT CAA TTC CCG GAC                           507
Asp Thr Phe Asn Ser Ser Asp Gly Gly Arg Leu Phe Gln Phe Pro Asp
        30                  35                  40

FIG. 10(A)
```

```
GGG GTA CAA AAC TGG CCA GCA CTT TCA ATC GTC GTG ATT ATA ATC ATG    555
Gly Val Gln Asn Trp Pro Ala Leu Ser Ile Val Val Ile Ile Ile Met
 45                  50                  55                  60

ACA ATA GGG GGC AAC ATT CTT GTT ATC ATG GCA GTA AGC ATG GAG AAG    603
Thr Ile Gly Gly Asn Ile Leu Val Ile Met Ala Val Ser Met Glu Lys
                 65                  70                  75

AAA CTG CAC AAT GCA ACC AAT TAC TTC TTA ATG TCC CTA GCC ATT GCT    651
Lys Leu His Asn Ala Thr Asn Tyr Phe Leu Met Ser Leu Ala Ile Ala
             80                  85                  90

GAT ATG CTG GGA CTA CTT GTC ATG CCC CTG TCC CTG CTT GCT ATT        699
Asp Met Leu Val Gly Leu Leu Val Met Pro Leu Ser Leu Leu Ala Ile
         95                 100                 105

CTT TAT GAT TAT GTC TGG CCT TTA CCT AGA TAT TTG TGC CCC GTC TGG    747
Leu Tyr Asp Tyr Val Trp Pro Leu Pro Arg Tyr Leu Cys Pro Val Trp
    110                 115                 120

ATT TCA CTA GAT GTG CTA TTT TCA ACT GCG TCC ATC ATG CAC CTC TGC    795
Ile Ser Leu Asp Val Leu Phe Ser Thr Ala Ser Ile Met His Leu Cys
125                 130                 135                 140
```

FIG. 10(B)

```
GCC ATA TCG CTG GAC CGG TAT GTA GCA ATA CGT AAT CCT ATT GAG CAT    843
Ala Ile Ser Leu Asp Arg Tyr Val Ala Ile Arg Asn Pro Ile Glu His
            145                 150                 155

AGC CGG TTC AAT TCG CGG ACT AAG GCC ATC ATG AAG ATT GCC ATC GTT    891
Ser Arg Phe Asn Ser Arg Thr Lys Ala Ile Met Lys Ile Ala Ile Val
            160                 165                 170

TGG GCA ATA TCA ATA GGA GTT TCA GTT CCT ATC CCT GTG ATT GGA CTG    939
Trp Ala Ile Ser Ile Gly Val Ser Val Pro Ile Pro Val Ile Gly Leu
            175                 180                 185

AGG GAC GAA AGC AAA GTG TTC GTG AAT AAC ACC ACG TGC GTG CTC AAT    987
Arg Asp Glu Ser Lys Val Phe Val Asn Asn Thr Thr Cys Val Leu Asn
            190                 195                 200

GAC CCC AAC TTC GTT CTC ATC GGG TCC TTC GTG GCA TTC TTC ATC CCG   1035
Asp Pro Asn Phe Val Leu Ile Gly Ser Phe Val Ala Phe Phe Ile Pro
            205                 210                 215                 220

TTG ACG ATT ATG GTG ATC ACC TAC TTC TTA ACG ATC TAC GTC CTG CGC   1083
Leu Thr Ile Met Val Ile Thr Tyr Phe Leu Thr Ile Tyr Val Leu Arg
            225                 230                 235
```

FIG. 10(C)

CGT CAA ACT CTG ATG TTA CTT CGA GGT CAC ACC GAG GAG CTG GCT       1131
Arg Gln Thr Leu Met Leu Leu Arg Gly His Thr Glu Glu Leu Ala
        240                 245                 250

AAT ATG AGC CTG AAC TTT CTG AAC TGC TGC AAG AAG AAT GGT GGT       1179
Asn Met Ser Leu Asn Phe Leu Asn Cys Cys Lys Lys Asn Gly Gly
        255                 260                 265

GAG GAA GAG AAC GCT CCG AAC CCT AAT CCA GAT CAG AAA CCA CGT CGA   1227
Glu Glu Glu Asn Ala Pro Asn Pro Asn Pro Asp Gln Lys Pro Arg Arg
        270                 275                 280

AAG AAA GAA AAG CGT CCC AGA GGC ACC ATG CAA GCT ATC AAC AAC       1275
Lys Lys Glu Lys Arg Pro Arg Gly Thr Met Gln Ala Ile Asn Asn
        285                 290                 295          300

GAA AAG AAA GCT TCC AAA GTC CTT GGC ATT GTA TTC TTT GTG TTT CTG   1323
Glu Lys Lys Ala Ser Lys Val Leu Gly Ile Val Phe Phe Val Phe Leu
        305                 310                 315

ATC ATG TGG TGC CCG TTT TTC ATC ACC AAT ATC CTG TCG GTT CTT TGT   1371
Ile Met Trp Cys Pro Phe Phe Ile Thr Asn Ile Leu Ser Val Leu Cys
        320                 325                 330

*FIG. 10(D)*

```
GGG AAG GCC TGT AAC CAA AAG CTA ATG GAG AAG CTT CTC AAT GTG TTT       1419
Gly Lys Ala Cys Asn Gln Lys Leu Met Glu Lys Leu Leu Asn Val Phe
335                 340                 345

GTG TGG ATT GGC TAT GTG TGT TCA GGC ATC AAT CCT CTG GTG TAC ACT       1467
Val Trp Ile Gly Tyr Val Cys Ser Gly Ile Asn Pro Leu Val Tyr Thr
350                 355                 360

CTC TTT AAT AAA ATT TAC CGA AGG GCT TTC TCT AAA TAT TTG CGC TGC       1515
Leu Phe Asn Lys Ile Tyr Arg Arg Ala Phe Ser Lys Tyr Leu Arg Cys
365                 370                 375                 380

GAT TAT AAG CCA GAC AAA AAG CCT CCT GTT CGA CAG ATT CCT AGG GTT       1563
Asp Tyr Lys Pro Asp Lys Lys Pro Pro Val Arg Gln Ile Pro Arg Val
                385                 390                 395

GCT GCC ACT GCT TTG TCT GGG AGG GAG CTC AAT GTT AAC ATT TAT CGG       1611
Ala Ala Thr Ala Leu Ser Gly Arg Glu Leu Asn Val Asn Ile Tyr Arg
400                 405                 410

CAT ACC AAT GAA CGT GTG GCT AGG AAA GCT AAT GAC CCT GAG CCT GGC       1659
His Thr Asn Glu Arg Val Ala Arg Lys Ala Asn Asp Pro Glu Pro Gly
415                 420                 425
```

FIG. 10(E)

```
ATA GAG ATG CAG GTG GAG AAC TTA GAG CTG CCA GTC AAC CCC TCT AAT    1707
Ile Glu Met Gln Val Glu Asn Leu Glu Leu Pro Val Asn Pro Ser Asn
430                         435                         440

GTG GTC AGC GAG GAG AGG ATT AGT AGT GTG TGAGCGGGCCG CGACCAGCGA     1754
Val Val Ser Glu Glu Arg Ile Ser Ser Val
445                         450

TTGATCGGCAC ACGCAGGACA GCCCCACAAC CGGGCGGGCT GTGTTCAACG ACACACGATG  1814

AGTCCCCCAC TCGGTCTTGT ACTCGGATCC TTTT                               1848
```

FIG. 10(F)

```
ATCTGCAGGA TGGGTGCAAC CGTGAAGTCC GTCACGGCTG CGTCACGACA GGAGCCGACC      60

AGGACACCC AGAAGGTGCG AACGGGTTGAG TGCCGGCAACG ATCACGGAGTT TTTCGTGCGC    120

TTCGAGTGGT AACACGGGTG CACGCATCGA CTTCACCGCG GGTGTTTCGA CGCCAGCCCGG    180

CCGTTGAACC AGCAGGCAGC GGGCATTTCA CATCCGCTGT GGCCCACACA CTCGGTGGGG    240

TGCGCTATTT TGGTATGGTT TGGAATCCGC GTGTCGGCTC CGTGTCTGAC GGTTCATCGG    300

TCTAAATTCC GTCACGAGCG TACCATACTG ATTGGGTCGT AGAGTTACAC ACATATCCTC    360

GTTAGGTACT GTGC ATG TTG GAG TTA TTG CCA ACA GCA GTG GAG GGG GTA      411
              Met Leu Glu Leu Leu Pro Thr Ala Val Glu Gly Val
              1               5                       10

TCG CAG GCC CAG ATC CAG GCG CTG GAC TAC AAG GAC GAT GAT GAC GTC       459
Ser Gln Ala Gln Ile Gln Ala Leu Asp Tyr Lys Asp Asp Asp Asp Val
             15                       20                       25

GAC GCC ACC TTA GAT CCC CGG TCA TTT CTC AGG AAC CCC AAT GAT            507
Asp Ala Thr Leu Asp Pro Arg Ser Phe Leu Arg Asn Pro Asn Asp
         30                       35                       40
```

FIG. 14(A)

```
AAA TAT GAA CCA TTT TGG GAG GAT GAG GAG AAA AAT GAA AGT GGG TTA    555
Lys Tyr Glu Pro Phe Trp Glu Asp Glu Glu Lys Asn Glu Ser Gly Leu
 45                  50                  55                  60

ACT GAA TAC AGA TTA GTC TCC ATC AAT AAA AGC AGT CCT CTT CAA AAA    603
Thr Glu Tyr Arg Leu Val Ser Ile Asn Lys Ser Ser Pro Leu Gln Lys
             65                  70                  75

CAA CTT CCT GCA TTC ATC TCA GAA GAT GCC TCC GGA TAT TTG ACC AGC    651
Gln Leu Pro Ala Phe Ile Ser Glu Asp Ala Ser Gly Tyr Leu Thr Ser
         80                  85                  90

TCC TGG CTG ACA CTC TTT GTC CCA TCT GTG TAC ACC GGA GTG TTT GTA    699
Ser Trp Leu Thr Leu Phe Val Pro Ser Val Tyr Thr Gly Val Phe Val
     95                 100                 105

GTC AGC CTC CCA CTA AAC ATC ATG GCC ATC GTT GTC TTC ATC CTG AAA    747
Val Ser Leu Pro Leu Asn Ile Met Ala Ile Val Val Phe Ile Leu Lys
110                 115                 120

ATG AAG GTC AAG AAG CCG GCG GTG GTG TAC ATG CTG CAC CTG GCC ACG    795
Met Lys Val Lys Lys Pro Ala Val Val Tyr Met Leu His Leu Ala Thr
125                 130                 135                 140
```

FIG. 14(B)

```
GCA GAT GTG CTG TTT GTG TCT GTG CTC CCC TTT AAG ATC AGC TAT TAC    843
Ala Asp Val Leu Phe Val Ser Val Leu Pro Phe Lys Ile Ser Tyr Tyr
        145                 150                 155

TTT TCC GGC AGT GAT TGG CAG TTT GGG TCT GAA TTG TGT CGC TTC GTC    891
Phe Ser Gly Ser Asp Trp Gln Phe Gly Ser Glu Leu Cys Arg Phe Val
        160                 165                 170

ACT GCA GCA TTT TAC TGT AAC ATG TAC GCC TCT ATC TTG CTC ATG ACA    939
Thr Ala Ala Phe Tyr Cys Asn Met Tyr Ala Ser Ile Leu Leu Met Thr
        175                 180                 185

GTC ATA AGC ATT GAC CGG TTT CTG GCT GTG TAT CCC ATG CAG TCC        987
Val Ile Ser Ile Asp Arg Phe Leu Ala Val Tyr Pro Met Gln Ser
        190                 195                 200

CTC TCC TGG CGT ACT CTG GGA AGG GCT TCC TTC ACT TGT CTG GCC ATC   1035
Leu Ser Trp Arg Thr Leu Gly Arg Ala Ser Phe Thr Cys Leu Ala Ile
        205                 210                 215                 220

TGG GCT TTG GCC ATC GCA GGG GTA GTG CCT CTC GTC CTC AAG GAG CAA   1083
Trp Ala Leu Ala Ile Ala Gly Val Val Pro Leu Val Leu Lys Glu Gln
        225                 230                 235
```

FIG. 14(C)

```
ACC ATC CAG GTG CCC GGG CTC AAC ATC ACT ACC TGT CAT GAT GTG CTC    1131
Thr Ile Gln Val Pro Gly Leu Asn Ile Thr Thr Cys His Asp Val Leu
            240                 245                 250

AAT GAA ACC CTG CTC GAA GGC TAC TAT GCC TAC TTC TCA GCC TTC        1179
Asn Glu Thr Leu Leu Glu Gly Tyr Tyr Ala Tyr Phe Ser Ala Phe
        255                 260                 265

TCT GCT GTC TTC TTT TTT GTG CCG CTG ATC ATT TCC ACG GTC TGT TAT    1227
Ser Ala Val Phe Phe Phe Val Pro Leu Ile Ile Ser Thr Val Cys Tyr
        270                 275                 280

GTG TCT ATC ATT CGA TGT CTT AGC TCT TCC GCA GTT GCC AAC CGC AGC    1275
Val Ser Ile Ile Arg Cys Leu Ser Ser Ser Ala Val Ala Asn Arg Ser
    285                 290                 295                 300

AAG AAG TCC CGG GCT TTG TTC CTG TCA GCT GCT GTT TTC TGC ATC TTC    1323
Lys Lys Ser Arg Ala Leu Phe Leu Ser Ala Ala Val Phe Cys Ile Phe
            305                 310                 315

ATC ATT TGC TTC GGA CCC ACA AAC GTC CTC CTG ATT GCG CAT TAC TCA    1371
Ile Ile Cys Phe Gly Pro Thr Asn Val Leu Leu Ile Ala His Tyr Ser
        320                 325                 330
```

*FIG. 14(D)*

```
TTC CTT TCT CAC ACT TCC ACC ACA GAG GCT GCC TAC TTT GCC TAC CTC    1419
Phe Leu Ser His Thr Ser Thr Thr Glu Ala Ala Tyr Phe Ala Tyr Leu
        335                 340                 345

CTC TGT TGT GTC AGC AGC ATA AGC TCG TGC ATC GAC CCC CTA ATT        1467
Leu Cys Val Cys Val Ser Ser Ile Ser Cys Ile Asp Pro Leu Ile
    350                 355                 360

TAC TAT TAC GCT TCC TCT GAG TGC CAG AGG TAC GTC TAC AGT ATC TTA    1515
Tyr Tyr Tyr Ala Ser Ser Glu Cys Gln Arg Tyr Val Tyr Ser Ile Leu
365                 370                 375                 380

TGC AAA GAA AGT TCC GAT CCC AGC AGT TAT AAC AGC AGT GGG CAG        1563
Cys Lys Glu Ser Ser Asp Pro Ser Ser Tyr Asn Ser Ser Gly Gln
        385                 390                 395

TTG ATG GCA AGT AAA ATG GAT ACC TGC TCT AGT AAC CTG AAT AAC AGC    1611
Leu Met Ala Ser Lys Met Asp Thr Cys Ser Ser Asn Leu Asn Asn Ser
    400                 405                 410
```

FIG. 14(E)

```
ATA TAC AAA AAG CTG TTA ACT CAC CAC CAC CAC CAC TGAGCGGCCG        1660
Ile Tyr Lys Lys Leu Leu Thr His His His His His His
            415                 420                 425

CGACCAGCGA TTGATCGCAC ACGCAGGACA GCCCCACAAC CGGCGCGGCT GTGTTCAACG  1720

ACACACGATG AGTCCCCCAC TCGGTCTTGT ACTCGGATCC TTTT                  1764
```

*FIG. 14(F)*

TAATCTGCAG GATGGGTGCA ACCGTGAAGT CCGTCACGGC TGCGTCACGA CAGGAGCCGA    60

CCAGCGACAC CCAGAAGGTG CGAACGGTTG AGTGCCGCAA CGATCACGAG TTTTTCGTGC   120

GCTTCGAGTG GTAACACGCG TGCACGCCATC GACTTCACCG CGGGTGTTTC GACGCCAGCC  180

GGCCGTTGAA CCAGCAGGCA GCGGGCATTT CACAGCCGCT GTGGCCCACA CACTCGGTGG   240

GGTGCGGCTAT TTTGGTATGG TTTGGAATCC GCGTGTCGGC TCCGTGTCTG ACGGTTCATC  300

GGTCTAAATT CCGTCACGAG CGTACCATAC TGATTGGGTC GTAGAGTTAC ACACATATCC   360

TCGTTAGGTA CTGTTGC ATG TTG GAG TTA TTG CCA ACA GCA GTG GAG GGG     410
                   Met Leu Glu Leu Leu Pro Thr Ala Val Glu Gly
                    1               5                      10

CTA TCG CAG GCC CAG ATC ACC GGA CGT CCG GAG TGG ATC TGG CTA GCG    458
Val Ser Gln Ala Gln Ile Thr Gly Arg Pro Glu Trp Ile Trp Leu Ala
                15                      20                      25

CTC GGT ACG GCG CTA ATG GGA CTC GGG ACG CTC TAT TTC CTC GTG AAA    506
Leu Gly Thr Ala Leu Met Gly Leu Gly Thr Leu Tyr Phe Leu Val Lys
            30                      35                      40

FIG. 17(A)

```
GGG ATG GGC GTC TCG GAC CCA GAT GCA AAG AAA TTC TAC GCC ATC ACG      554
Gly Met Gly Val Ser Asp Pro Asp Ala Lys Lys Phe Tyr Ala Ile Thr
 45                  50                  55

ACG CTC GTC CCA GCC ATC GCG TTC ACG ATG TAC CTC TCG ATG CTG CTG      602
Thr Leu Val Pro Ala Ile Ala Phe Thr Met Tyr Leu Ser Met Leu Leu
         60                  65                  70              75

GGG TAT GGC CTC ACA ATG GTA CCG TTC GGT GGG GAG GAG AAC CCC ATC      650
Gly Tyr Gly Leu Thr Met Val Pro Phe Gly Gly Glu Gln Asn Pro Ile
         80                  85                  90

TAC TGG GCG CGG TAC GCT GAC TGG CTG TTC ACC ACG CCG CTG TTG TTG      698
Tyr Trp Ala Arg Tyr Ala Asp Trp Leu Phe Thr Thr Pro Leu Leu Leu
             95                 100                 105

TTA GAC CTC GCG TTG CTC GTT GAC GCC GAT CAG GGA ACG ATC CTT GCG      746
Leu Asp Leu Ala Leu Leu Val Asp Ala Asp Gln Gly Thr Ile Leu Ala
        110                 115                 120

CTC GTC GGT GCC GAC GGC ATC ATG ATC GGG ACC GGC CTC GTC GGC GCA      794
Leu Val Gly Ala Asp Gly Ile Met Ile Gly Thr Gly Leu Val Gly Ala
        125                 130                 135
```

FIG. 17(B)

```
CTG ACG AAG GTC TAC TCG TAC CGC TTC GTG TGG GCG ATC AGC ACC    842
Leu Thr Lys Val Tyr Ser Tyr Arg Phe Val Trp Ala Ile Ser Thr
140                 145                 150                 155

GCA GCG ATG CTG TAC ATC CTG TAC GTG CTG TTC GGG TTC ACC TCG    890
Ala Ala Met Leu Tyr Ile Leu Tyr Val Leu Phe Gly Phe Thr Ser
                160                 165                 170

AAG GCC GAA AGC ATG CGC CCC GAG GTC GCA TCC ACG TTC AAA GTA CTG  938
Lys Ala Glu Ser Met Arg Pro Glu Val Ala Ser Thr Phe Lys Val Leu
        175                 180                 185

CGT AAC GTT ACC GTT GTG TTG TGG TCC GCG TAT CCC GTC GTG TGG CTG  986
Arg Asn Val Thr Val Val Leu Trp Ser Ala Tyr Pro Val Val Trp Leu
    190                 195                 200

ATC GGC AGC GAA GGT GCG GGA ATC GTG CCG AAC ATC GAG ACG CTG    1034
Ile Gly Ser Glu Gly Ala Gly Ile Val Pro Asn Ile Glu Thr Leu
205                 210                 215

CTG TTC ATG GTG CTT GAC GTG AGC GCG AAG GTC GGC TTC GGG CTC ATC  1082
Leu Phe Met Val Leu Asp Val Ser Ala Lys Val Gly Phe Gly Leu Ile
220                 225                 230                 235
```

FIG. 17(C)

```
CTC CTG CGC AGT CGT GCG ATC TTC GGC GAA GCC GAA GCG CCG ATC GAA    1130
Leu Leu Arg Ser Arg Ala Ile Phe Gly Glu Ala Glu Ala Pro Ile Glu
240                 245                 250

GGT CGT CAG AAA CAT ATC ATT TCC ATA AAC GAC CTT AGT CGC GAT GAC    1178
Gly Arg Gln Lys His Ile Ile Ser Ile Asn Asp Leu Ser Arg Asp Asp
        255                 260                 265

CTT AAT CTG GTG CTG GCG ACA GCG AAA GCG AAA CTG AAA GCA AAC CCG CAA    1226
Leu Asn Leu Val Leu Ala Thr Ala Lys Ala Lys Leu Lys Ala Asn Pro Gln
270                 275                 280

CCA GAG CTG TTG AAG CAC AAA GTC ATT GCC AGC TGT TTC TTC GAA GCC    1274
Pro Glu Leu Leu Lys His Lys Val Ile Ala Ser Cys Phe Phe Glu Ala
    285                 290                 295

TCT ACC CGT ACC CGC CTC TCT TTT CAA ACA TCT ATG CAC CGC CTG GGG    1322
Ser Thr Arg Thr Arg Leu Ser Phe Gln Thr Ser Met His Arg Leu Gly
300                 305                 310                 315

GCC AGC GTG GTG GGC TTC TCC GAC AGC GCC AAT ACA TCA CTG GGT AAA    1370
Ala Ser Val Val Gly Phe Ser Asp Ser Ala Asn Thr Ser Leu Gly Lys
        320                 325                 330
```

FIG. 17(D)

```
AAA GGC GAA ACG CTT GCC GAT ACC ATT TCA GTT ATC AGC ACT TAC GTC      1418
Lys Gly Glu Thr Leu Ala Asp Thr Ile Ser Val Ile Ser Thr Tyr Val
            335                 340                 345

GAT GCG ATA GTG ATG CGT CAT CCG CAG GAA GGT GCG GCC CTG CGC          1466
Asp Ala Ile Val Met Arg His Pro Gln Glu Gly Ala Ala Arg Leu Ala
            350                 355                 360

ACC GAG TTT TCC GGC AAT GTA CCG GTA CTG AAT GCC GGT GAT GGC TCC      1514
Thr Glu Phe Ser Gly Asn Val Pro Val Leu Asn Ala Gly Asp Gly Ser
            365                 370                 375

AAC CAA CAT CCG ACG CAA ACC TTG CTG GAC TTA TTC ACT ATT CAG GAA      1562
Asn Gln His Pro Thr Gln Thr Leu Leu Asp Leu Phe Thr Ile Gln Glu
            380                 385                 390                 395

ACC CAG GGG CGT CTG GAC AAT CTC CAC GTC GCA ATG GTT GGT GAC CTG      1610
Thr Gln Gly Arg Leu Asp Asn Leu His Val Ala Met Val Gly Asp Leu
            400                 405                 410

AAA TAT GGT CGC ACC GTT CAC TCC CTG ACT CAG GCG TTA GCT AAG TTC      1658
Lys Tyr Gly Arg Thr Val His Ser Leu Thr Gln Ala Leu Ala Lys Phe
            415                 420                 425
```

FIG. 17(E)

```
GAC GGC AAC CGT TTT TAC TTC ATC GCG CCG GAC GCG CTG GCA ATG CCG    1706
Asp Gly Asn Arg Phe Tyr Phe Ile Ala Pro Asp Ala Leu Ala Met Pro
        430             435             440

CAA TAC ATT CTG GAT ATG CTC GAT GAA AAA GGG ATC GCA TGG AGT CTG    1754
Gln Tyr Ile Leu Asp Met Leu Asp Glu Lys Gly Ile Ala Trp Ser Leu
        445             450             455

CAC AGC TCT ATT GAA GAA GTG ATG GTG GAA GTA GAC ATC CTG TAC ATG    1802
His Ser Ser Ile Glu Glu Val Met Val Glu Val Asp Ile Leu Tyr Met
        460             465             470             475

ACC CGC GTG CAA AAA GAG CGT CTG GAC CGC TCC GAG TAC GCC AAC GTG    1850
Thr Arg Val Gln Lys Glu Arg Leu Asp Arg Ser Glu Tyr Ala Asn Val
        480             485             490

AAA GCG CAG TTT GTT CTT CGC GCC AGT GAT CTC CAC AAC GCC AAA GCC    1898
Lys Ala Gln Phe Val Leu Arg Ala Ser Asp Leu His Asn Ala Lys Ala
        495             500             505

AAT ATG AAA GTG CTG CAT CCG TTG CCG CGT GTT GAT GAG ATT GCG ACG    1946
Asn Met Lys Val Leu His Pro Leu Pro Arg Val Asp Glu Ile Ala Thr
        510             515             520
```

FIG. 17(F)

```
GAT GTT GAT AAA ACG CCA CAC GCC TGG TAC TTC CAG CAG GCA GGC AAC    1994
Asp Val Asp Lys Thr Pro His Ala Trp Tyr Phe Gln Gln Ala Gly Asn
525                           530                           535

GGG ATT TTC GCT CTG CAA GGG TTA CTG GCA CTG GTT CTG AAT CGG GCC    2042
Gly Ile Phe Ala Leu Gln Gly Leu Leu Ala Leu Val Leu Asn Arg Ala
540                           545                           550                           555

GCG ACC AGC GAC TGATCGGCACA CGCAGGACAG CCCCACAACC GGGCGGCTG        2094
Ala Thr Ser Asp

TGTTCAACGA CACACGATGA GTCCCCCCACT CGGTCTTGTA CTCGGATCCT TTT        2147
```

FIG. 17(G)

EXPRESSION OF HETEROLOGOUS POLYPEPTIDES IN HALOBACTERIA

REFERENCE TO RELATED APPLICATIONS

This is a continuation of application Ser. No. 08/313,553 filed on Sep. 27, 1994, now U.S. Pat. No. 5,641,650, which is a continuation of application Ser. No. 08/038,662 filed Mar. 25, 1993, now abandoned.

The Government has rights in this invention pursuant to Grant No. GM-31785 awarded by the National Institutes of Health.

FIELD OF THE INVENTION

The present invention is directed to the preparation and use of a halobacterial expression system that is capable of producing soluble and transmembrane heterologous polypeptides that are not endogenous to said halobacterium.

BACKGROUND OF THE INVENTION

Halobacteria are found in nature in evaporating salt water ponds under conditions of intense light and low oxygen saturation. They contain distinctive brightly colored pigments such as the orange-red pigment, bacterioruberin, or patches of "purple membrane". Halobacteria belong to a phylogenetically distinct group of prokaryotic organisms—the "archaebacteria" (Arcbaea)—that are as distantly related to the eubacteria as they are to the eukaryotes.

Archaebacteria possess some attributes in common with the eukaryotes and the eubacteria, as well as characteristics that are uniquely archaeal. For example, the archaebacteria possess a eukaryotic-like transcription apparatus with a 7–12 subunit RNA polymerase which is immunologically related to eukaryotic RNA polymerase (1) and promoter structures are similar to those of RNA Pol II (2). In contrast, the archaebacteria have prokaryotic cellular morphology and 23S, 16S and 5S rRNAs with the genes encoding the rRNAs arranged into eubacterial-like operons (3). Notably, the archaebacteria are unique in their membrane composition.

Bacteriorhodopsin (BR) is found as the sole protein in specialized crystalline patches of the "purple membrane" in halobacteria. Synthesis of BR is induced by high light intensity and low oxygen tension and the patches of purple membrane can constitute up to 50% of the archaebacterium *Halobacterium halobium* cell surface area.

BR consists of a complex of one protein (bacterio-opsin) along with the chromophore retinal in a 1:1 stoichiometric ratio (4). This complex is embedded in the lipid matrix as seven transmembrane hydrophobic α-helices in a trimeric configuration (5). Retinal is covalently attached at lysine at position 216 approximately one-third of the way across the transmembraneous region of one of the α-helices (6). The complex of bacterio-opsin with retinal was named bacteriorhodopsin (BR). The so-called bop gene encodes the light-driven protein pump bacteriorhodopsin (BR) in *H. halobium*.

There has been some reported research on expression of endogenous polypeptides in halobacteria (7, 8 and 9).

SUMMARY OF THE INVENTION

The present invention is directed to the preparation and use of an expression system for heterologous polypeptide production in a halobacterial host.

In a first aspect, such systems in their broadest context would include transcription and translation regulatory DNA, DNA encoding a heterologous polypeptide that is not endogenous to the halobacterial host and DNA encoding transcription and translation stop signals.

Preferably such systems would include DNA encoding the pre-sequence of bacteriorhodopsin such that the polypeptide which is expressed is attached to the pre-sequence, thus allowing the heterologous polypeptide to be properly targeted to the membrane and either inserted into or secreted across the membrane.

Yet another preferred embodiment of the present invention uses the transcription and translation regulatory sequences and the translation and transcription stop sequences of the bacteriorhodopsin gene, either in the presence or absence of the bacteriorhodopsin pre-sequence. The use of the regulatory and stop sequences of the bacteriorhodopsin gene serves to allow high level expression of the heterologous polypeptide sequence.

In a second aspect, the present invention is also directed to utilizing the C-terminal domain of the bacteriorhodopsin polypeptide in order to enhance the separation of the mature heterologous polypeptide from the membrane of the halobacterial host following expression. In a preferred embodiment of this aspect, DNA encoding a unique protease site is introduced between said C-terminal sequence and the DNA encoding the heterologous polypeptide.

In a preferred embodiment of this aspect, high levels of expression of the heterologous polypeptide linked to the C-terminal region of bacteriorhodopsin are achieved by using DNA encoding the transcription and translation regulatory and stop sequences of the bacteriorhodopsin gene.

A further preferred embodiment of the invention is directed to the use of the bacteriorhodopsin pre-sequence to enhance expression of the heterologous polypeptide linked to the C-terminal region of bacteriorhodopsin.

The invention is directed to such systems in all their equivalent aspects, including expression vectors, halobacterial hosts transformed with such vectors and methods for producing, isolating and optionally further purifying heterologous polypeptides using such expression vectors.

DETAILED DESCRIPTION

The present invention has been described herein by disclosing the preferred embodiments and best mode. It will be understood, however, that having detailed the method first used by the present inventors to produce the heterologous polypeptide expression system in halobacterium, it will be apparent to those skilled in the art that one could make modifications within the general skill of the art to produce expression systems that differ in one or more ways from that originally described.

BRIEF DESCRIPTION OF THE DRAWINGS

FIG. 2 shows the nucleic acid sequence (SEQ ID NO:1) of the PstI/BamHI construct of FIG. 1 containing the bacteriorhodopsin gene and about 400 bp of upstream sequences from *Halobacterium halobium* strain R1. Also shown is the amino acid sequence (SEQ ID NO:2) of the BR protein translation product.

Figure 4A:
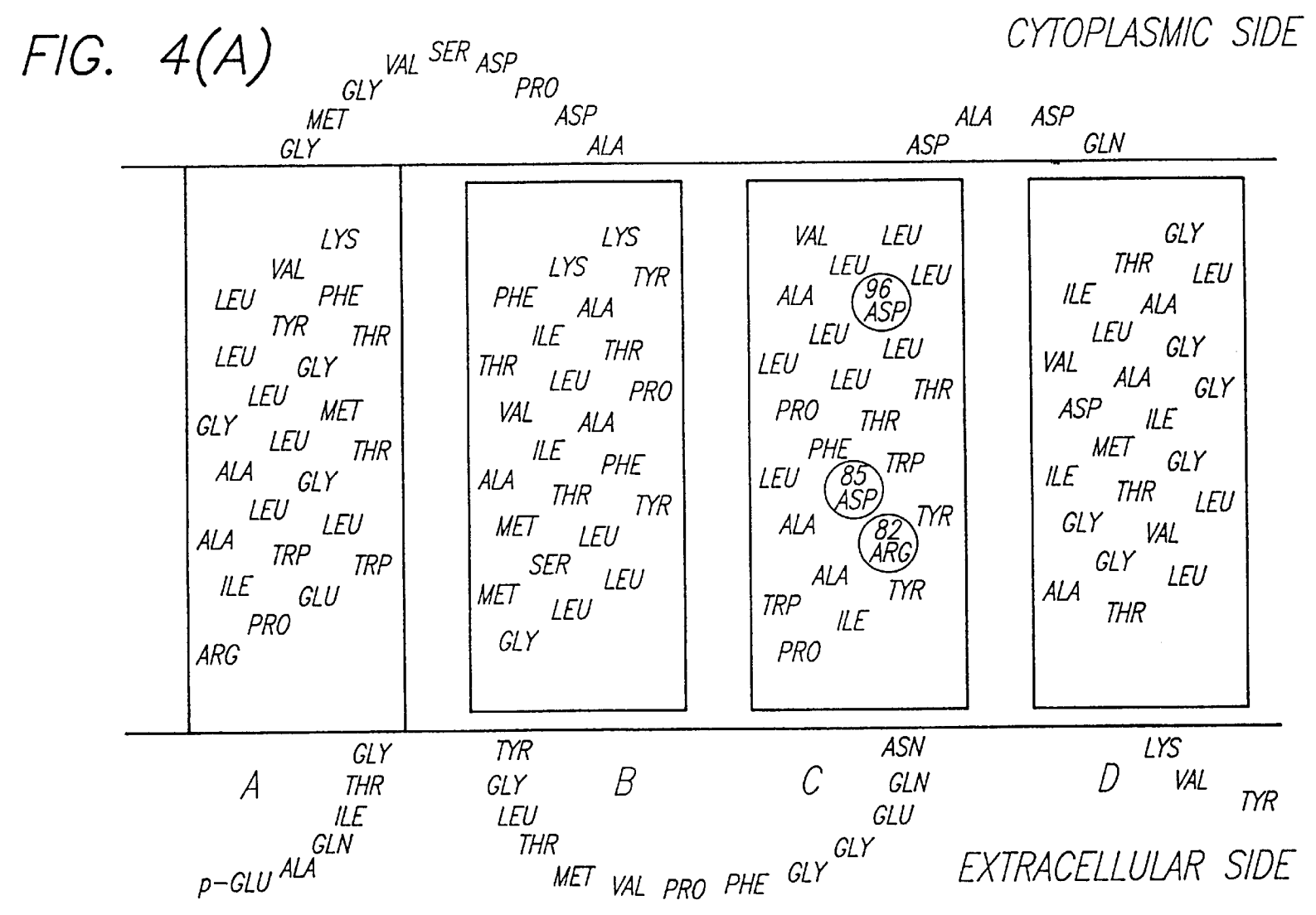

FIG. 4 is a map of the secondary structure of the mature BR protein (SEQ ID NO:3).

FIG. 6 shows the nucleic acid sequence (SEQ ID NO:6) of the PstI/BamHI fragment of FIG. 5 containing the gene for human muscarinic acetylcholine receptor (Type HM1) of pENDS-OM1. Also shown is the amino acid sequence (SEQ ID NO:7) of HM1.

FIG. 8 shows the nucleic acid sequence (SEQ ID NO:8) of the PstI/BamHI fragment of FIG. 7 containing the gene for human muscarinic acetylcholine receptor (Type HM1) which lacks the I3 domain. The amino acid sequence (SEQ ID NO:9) of HM1 having a deleted I3 domain is shown.

FIG. 10 shows the nucleic acid sequence (SEQ ID NO:10) of the PstI/BamHI construct of FIG. 9 containing the rat serotonin receptor gene and the amino acid sequence (SEQ ID NO:11) of the rat serotonin receptor.

FIG. 14 shows the nucleic acid sequence (SEQ ID NO:12) of the PstI/BamHI fragment of FIG. 13 containing the human thrombin receptor gene and the amino acid sequence (SEQ ID NO:13) of the human thrombin receptor.

FIG. 17 shows the nucleic acid sequence (SEQ ID NO:14) of the PstI/BamHI fragment of FIG. 16 containing the bacterio-opsin and the *E. coli* aspartate transcarbamylase genes and the amino acid sequence (SEQ ID NO:15) of the BR/*E. coi* aspartate transcarbamylase fusion protein.

DEFINITIONS

Figure 1:
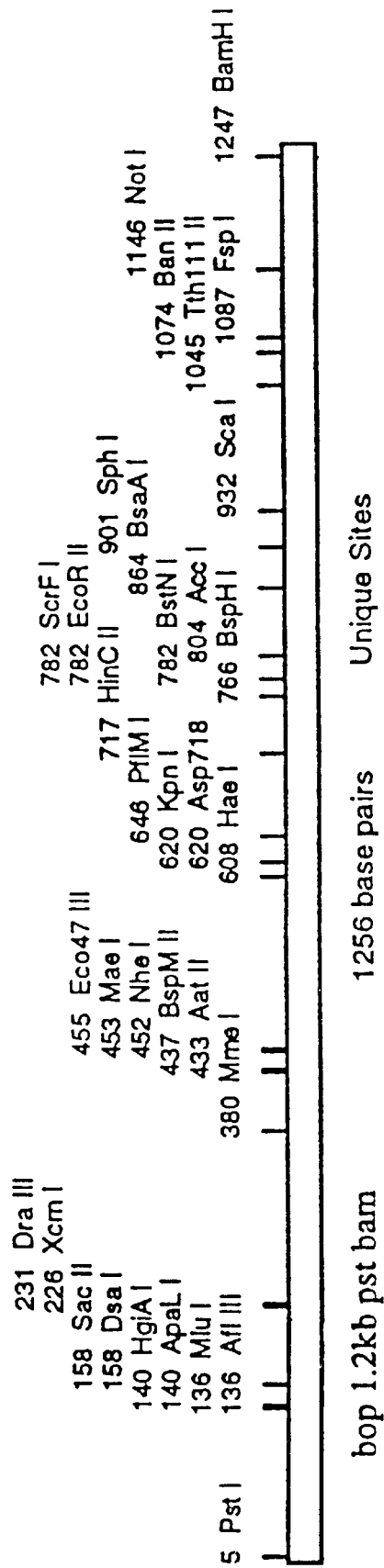
FIG. 1 is a restriction map of the PstI/BamHI fragment containing the bacteriorhodopsin gene and about 400 bp of upstream sequences from *Halobacterium halobium* strain R1.

The term "expression vector" herein has a functional definition and includes vectors capable of expressing DNA sequences contained therein, where such sequences are operably linked to other sequences capable of effecting their expression. In the present specification, "vector" and "plasmid" are used interchangeably as the plasmid is the most commonly used form of vector. However, the invention is intended to include such other forms of expression vectors capable of equivalent functions and which are or become known in the art.

By the term "operable" herein, and grammatical equivalents, is meant that the respective DNA sequences are operational and work for their intended purposes.

The term "heterologous polypeptide" herein refers to presently known or unknown polypeptides not endogenous to the host cell, or if endogenous to the host cell, are obtainable herein in amounts not achievable in native state. Included within the definition are the halobacterial non-retinal binding proteins. Examples of heterologous polypeptides include, but are not restricted to, polypeptides from eukaryotes, eubacteria, archaebacteria, synthetic polypeptides and polypeptides containing bioequivalent amino acid analogs. Further included are other members of the 7-transmembrane crossing family such as muscarinic acetylcholine receptor, serotonin receptor, thrombin receptor, 6-adrenergic receptor, and the like. Heterologous polypeptides also include membrane proteins, for example, cystic fibrosis transmembrane conductance regulator, and soluble proteins, such as various enzymes (e.g. proteases and aspartate transcarbamylase). Each is used in accord with their known or determined function biologically and is adapted for such in accord with procedures generally known in the art.

By the term "DNA encoding heterologous polypeptide" is meant a DNA sequence coding for a polypeptide that is not endogenous to the host wherein it is expressed. Because of the high GC content (i.e. about 58–68%) of the genome of halobacteria, it is preferred that the DNA sequence encoding the heterologous polypeptide be in this range, although sequences with higher and lower GC content than that usually found in halobacteria can be used. For example, we have been successful in expressing *Escherichia coli* aspartate transcarbamylase, having a GC content of about 50%, as a fusion protein to the C-terminus of BR.

The term "transcription and translation regulatory DNA" and equivalents, in its broadest sense refers to a DNA sequence responsible for the dual transcription and translation elements of expression. In a preferred embodiment the regulatory DNA is that of the bacteriorhodopsin gene (from −364 to +41 relative to the RNA start site, FIG. 2 (SEQ ID NO:1)).

In an alternative embodiment, the regulatory DNA contains about 4000 bp of sequences (from about −4000 to +41) upstream of the bop gene and includes three other genes of the bop gene cluster, which include brp (13), bat (14) and blp (Gropp & Betlach, manuscript in preparation). Some or all of these genes may be regulatory genes.

By the term "transcription and translation stop signals" and equivalents, in its broadest scope is meant DNA which functions to terminate transcription and translation, respectively. It is preferred that the transcription and translation stop signals be those of the bacteriorhodopsin gene.

By the term "pre-sequence of bacteriorhodopsin gene" herein is meant a sequence of about 13 amino acids required to target bacteriorhodopsin to the membrane. The 13 amino acid pre-sequence is encoded by nucleotides +3 to +41 relative to the RNA start site depicted in FIG. 2 (SEQ ID NO:1).

By the term "halobacterium host" is meant strains belonging to Halobacterium including species of extreme and moderate halophiles having a wild-type genotype. Examples of the extreme halophilic species having a wild type genotype include *Halobacterium saccharovorium* (ATCC 29252), *Halobacterium california* (ATCC 38799), *Halobacterium halobium* (CCM 2090) and *Halobacterium valismortis* (ATCC 29-715). Wild type moderate halophiles are exemplified by the species *Halobacterium mediterannei* (ATCC 33500). It may be preferred that the halobacterial host species is bacteriorhodopsin deficient. Bacteriorhodopsin deficient species are either wild-type, such as *H. volcanii*, or mutants, such as L33 (15), S9F1x3 (16), IV-8 (17) and IV-14 (17). Bacteriorhodopsin deficient mutants derived from strains which express purple membrane constitutively, such as 133, or inducibly, are useful for different applications. Depending on the nature of the upstream regulatory regions in the expression vector construct, inducible strains permit regulated expression whereas constitutive strains do not.

The term "restriction site" herein refers to a DNA sequence recognizable by an endonuclease as a site of DNA cleavage.

By the term "C-terminal sequence", "C-terminal region" and equivalents, is meant the polypeptide sequence at the C-terminus of bacteriorhodopsin; See FIG. 4.

By the term "unique protease site" is meant an amino acid sequence recognizable by a protease as the site of cleavage of the polypeptide wherein it is disposed and which is absent from the heterologous polypeptide expression product. In a preferred embodiment, the protease site (Ile-Glu-Gly-Arg) (SEQ ID NO:4) of factor $X_a$ is used in view of the rarity of this sequence.

EXAMPLES

1. Cloning the DNA sequence encoding the heterologous polypeptide into a halobacterial expression vector i. Constructs for express ion of membrane proteins All constructions are assembled using standard molecular techniques (12) including PCR. Expression vectors can be prepared in a variety of conventional ways. Although others may be used, a preferred halobacterial cloning vector to be adapted into an express ion vector is plasmid pUBP2 (FIG. 3) described by Blaseio et al. (7). The plasmid may be isolated using conventional techniques. For example, the plasmid may be purified using caesium chloride-ethidium bromide density gradients, electrophoresis from an agarose gel onto a dialysis membrane, use of commercially available chromatography columns for the separation of plasmids, such as magic minipreps DNA purification system (Promega Corp., Madison, Wis.), etc.

Figure 3:
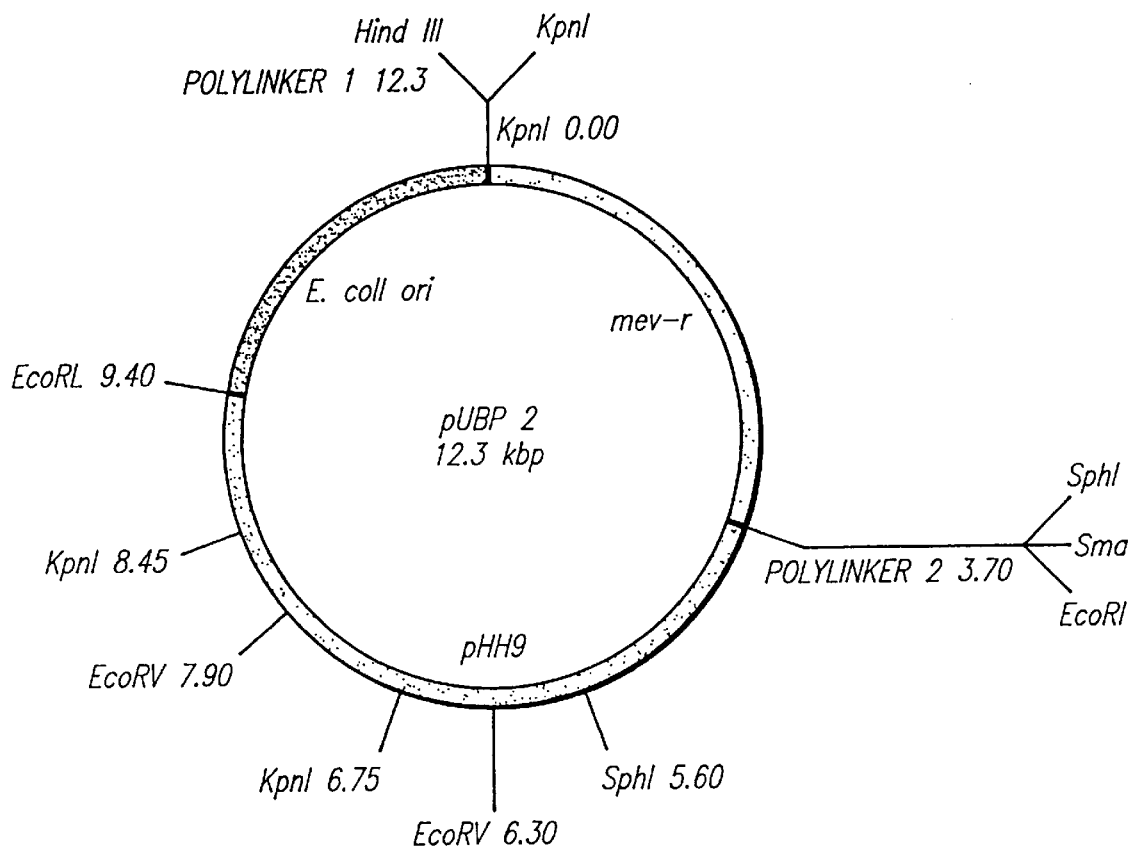
FIG. 3 shows the restriction map of pUBP2.

The expression vectors which will be employed will normally include a marker which allows for selection of cells into which the DNA has been integrated, as against cells which have not integrated the DNA construct. An example of commonly used selection markers is antibiotic resistance. Two markers are available for selection of halobacteria, including resistance to novobiocin (8) and mevinolin (7). It is preferred that the marker used be that for mevinolin resistance; mevinolin is a HMG CoA reductase inhibitor (7). This marker is present in the preferred cloning plasmid pUBP2 (FIG. 3).

To convenience insertion of DNA sequences, plasmids will contain polylinker sequences containing various restriction sites. Several examples of polylinkers are known and available (12). A typical polylinker is polylinker 1 (123) (FIG. 3) which contains restriction sites for HindIII, SphI MluI, XhoI PstI, SalI, XbaI, BamHI, HindIII, XbaI and KpnI. Another typical polylinker is polylinker 2 (3.70) (FIG. 3) with restriction sites for SphI, EcoR5, SstI, SmaI and EcoRI.

The DNA sequence encoding the heterologous polypeptide is inserted such that it is placed downstream from a transcription and translation regulatory region containing a promoter and a ribosome binding site using standard techniques. It is preferred that the promoter used is inducible, allowing controlled expression of the heterologous polypeptide product. In a preferred embodiment of the invention, the transcription and translation regulatory sequences of the bacteriorhodopsin gene will be used. The bacteriorhodopsin gene may be isolated from the genome of halobacteria using appropriate restriction enzymes. Transcription and translation regulatory sequences of the bacteriorhodopsin gene are located in the region of −365 to +41 relative to the RNA start site of the bacteriorhodopsin sequence depicted in FIG. 2 (SEQ ID NO:1).

To effect appropriate termination of heterologous polypeptide synthesis, DNA sequences encoding transcription and translation stop signals are placed downstream of the inserted DNA sequence encoding the heterologous polypeptide sequence using well known techniques (12). Preferably, the sequences downstream of the bacteriorhodopsin gene (FIG. 2) (SEQ ID NO:1) which includes the translational stop codon (TGA) followed by ~80 bp which include the transcriptional termination signal are employed as stop signals.

Where it is advantageous to produce a heterologous transmembrane polypeptide which is targeted to the halobacterial membrane, DNA encoding the heterologous polypeptide is ligated downstream of DNA encoding the pre-sequence of BR.

The heterologous gene of interest may be cloned into the *E. coli* plasmid, pUC19 (20), along with BR regulatory sequences such that all cloned sequences will reside on a DNA fragment containing two unique restriction sites (choice of PstI, BamHI, SmaI). More specifically, the heterologous gene is ligated such that it is in frame with the BR pre-sequence, downstream of the bacteriorhodopsin regulatory sequences/promoter and upstream of the bacteriorhodopsin transcriptional and translational termination sequences. A specific unique protease site may be engineered into some constructions between the BR pre-sequence and the heterologous gene.

Figure 15A:
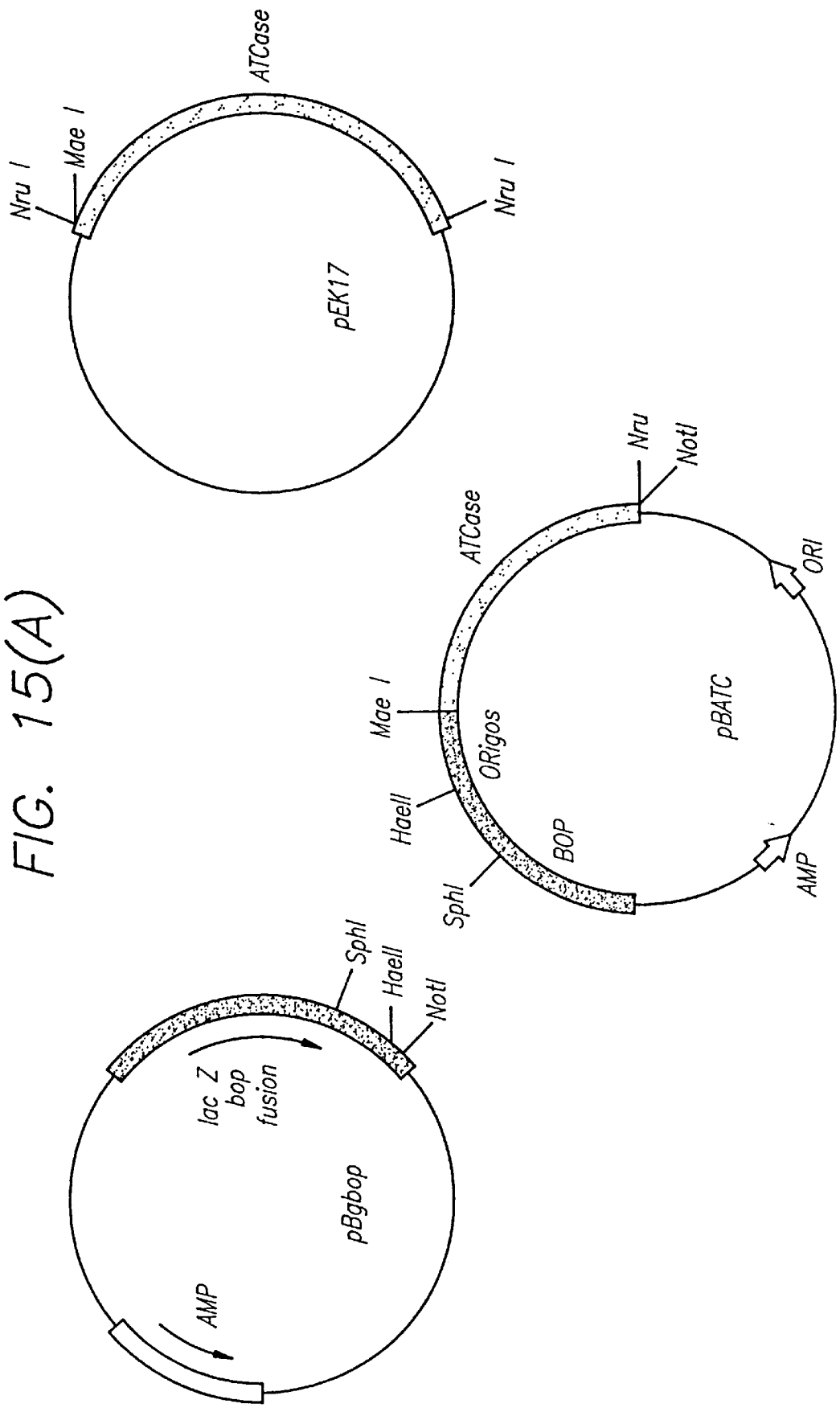
FIG. 15 shows the restriction maps of pβgbop, pEK17, pBATC, p1.2KbBop and pBRAT.
Figure 15B:
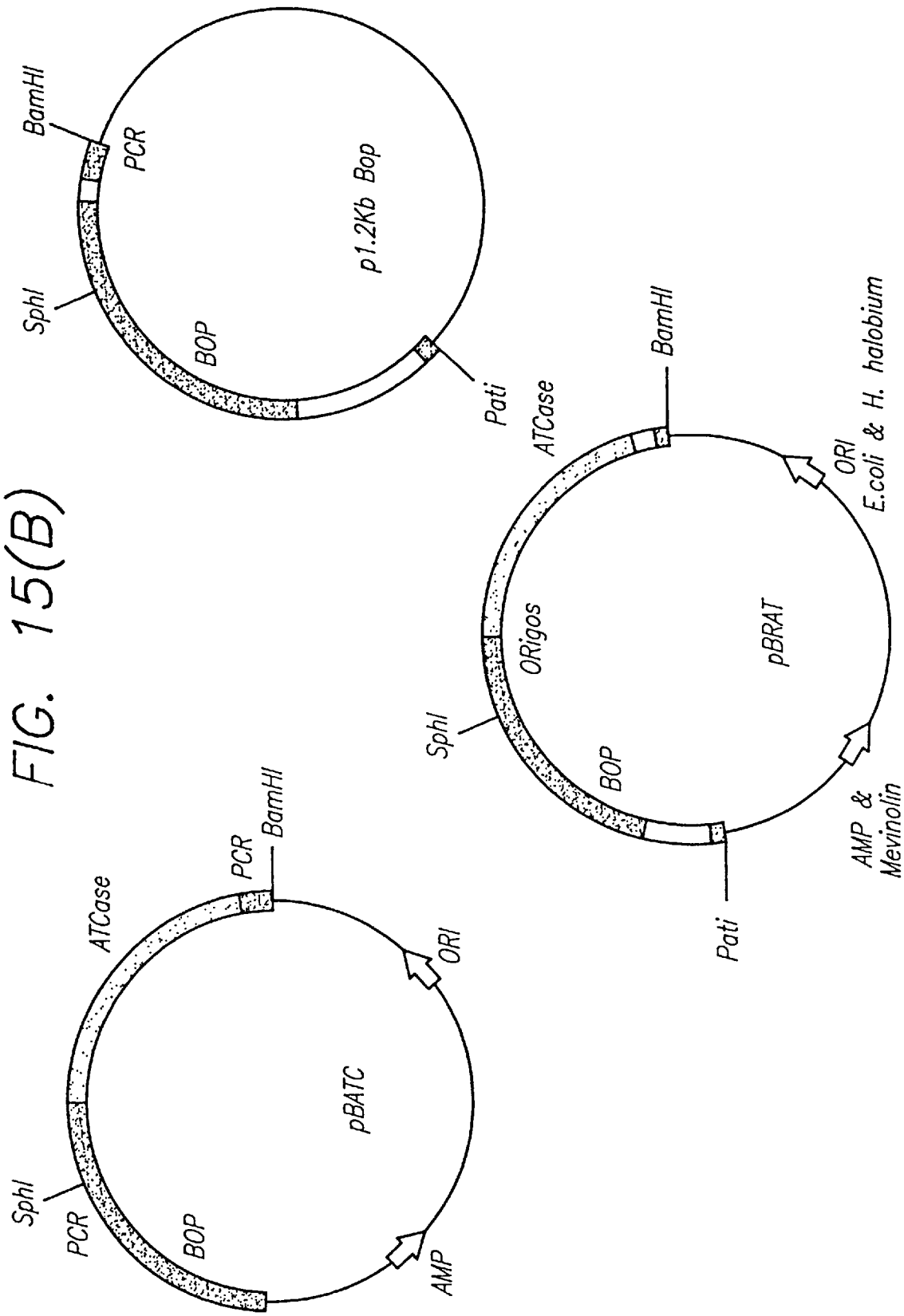

A 1.2 kbp fragment containing the bop gene and ~370 bp of upstream sequences was isolated from *H. halobium* strain R1 DNA using PCR and cloned into the PstI/BamHI sites of pUC19 (denoted p1.2Kbbop) (FIG. 15B). Two endogenous AlwNI sites were removed from the cloned 1.2 kbp fragment: i) one site located 165 bp upstream of the bop gene start codon (SEQ ID NO:1) was removed by generating a G→T point mutation using the Kunkel method (29), and ii) the second AlwNI site located 7 bp upstream of the bop gene stop codon was removed using the Transformer Site-Directed Mutagenesis kit (Clontech Laboratories, Inc., Palo Alto, Calif.). Subsequently, a ~400 bp PstI/AlwNI fragment (denoted "bop 5' fragment") containing the bop upstream sequences, DNA encoding the BR presequence and the first four (extrahelical) residues of BR was isolated by PCR from the mutated 1.2 kbp fragment. Concurrently, a ~100 bp NotI/BamHI fragment (denoted "bop 3' fragment") containing DNA encoding six C-terminal residues of BR, the BR stop codon and the transcriptional termination sequences of BR (up to 44 bp downstream of the stop codon) was obtained from the 1.2 kbp bop gene fragment by preparative digestion and purification (Prep-A-Gene, BioRad, Richmond, Calif.). In addition, an endogenous AlwNI site located in pUC19 (position 1217) was removed using the Clontech Transformer kit and the mutated pUC19 was preparatively digested with PstI/BamHI and preparatively purified (denoted "vector fragment"). The three fragments (i.e., "bop 5' fragment", "bop 3' fragment" and "vector fragment") were ligated with DNA fragments containing various heterologous genes engineered to be in frame with the BR presequence and extrahelical residues and to contain a single AlwNI site at the 5' terminus of the fragment and a single NotI site at the 3' terminus of the fragment as described below. In all of the heterologous genes, endogenous AlwNI, NotI, BamHI and PstI sites were first removed (if necessary) to facilitate the construction. Once the heterologous gene was cloned along with the BR 5' and 3' regulatory sequences into pUC19, this intermediate construct (denoted "pENDs") was preparatively digested with PstI/BamHI Subsequently, the PstI/BamHI restriction fragment containing the heterologous gene with the regulatory sequences of BR was preparatively isolated away from pUC19 sequences by agarose gel electrophoresis, purified using Prep-A-Gene (Bio-Rad, Richmond, Calif.) and cloned into the *E. coli/H. halobium* shuttle vector, pUBP2 (7). pUBP2 carries the pBR322 replicon and ampicillin resistance marker, the halobacterial plasmid pHH1 origin of replication and a mevinolin resistance marker. Mevinolin resistance is encoded by an up-promoter mutation of the HMG-CoA reductase gene.

The construction was verified by restriction mapping and nucleotide sequencing across the junctions between 5' and 3' BR regulatory sequences and the heterologous gene.

a. Human muscarinic acetylcholine receptor (Type HM1)

Figure 5:
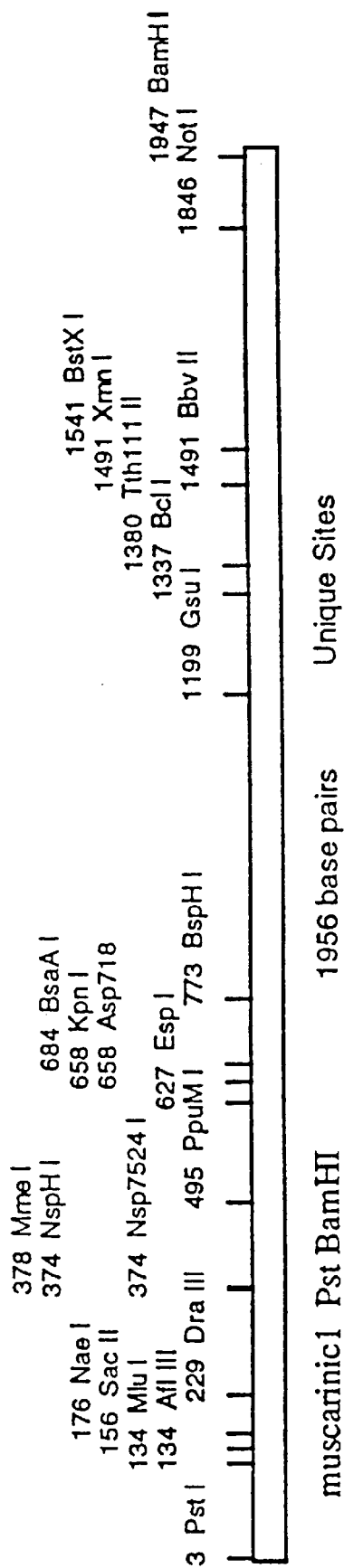
FIG. 5 is a restriction map of the PstI/BamHI fragment containing BR regulatory sequences and the gene for human muscarinic acetylcholine receptor (Type HM1) in pENDS-OM1.
Figure 7:
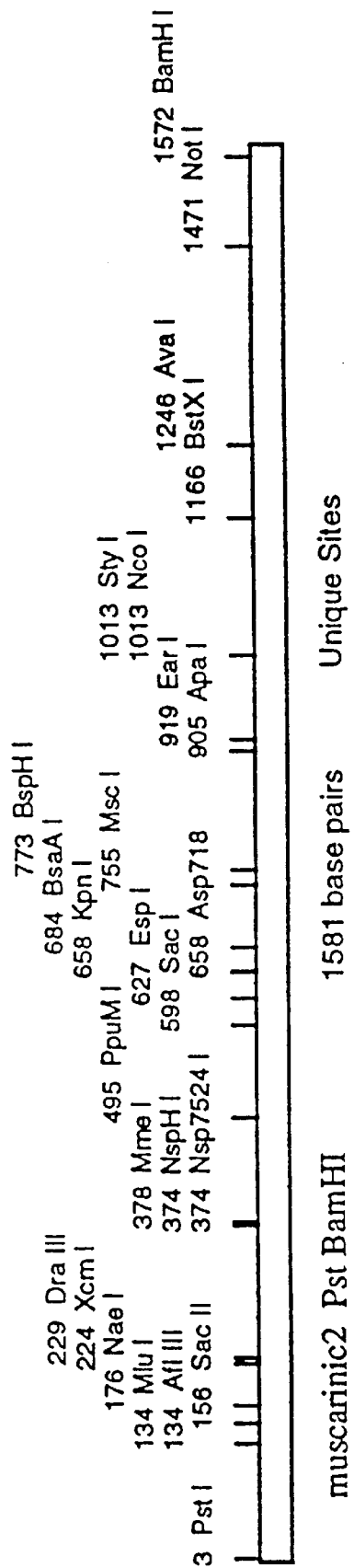
FIG. 7 is a restriction map of the PstI/BamHI fragment containing the BR regulatory sequences and gene for human muscarinic acetylcholine receptor (Type HM1) in pENDS-OM2.

Two different constructs were made with this gene. The first (denoted pENDs-OM1) contained the entire gene whereas the second (denoted pENDs-OM2) lacked the large internal cytoplasmic loop (i.e., I3) which is thought to be involved in signaling. Prior to the generation of the constructions described below, two endogenous AlwNI sites and one endogenous PstI site were removed from human muscarinic acetylcholine receptor (denoted HM1) cloned in pGEM3 (Promega Corp, Madison, Wis.) using either the Clontech Transformer kit or the Kunkel method (29). The positions of the removed sites are shown in FIG. 6 (SEQ ID NO:6).

pENDs-OM1 was generated as follows. First, the HM1 gene was isolated by PCR from pGEM3/HM1 so as to contain an AlwNI site at the 5' terminus and a Not I site the 3' terminus of the PCR fragment. This PCR fragment was ligated to the "bop 5' fragment", "bop 3' fragment" and "vector fragment" described above and transformed into *E. coli*. The resultant plasmid was named pENDs-OM1. pENDs-OM1 contains the methionine start codon of HM1 located 4 codons downstream from the BR 5' sequences. Nine extra base pairs generated by introduction of the AlwNI site encode 3 extra residues (i.e., gln, ala, leu) located in frame between the BR 5' sequences and the start codon of the HM1 gene. At the 3' terminus of the gene, the HM1 stop codon precedes the BR stop codon by 48 bp. From pENDs-OM1, the BR regulatory sequences with the HM1 gene were transferred to pUBP2 on a PstI/BamHI fragment (FIG. 5 and FIG. 6, SEQ ID NO:6) as described above.

pENDs-OM2 was generated in a similar manner as its sibling construct. First, however, deletions of the I3 domain were introduced after digestion of the HM1 gene at the unique StuI restriction site (position 712 relative to the start codon of the HM1 gene, SEQ ID NO:6), followed by digestion with the exonuclease Bal-31 for varying times at 4° C. The blunt-ended product was self-ligated to yield mutants with deletions of varying size within the I3 domain. One of these was chosen for further study which lacked amino acid residues 231 through 357 of HM1 (SEQ ID NO:7). DNA from this mutant was used to generate a PCR fragment containing the HM1 gene (less I3 loop) with a 5' AlwNI site and a 3' Not I site. This PCR fragment was identical to the fragment described above except for the lack of the I3 loop and was used to generate pENDs-OM2 in a similar manner to the pENDs-OM1 construct. The sequence of the PstI/BamHI fragment containing the BR regulatory sequences and the HM1 gene (less I3 loop) is shown in FIG. 8 (SEQ ID NO:8).

b. Rat serotonin receptor (Type 1 C)

Figure 9:
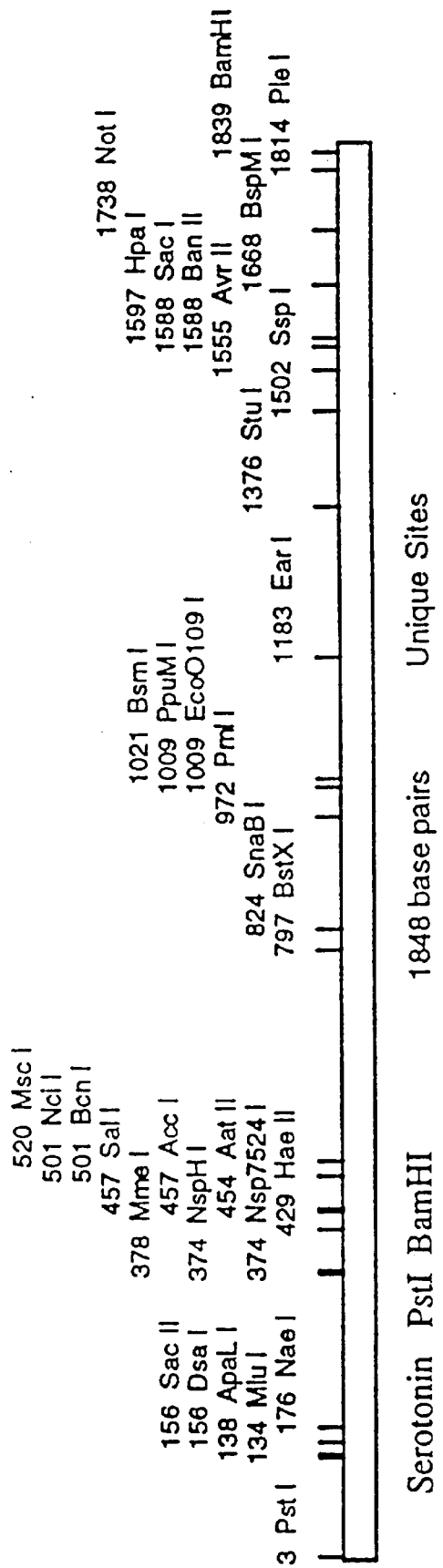
FIG. 9 is a restriction map of the PstI/BamHI fragment containing the BR regulatory sequences and the rat serotonin receptor (Type 1C) gene.

The rat serotonin receptor gene (denoted "Ser") cloned as a 3 Kb EcoRI cDNA fragment on the plasmid pSR1c (27) was used as a basis for the following constructions. The Ser gene contains no endogenous AlwNI, NotI, BamHI and PstI sites and was adapted for expression in *H. halobium* as follows. AlwNI and NotI cloning sites were introduced within the 5' coding and 3' noncoding regions of the Ser gene, respectively. In addition, DNA encoding a polyaspartic acid peptide was placed in frame upstream of the Ser gene and downstream of the AlwNI site. Translation of this sequence generates a peptide epitope useful for subsequent detection of expressed protein (31). This fragment was isolated and ligated to the "bop 5' fragment", "bop 3' fragment", and "vector fragment" described above and transformed into *E. coli*. The resultant plasmid was named pENDs-Ser and contains the 36th codon of the rat serotonin receptor gene preceded by DNA encoding the peptide epitope and BR 5 ' sequences. Nine extra base pairs generated by the construction and encoding 3 extra residues (i.e., gln, ala, leu) are located in frame between the BR 5' sequences and the epitope sequences. At the 3' terminus of the gene, the Ser stop codon precedes the BR stop codon by 18 bp. Following the construction of pENDs-Ser, the BR regulatory sequences with the Ser gene were transferred to pUBP2 on a PstI/BamHI fragment (FIG. 9 and FIG. 10, SEQ ID NO:10).

c. Human thrombin receptor

A clone of the human thrombin receptor gene (denoted "Thromb") (33) was used as a basis for the following constructions. Four endogenous DNA restriction sites were removed from the gene using the Kunkel method (29). These included three AlwNI sites (291, 945, and 1038) and one PstI site (537). Positions are given relative to the first base of the start codon of the gene. "pENDs-Thromb" was generated as follows. An AlwNI/NotI fragment containing the gene was generated using oligonucleotide-directed-insertion-mutagenesis and PCR. Included on this fragment were additional nucleotide sequences encoding short peptides for use in the detection and purification of the expressed protein. The AlwNI/NotI fragment containing the gene along with epitope encoding sequences was ligated to the "bop 5' fragment", "bop 3' fragment" and "vector fragment" described above and transformed into E. coli. The resultant plasmid was named pENDs-Thromb. In pENDs-Thromb, thirty-three extra base pairs generated by the construction and encoding eleven extra amino acids are located in frame between the BR 5' sequences and the Thromb sequences. Twenty seven of the extra residues encode a poly-aspartic acid peptide sequence which when translated generates a peptide epitope useful for detection of expressed protein (31). At the 3' terminus of the gene, six histidine codons have been inserted upstream of the Thromb stop codon. These histidine codons are intended to aid in the affinity purification of expressed protein (26). At the 3' terminus of the gene, the Thromb stop codon precedes the BR stop codon by 18 bp.

Figure 13:
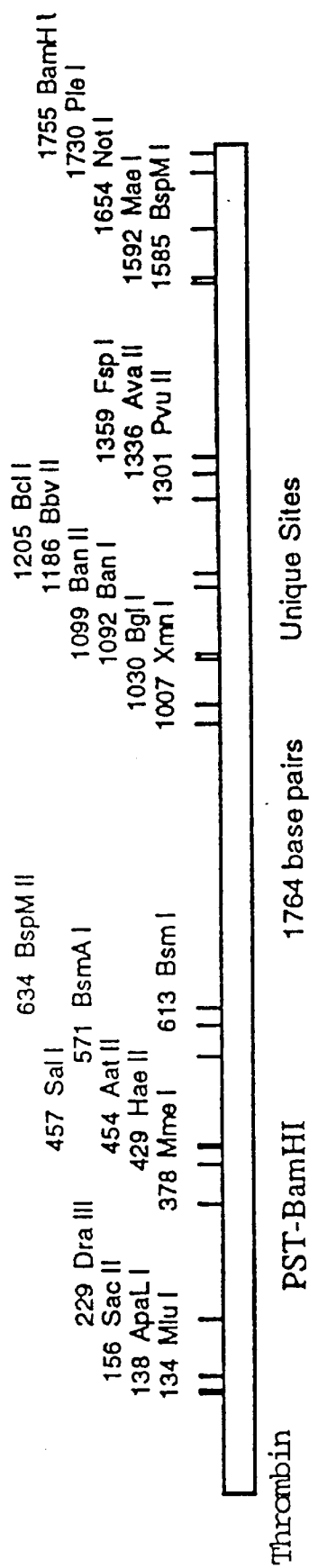
FIG. 13 is a restriction map of the PstI/BamHI fragment containing BR regulatory sequences and the human thrombin receptor gene.

The BR regulatory sequences with the human thrombin receptor gene may be transferred into pUBP2 on a PstI/BamHI fragment (FIG. 13 and FIG. 14, SEQ ID NO:12) as described above.

ii. Constructs for expression of soluble proteins

Where it is desired that heterologous soluble polypeptide be released extracellularly into the culture medium following expression, the DNA sequence encoding the heterologous polypeptide may be ligated to DNA encoding the pre-sequence of bacteriorhodopsin (FIG. 2 (SEQ ID NO:1), from +3 to +41 relative to the RNA start site) using techniques well known to those skilled in the art (12).

Where it is advantageous to produce a heterologous soluble polypeptide that is targeted, following expression, to the halobacterial membrane, DNA encoding the heterologous polypeptide is ligated downstream of the DNA encoding the C-terminal region (FIG. 2 and FIG. 4 (SEQ ID NOs:1 and 3)) of bacteriorhodopsin or to fragments thereof.

To facilitate subsequent purification of the heterologous polypeptide product, a DNA sequence encoding a unique protease site is engineered between DNA encoding the bacteriorhodopsin C-terminal region and DNA encoding the heterologous polypeptide. Sequences encoding unique protease cleavage sites are known and include, for example, subtilisin, thrombin, enterolinase, and factor $X_a$. In a preferred embodiment, a DNA sequence encoding the amino acid sequence Ile-Glu-Gly-Arg (SEQ ID NO:4) is used to encode a unique protease site which is recognized by Factor $X_a$.

Design of the soluble protein expression vector and methods used are similar to that described above for membrane proteins. However, soluble proteins are expressed as in-frame fusions to the C-terminal region of BR. Thus, these fusion proteins will have membranous domain (i.e. BR or portions thereof) and a soluble domain (i.e. heterologous polypeptide). The heterologous gene is cloned at the C-terminus of BR, between the bacteriorhodopsin gene and the downstream transcriptional/translational termination sequences of BR. In addition, a unique protease site is engineered between BR and the heterologous gene to facilitate subsequent purification of the protein. The final construct is cloned into the E. coli/H. halobium shuttle vector, pUBP2 (7).

a. E coli Aspartate Transcarbamylase (catalytic subunit)

The catalytic subunit of Aspartate Transcarbamylase, (denoted ATCase), a soluble protein, has been fused to the C-terminus of BR as follows. The bop gene containing plasmid, pβgbop (32), was digested at the unique NotI site located near the 3' terminus of the bop gene (see FIG. 15A). Subsequently, this NotI site was filled-in to create a blunt site (12). The resulting DNA was digested with SphI to generate two fragments, a large fragment (denoted fragment 1) containing the vector along with the N-terminus of the bop gene and a small fragment containing internal bop gene sequences. Fragment 1 was isolated and purified. A second aliquot of pβgbop was digested with SphI/HaeII and a 217 bp fragment (denoted fragment 2) containing an internal portion of the bop gene was isolated and purified (FIG. 15A).

The structural gene for the E. coli catalytic subunit of aspartate transcarbamylase was isolated from pEK17 (FIG. 15A) (30). A 845 bp MseI/NruI fragment (denoted fragment 3) which contains all but the first 18 bp of the gene encoding ATCase was isolated and purified.

A synthetic fragment of DNA (denoted fragment 4) was constructed by annealing two complementary oligonucleotides and used to connect the bop and ATCase genes. The synthetic fragment was engineered to contain a HaeII site at the 5' terminus, a MseI site at the 3' terminus and an internal NruI site. Also included were nucleotides encoding: i) a unique protease site (i.e., blood clotting Factor $X_a$) and ii) ATCase amino acids 6 and 7 (relative to ATCase start codon) FIG. 17, SEQ ID NO:14.

All four DNA fragments were ligated together and used to transform E. coli strain D1210 (28) with selection for ampicillin resistance. Positive clones were identified by colony filter hybridization using $P^{32}$ radiolabeled random primed (25) ATCase MseI/NruI fragment as probe. Positive clones were verified by restriction mapping and nucleotide sequencing. One positive clone was chosen and denoted pBATC (FIG. 15A).

Subsequently, the bop-ATCase fusion construct was adapted for H. halobium expression as follows. A fragment spanning the sequences in between and including the internal SphI site of the bop gene at the 5' terminus and the ATCase translational stop codon at the 3' terminus was isolated from pBATC by PCR (see FIG. 15B). In addition, the oligonucleotide used to construct the 3' terminus of this PCR fragment was designed to be complementary to bop sequences downstream of the transcriptional termination sequences and to include a unique BamHI to facilitate subsequent cloning steps. The resultant PCR fragment was digested with SphI/BamHI, purified and used in the following construction.

Figure 16:
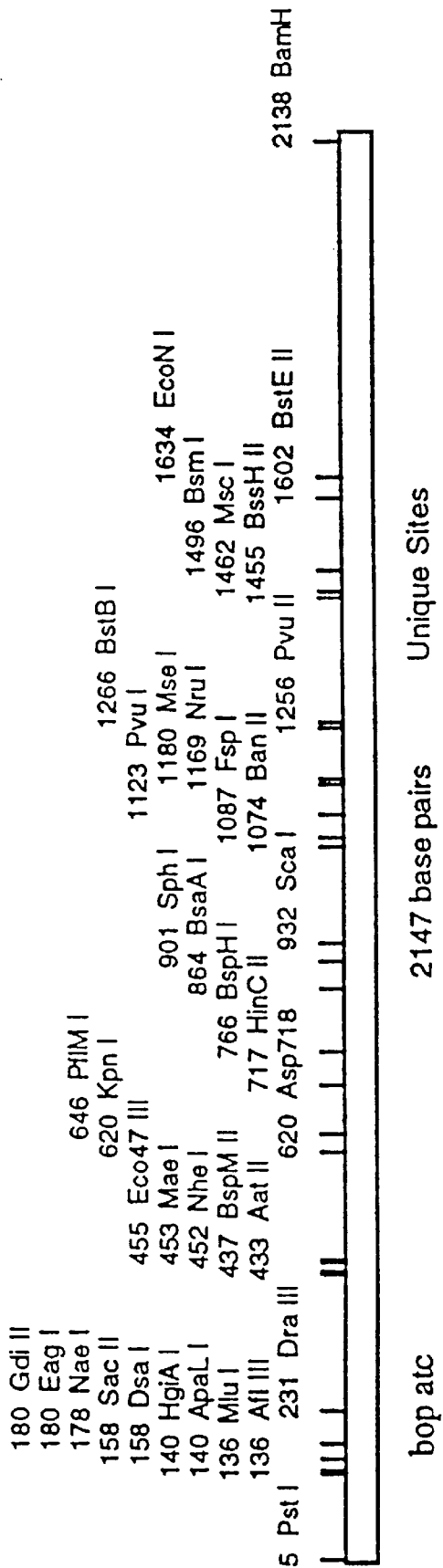
FIG. 16 shows a restriction map of the PstI/BamHI fragment containing BR regulatory sequences, the bacterio-opsin gene and the gene encoding the *Escherichia coli* catalytic subunit of aspartate transcarbamylase.

The plasmid, p1.2Kbbop, containing the bop gene and upstream sequences cloned in pUC19 (described above) was digested with SphI/BamHI to yield two fragments, a large one containing the vector and the majority of the bop gene, and a 358 bp fragment containing the C-terminal half of the bop gene (FIG. 15B). The larger of these two fragments was isolated, purified and ligated to the SphI/BamHI bop-ATCase PCR fragment A positive clone was isolated and confirmed by restriction mapping and nucleotide sequencing. This clone was digested with PstI/BamHI and a fragment containing DNA encoding the BR/ATCase fusion along with bop upstream regulatory sequences (FIG. 16) was cloned into the E. coli/H. halobium shuttle vector pUBP2. The resultant construct was named pBRAT (FIG. 15B). The nucleotide sequence (SEQ ID NO:14) and the translated amino acid sequence (SEQ ID NO:15) of this PstI/BamHI fragment is shown in FIG. 17.

2. Transformation of *Halobacterium halobium*

The PstI/BamHI fragments of the pENDs-Ser (FIG. 9 and 10, SEQ ID NO:10) and pBRAT (FIG. 15B, FIG. 16 and FIG. 17, SEQ ID NO:14) constructs containing the heterologous genes with the BR regulatory sequences were isolated and purified. Subsequently, these fragments were cloned into the *E. coli/H. halobium* shuttle vector pUBP2 (7) and transformed into *H. halobium* Bop deficient strain L33 as described (24).

Preferably, plasmids may be introduced into halobacteria using the polyethylene glycol (PEG) method (10, 11). Transformed halobacterial cells are then grown in culture in an appropriate nutrient medium sufficient to maintain the growth of halobacterial cells (7, 8).

*H. halobium* is prone to cell lysis during transformation procedures (7). Since surfactants are known to promote halobacterial lysis (21), all media and glassware used were soap-free. Transformation was performed according to Blaseio (7) and Cline (11) with modifications. Initially, cells were subcultured several times in soap-free complex (YET) medium. Subsequently, cells were subcultured to an $OD_{660}$ of about 0.01 and grown at 40° C. until the early to mid-logarithmic stage of growth ($OD_{660}$ of 0.4 to 0.6). All succeeding manipulations were performed at room temperature. The culture was removed from the waterbath shaker and incubated without agitation for 4 h to overnight, followed by centrifugation of 2 ml of culture at 1000×g for 15 min. The supernatant was carefully removed with a pipette and the interior of the centrifuge tube dried with absorbent tissue. The cell pellet was resuspended in $\frac{1}{10}$ volume of spheroplasting solution (11), followed by addition of $\frac{1}{100}$ volume of 0.5 M EDTA in Spheroplasting solution (11) and incubation for 2 min. One µg of DNA in 10 µl of spheroplasting solution was then added to the spheroplasted cells along with an equal volume of 60% PEG 600 (unrecrystallized) in spheroplasting solution. The combined solutions were gently but thoroughly mixed and then incubated for 20 min. Ten ml of 15% sucrose in complex (YET) medium was added followed by incubation overnight with no agitation at 42° C. The following day, cells were centrifuged at 3000×g for 15 minutes and resuspended in 300 µl of 15% sucrose in complex (YET) medium. This solution was plated on solid complex (YET) selection medium.

3. Analysis of transformants, expression of the heterologous polypeptide and assays for expression To establish that halobacterial cells have been successfully transformed, various techniques may be employed. Where the expression vector used to transform the halobacteria contains a dominant selectable marker, transformed cells can be selected by growing in the appropriate selection medium such that growth of halobacterial cells not harboring the recombinant plasmid is inhibited. For example, where a plasmid containing the mevinolin resistance marker is used, halobacterial cells which harbor this plasmid may be selected by growing on solid nutrient medium containing mevinolin at a concentration in the range of 5 to 25 µM. Further, the plasmid may be isolated using standard techniques (12), restricted and used. The polymerase chain reaction, gel electrophoresis, restriction analysis, Southern, Northern, and Western blots may be employed, sequencing, or the like, may all be employed with advantage.

Depending upon the particular construct and the halobacterial background strain which have been employed for expression of the heterologous polypeptides, one may have constitutive or inducible expression of the heterologous polypeptide product. In the case of constitutive expression, the product will be continuously formed as the cells grow. By contrast, for inducible expression, one may provide for induction when the cells reach a predetermined cell density.

Where inducible promoters have been engineered into the expression vector containing the heterologous polypeptide DNA sequence, transcription may be induced using appropriate inducers under such conditions of concentration and duration as to effect induction of transcription. For example, if the regulatory sequences of the bacteriorhodopsin gene are used, transcription can be induced by low oxygen tension and high light intensity (18, 19) which are known to induce high level expression of BR. Low oxygen tensions are achieved in various ways such as by flushing culture flasks with oxygen-free nitrogen and sealing them, or by permitting cultures to reach the stationary phase of growth in which oxygen limitation occurs naturally (18). High light intensity of greater than about 100 mW/cm$^2$ can be achieved using various light sources and apparati as described (18, 19).

Figure 11:
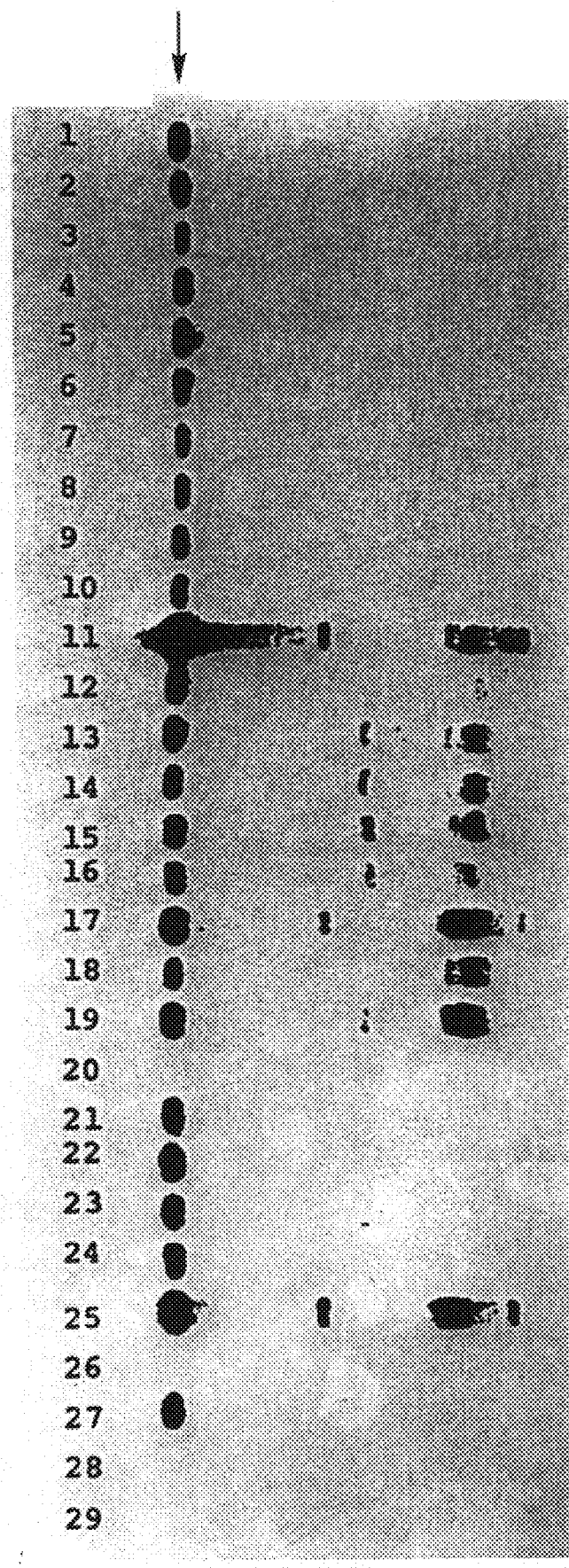
FIG. 11 is a Southern blot of DNA isolated from *H. halobium* Bop deficient strain L33 transformed with pUBP2 containing the rat serotonin receptor (Type 1C) gene. Lanes 1–10, 12–19, 21–24 and 27 contained DNA from strain L33 transformed with pUBP2 containing the PstI/BamHI fragment of FIGS. 9 and 10 (SEQ ID NO:10). Lanes 11 and 25 are positive controls which contained purified plasmid DNA (i.e. pUBP2 containing serotonin receptor gene). Lane 29 contained DNA from strain L33. The arrow indicates the location of the PstI/BamHI fragment corresponding to serotonin DNA.
Figure 12:
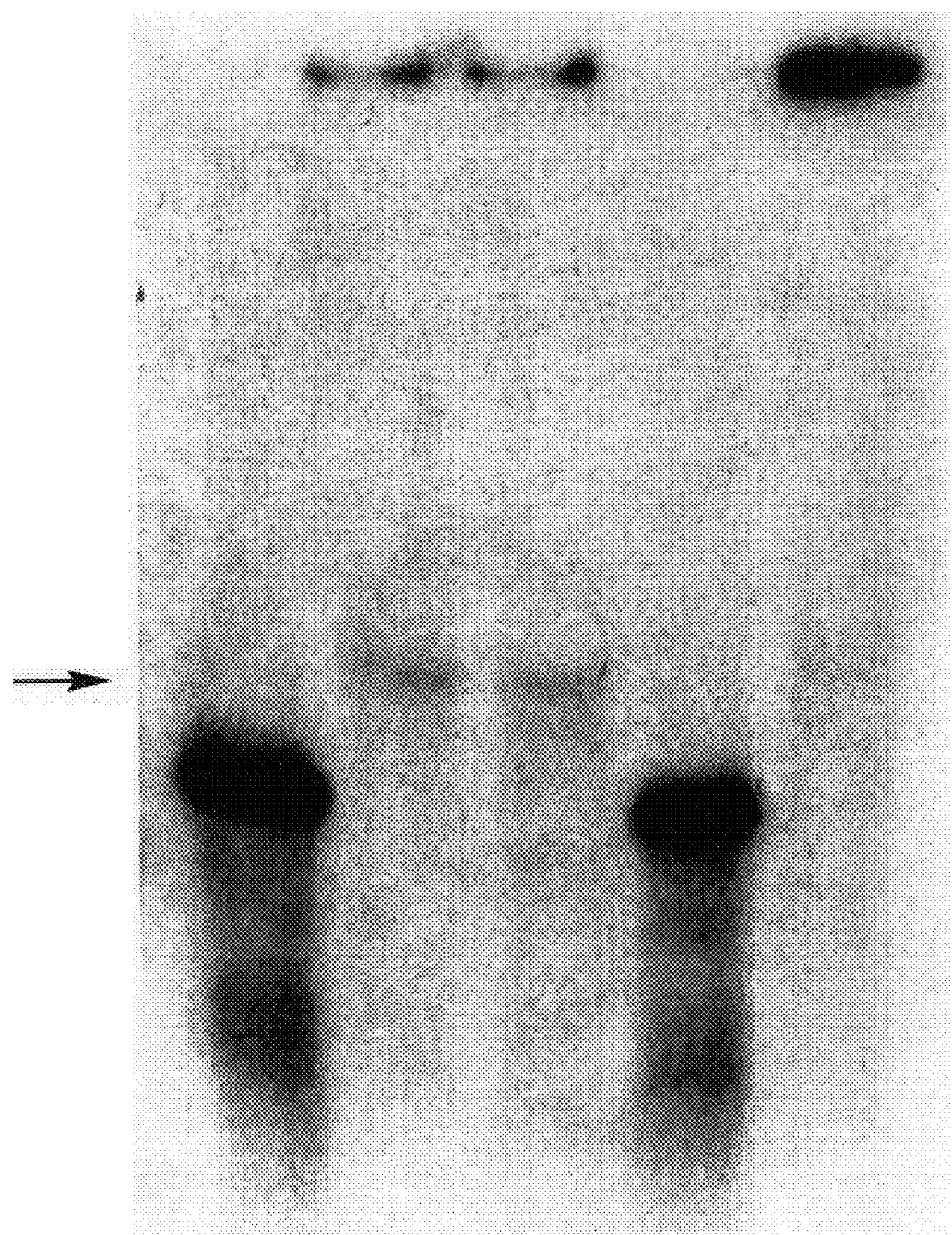
FIG. 12 shows a Northern blot of total RNA isolated from *H. halobium* Bop deficient strain L33 transformed with pUBP2 containing the rat serotonin receptor gene. Lanes 2 and 5 contain RNA from wild type strain L33 transformed with the 1.2 kb PstI/BamHI fragment containing the bop gene in pUBP2 as a control. Lanes 1, 3 and 4 contain DNA from L33 transformed with the rat serotonin receptor gene. The 1.85 kb PstI/BamHI fragment of FIGS. 9 and 10 was used as probe. The arrow shows the location of the rat serotonin receptor RNA.
Figure 18:
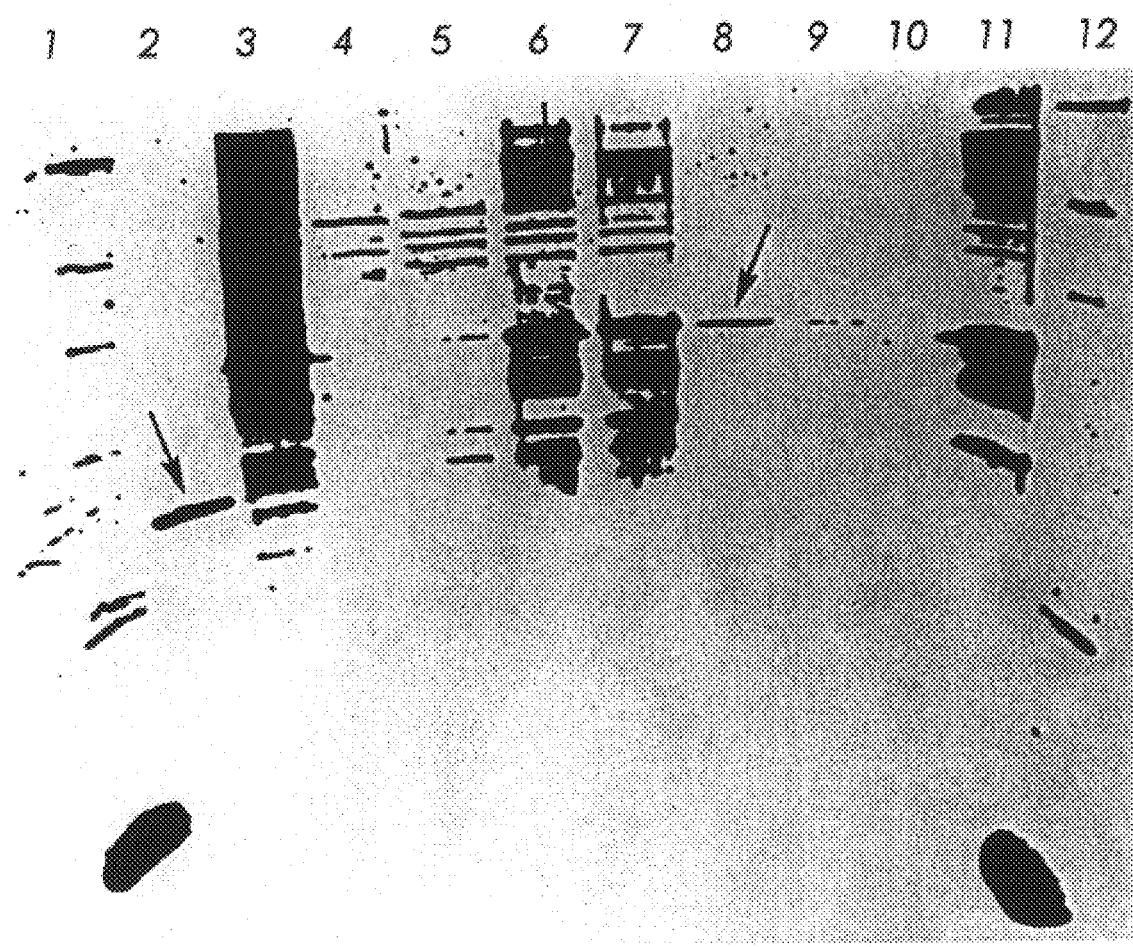
FIG. 18 shows a Western blot of H. halobium transformed with pBRAT. Blots were probed with antibodies to the catalytic subunit of aspartate transcarbamylase. Lane 2 contains *E. coli* aspartate transcarbamylase. Lanes 6–9 and 11 contain protein from *H. halobium* transformed with pBRAT. The arrow in lane 8 indicates the position of the bacteriorhodopsin/aspartate transcarbamylase (BR/ATCase) fusion protein.
Figure 19A:
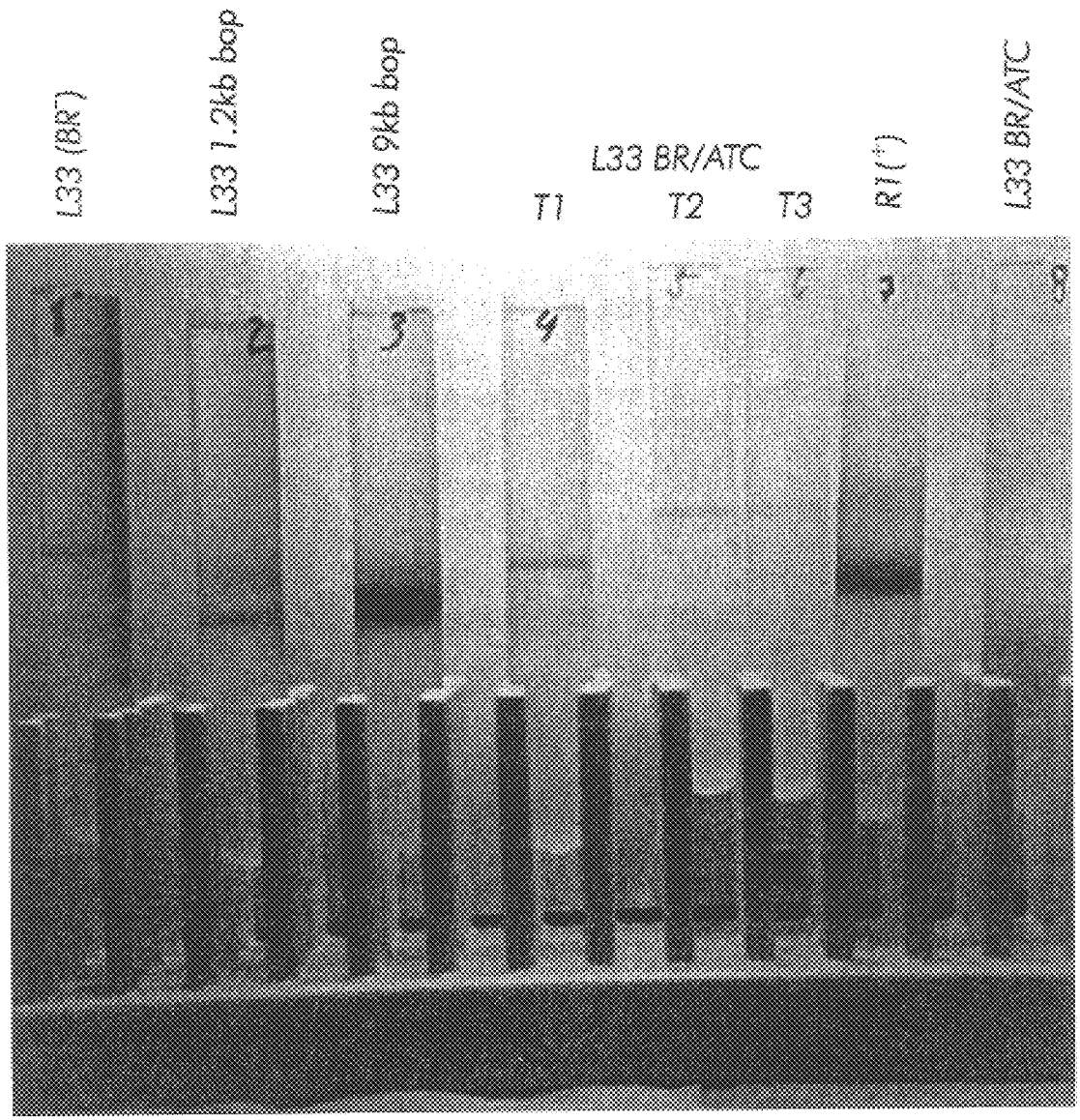
FIG. 19 shows the localization of expression of the bacteriorhodopsin/aspartate transcarbamylase (BR/ATCase) fusion protein to the purple halobacterial cell membranes. Washed *H. halobium* whole cell membranes fractionated on sucrose density gradients (A) were electrophoresed on SDS-polyacrylamide gels and stained with Coomassie blue (B). Lanes in (B) contained the following protein samples: Molecular weight markers (lane 1); unfractionated total membranes from *H. halobium* strain L33 transformed with pBRAT (lane 2); purple membrane from *H. halobium* strain L33 transformed with a 1.2 Kb PstI/BamHI fragment containing the bop gene (lane 3) or with a 9 Kb genomic DNA fragment containing the bop gene (lane 4); total membranes from *H. halobium* strain L33 (lane 5); purple membrane from wild-type *H. halobium* strain R1 (lane 6); purple membrane of *H. halobium* strain L33 transformed with pBRAT (lanes 7–9).
Figure 19B:
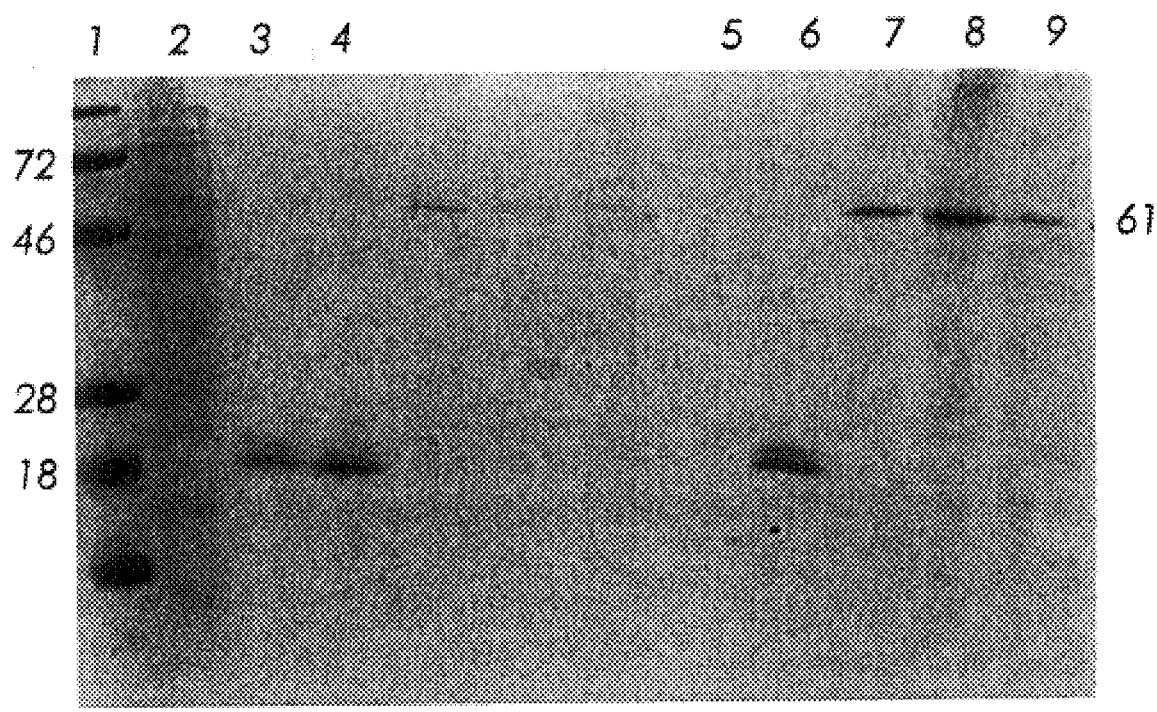

*H. halobium* transformed with pUBP2 containing the pBRAT PstI/BamHI fragment and with pUBP2 containing the pENDS-Ser PstI/BamHI fragment was plated on solid complex (YET) medium containing 25 µM mevinolin Plates were incubated for one to two weeks at 42° C. to permit growth of transformants. Plasmid DNA was isolated from individual transformants using Magic Minipreps DNA Purification System (Promega Corp., Madison, Wis.). Southern analysis was used to verify the presence of the heterologous gene on pUBP2. Southern blot analysis using the AlwNI/NotI fragment containing the serotonin receptor gene as probe indicated the presence of serotonin receptor gene sequences in all assayed transformants (FIG. 11). Total RNA was isolated from individual transformants using the RNAzol procedure (Cinna Biotech) and subjected to Northern analysis (18). Northern blot analysis revealed that transcription of Ser gene sequences had occurred (FIG. 12). Western analysis using both BR and ATCase antibodies demonstrated that the BR/ATCase fusion was expressed and localized to halobacterial membranes (FIG. 18). Washed halobacterial whole cell membranes were fractionated on sucrose gradients (FIG. 19A) and aliquots were subjected to SDS PAGE (FIG. 19B). A band corresponding to the predicted molecular weight of the fusion protein (i.e., ~60 kDa, see FIG. 19B) was observed which derived from a purple fraction. These data verify expression of the fusion and indicate that the BR portion of the fusion is folded correctly in the halobacterial membrane. The presence of the BR chromophore (extinction coefficient of 63,000; 31) affords an estimate of 5 mg/liter of fusion protein expression.

Transformants testing positive in Southern and Northern analyses are subjected to Western analysis if specific antibodies to the heterologous protein are available. If antibodies are not available, DNA encoding an epitope known to be antigenic may be engineered into the expression vector construction to aid in detection of expression. An example of such an epitope is the sequence encoding Glu-Glu-Glu-Glu-Tyr-Met-Pro-Met-Glu (SEQ ID NO:5) (22). Alternatively, expression of the heterologous protein may be assayed functionally; for example, ligand binding assays for receptors, and assays for enzymatic activity for soluble proteins using appropriate substrates.

4. Purification of heterologous polypeptides

Production of the heterologous polypeptide may be stopped in a variety of ways. Where the heterologous polypeptide is released into the medium, it may be isolated in a soluble or insoluble form using physical e.g. mechanical or thermal, or chemical treatments. Treatments employed may include freezing ($\leq 0°$ C.), heating, hydrodynamic shearing, drying, selective filtration or precipitation by addition of acid, base, salts or organic solvents.

Where the expressed heterologous polypeptide resides in the membrane or in the cytoplasm, cells are harvested to separate them from the culture medium. Various techniques may be used for harvesting, desirably using centrifugation. The supernatant may then be discarded and the cell pellet washed with an appropriate buffered aqueous medium to remove any residual culture medium components. Typically the buffered medium will be at a temperature in the range of about 1 to 10° C., more usually 4° C.

The cells may be lysed by any convenient means, such as freezing and mechanical, use of hypotonic solutions (23), and the like. The resulting dispersion of disrupted cells is then treated by such means as to substantially separate cell membranes from soluble proteins and other contaminants. Several techniques may be employed to advantage for isolating membranes including differential centrifugation, density gradient centrifugation, and the like. This membrane isolation separates the fusion protein from the bulk of the soluble proteins.

Heterologous polypeptides are purified according to procedures dependent on their individual properties and those of BR. Where the expressed soluble heterologous polypeptide is fused at the C-terminal region of BR, advantage may be taken of the likelihood that the BR domain will anchor the fusion protein in the membrane.

Where the heterologous polypeptide is expressed as a fusion polypeptide linked to the C-terminal region, or fragment thereof, of the bacteriorhodopsin gene with a unique protease site between said heterologous polypeptide and C-terminal region, the heterologous polypeptide may be isolated by incubating the halobacterial membranes with an appropriate unique protease to effect substantially complete cleavage at the protease cleavage site. For example, where the heterologous polypeptide is linked to the bacteriorhodopsin C-terminal region through the amino acid sequence Ile-Glu-Gly-Arg (SEQ ID NO:4), cell membranes are incubated with factor $X_a$ under conditions recommended by the manufacturers. Factor $X_a$ is dissolved in redistilled water to a final protein concentration of 1 mg/ml. The fusion protein to be cleaved is dissolved in 100 mM NaCl, 50 mM Tris-HCl, 1 mM $CaCl_2$, pH 8.0. To increase the solubility of the substrate, urea or acetonitrile can be added up to a final concentration of 1 M and 10% (v/v), respectively without significant inhibition of the enzyme activity. The recommended amount of enzyme is $1/200$ to $1/10$ of the substrate by weight. Incubation should be carried out at 4° C. to 25° C. for 1–18 h. The optimum cleavage conditions have to be determined for each fusion protein. The release of the desired polypeptide from the fusion protein is influenced by the adjacent amino acid sequences at the cleavage site, the size of the two fused polypeptide components, and the accessibility of the cleavage site. Protease treatment is followed by standard purification protocols to remove the minor unique protease component.

If further purification of the heterologous polypeptide protein is desired, antibodies specific for the heterologous polypeptide, ligand affinity, electrophoresis, chromatography, zonal centrifugation, and the like, may be employed to advantage. The product may then be dried by any convenient means, such as freeze drying, spray drying, and the like, or alternatively suspended in an appropriate buffered aqueous solution. The heterologous polypeptide product is then ready for use.

5. Bioassays

The heterologous polypeptides may be assayed using protocols dependent on their individual properties. For example, receptors are assayed using ligand binding assays. Soluble proteins having enzyme activity are assayed using appropriate substrates.

Bibliography

For the sake of convenience, various documents referenced in the body of the present specification are grouped in the following bibliography by number that corresponds to the parenthetical number of that reference in the text. Each of these documents is hereby expressly incorporated by reference.

1. Gropp *Syst. Appl. Microbiol.* 7, 95 (1986).
2. Zillig *Eur. J. Biochem.* 173, 473 (1988).
3. Dennis *J. Bacteriol.* 168, 471 (1986).
4. Oesterhelt *Proc. Nat. Acad. Sci. USA* 70, 2853 (1971).
5. Henderson *Annu. Rev. Biophys. Bioenerg.* 6, 87 (1977).
6. Katre *Proc. Natl. Acad. Sci. USA* 78, 4068 (1981)
7. Blasieo *Proc. natl. Acad. Sci. USA* 87, 6772 (1990)
8. Holmes *J. Bacteriol.* 172, 756 (1990)
9. Ni *Gene* 90, 169 (1990).
10. Charlebois *Proc. Natl. Acad. Sci. usa* 84, 8530 (1987)
11. Cline *J. bacterial.* 169, 1341 (1987)
12. Maniatis "Molecular Cloning: A Laboratory Manual". Cold Spring Harbor Laboratory, CSH, N.Y. (1989)
13. Betlach *Nucl. Acids Res.* 12, 7949 (1984)
14. Leong *J. bacteriol.* 170, 4903 (1988)
15. Wagner *FEBS Letters* 131, 341 (1983)
16. Spudich *Proc. Natl. Acad. Sci. USA,* 79 4398 (1982)
17. Pfeifer *J. Bacteriol.* 145, 375 (1981)
18. Shand *J. Bacteriol.* 173, 4692 (1991)
19. Betlach, In: "Protocols for Archael Research". Robb & Das Sarma (Eds.), Cold Spring Harbor Laboratory. Cold Spring Harbor, N.Y., in press (1993)
20. Yanisch-Perron *Gene* 33, 103 (1985)
21. Kamekura *Appl. Environmental Microbiol.* 54, 990 (1988)
22. Grussenmeyer *Proc. Natl. Acad.Sci. USA* 82 7952 (1985)
23. Turner *Biochemistry* 32 1332 (1993)
24. Cline *Can. J. Microbiol.,* 35, 148 (1989)
25. Feinberg *Analytical Biochemistry* 132 6 (1983)
26. Hoffmann *Nucleic Acids Research* 19 6337 (1991)
27. Julius *Science* 241 558 (1988)
28. Kuhn *Gene* 44 253 (1986)
29. Kunkel *Methods Enzymol.* 154 367 (1987)
30. Nowlan *J. Biol. Chem.* 260 14712 (1985)
31. Power *Gene* 113 95 (1992)
32. Shand *Biochemistry* 30 3082 (1991)
33. Vu *Cell* 64 1057 (1991)

Concluding Remarks

The foregoing description details specific methods that can be employed to practice the present invention. Having detailed specific methods initially used to construct and use vectors for the expression, isolation, detection and further purification of heterologous polypeptides in halobacteria, those skilled in the art will know how to devise alternative reliable methods for arriving at the same and equivalent systems described herein. The foregoing should not be construed as limiting the overall scope hereof; rather, the ambit of the present invention is to be governed only by the lawful interpretation of the appended claims.

We claim:

1. An expression vector useful for the production of a heterologous polypeptide in a halobacterium host cell, said vector comprising:
   a) an operable halobacterium transcription and translation regulatory DNA sequence;
   b) a DNA sequence encoding a heterologous polypeptide located 3' to said regulatory DNA sequence of a); and
   c) operable halobacterium transcription and translation stop signals located 3' to said DNA sequence encoding a heterologous polypeptide of b).

2. The vector according to claim 1 having a DNA sequence encoding replication and/or selection capability for said halobacterium host cell.

3. The vector according to claim 1 containing an additional DNA sequence encoding the pre-sequence of bacteriorhodopsin gene between said regulatory DNA sequence of a) and said DNA sequence encoding a heterologous polypeptide of b) for expression of a fusion polypeptide of said pre-sequence with said heterologous polypeptide.

4. The vector according to claim 1 or 3 containing an additional DNA sequence encoding at least a membranous domain of the bacteriorhodopsin gene and a DNA sequence operably encoding a unique protease cleavage site and a restriction site, in optional order, between said DNA sequence encoding at least a membranous domain and said DNA sequence encoding a heterologous polypeptide of b), said additional DNA sequence located 3' to said DNA sequence encoding a heterologous polypeptide of b).

5. A halobacterium host cell transformed with a vector according to claim 1.

6. A halobacterium host cell transformed with a vector according to claim 4.

7. A method for producing a heterologous polypeptide in a halobacterium host cell, said method comprising:
   a) transforming a halobacterium host cell with an expression vector, said expression vector comprising:
      i) an operable halobacterium transcription and translation regulatory DNA sequence;
      ii) a DNA sequence encoding a heterologous polypeptide located 3' to said regulatory DNA sequence of i); and
      iii) operable halobacterium transcription and translation stop signals located 3' to said DNA sequence encoding a heterologous polypeptide of ii); and
   b) causing expression of said DNA sequence encoding a heterologous polypeptide of ii);
wherein said heterologous polypeptide is other than a halobacterium polypeptide.

8. The method according to claim 7 wherein said elements include an additional DNA sequence encoding at least a membranous domain of the bacteriorhodopsin gene and a DNA sequence operably encoding a unique protease cleavage site and a restriction site, in optional order, between said DNA sequence encoding at least a membranous domain and said DNA sequence encoding a heterologous polypeptide of ii), said additional DNA sequence located 3' to said DNA sequence encoding a heterologous polypeptide of ii).

9. A method for producing a heterologous polypeptide in a halobacterium host comprising causing expression of DNA encoding said heterologous polypeptide wherein an expression vector comprising the DNA encoding said heterologous polypeptide is operably expressed in said halobacterium host and said heterologous polypeptide is other than a halobacterium polypeptide.

10. A method for producing a heterologous polypeptide in a halobacterium host comprising:
   a) transforming said halobacterium host with an expression vector encoding a fusion polypeptide, said expression vector comprising:
      i) halobacterium transcription and translation regulatory DNA;
      ii) DNA encoding a heterologous polypeptide;
      iii) DNA encoding a unique protease cleavage site;
      iv) DNA encoding a membranous domain of bacteriorhodopsin;
      v) wherein said DNA of i), ii), iii), and iv) is operably linked;
   b) causing expression of DNA encoding said fusion polypeptide such that said fusion polypeptide is localized in the membranes; and c) incubating cells of said halobacterium host comprising said membrane-bound fusion polypeptide with a protease such that said protease cleaves at said unique protease cleavage site to release said heterologous polypeptide from said membranes;

wherein said heterologous polypeptide is other than a halobacterium polypeptide.

* * * * *

UNITED STATES PATENT AND TRADEMARK OFFICE
CERTIFICATE OF CORRECTION

PATENT NO : 6,010,885
DATED : January 4, 2000
INVENTOR(S): TURNER et al.

It is certified that error appears in the above-identified patent and that said Letters Patent is hereby corrected as shown below:

Column 1, lines 10-12 under section REFERENCE TO RELATED APPLICATIONS, delete the sentence "The Government has rights in this invention pursuant to Grant No. GM-31785 awarded by the National Institutes of Health." and insert -- This invention was made with Government support under Grant No. GM-14053 and GM-31785 awarded by the National Institutes of Health. The Government has certain rights in this invention.--.

Signed and Sealed this

Sixth Day of February, 2001

Q. TODD DICKINSON

*Attest:*

*Attesting Officer*         *Director of Patents and Trademarks*

SEQUENCE LISTING (1) GENERAL INFORMATION:

(iii) NUMBER OF SEQUENCES: 15

(2) INFORMATION FOR SEQ ID NO:1:

(i) SEQUENCE CHARACTERISTICS:
      (A) LENGTH: 1254 base pairs
      (B) TYPE: nucleic acid
      (C) STRANDEDNESS: double
      (D) TOPOLOGY: linear (ii) MOLECULE TYPE: DNA (genomic)

(ix) FEATURE:
      (A) NAME/KEY: misc_feature
      (B) LOCATION: 376..414
      (D) OTHER INFORMATION: /note= "Bacteriorhodopsin
          pre-sequence."

(ix) FEATURE:
      (A) NAME/KEY: CDS
      (B) LOCATION: 376..1161

(ix) FEATURE:
      (A) NAME/KEY: misc_feature
      (B) LOCATION: 3..8
      (D) OTHER INFORMATION: /note= "PstI site."

(ix) FEATURE:
      (A) NAME/KEY: misc_feature
      (B) LOCATION: 1245..1250
      (D) OTHER INFORMATION: /note= "BamHI site."

(ix) FEATURE:
      (A) NAME/KEY: misc_signal
      (B) LOCATION: 374
      (D) OTHER INFORMATION: /note= "RNA start site."

(ix) FEATURE:
      (A) NAME/KEY: misc_feature
      (B) LOCATION: 9..414
      (D) OTHER INFORMATION: /note= "Bacteriorhodopsin
          transcriptional and translational regulatory
          sequences are located in this region."

(xi) SEQUENCE DESCRIPTION: SEQ ID NO:1:

```
ATCTGCAGGA TGGGTGCAAC CGTGAAGTCC GTCACGGCTG CGTCACGACA GGAGCCGACC      60

AGCGACACCC AGAAGGTGCG AACGGTTGAG TGCCGCAACG ATCACGAGTT TTTCGTGCGC     120

TTCGAGTGGT AACACGCGTG CACGCATCGA CTTCACCGCG GGTGTTTCGA CGCCAGCCGG     180

CCGTTGAACC AGCAGGCAGC GGGCATTTCA CAGCCGCTGT GGCCCACACA CTCGGTGGGG     240

TGCGCTATTT TGGTATGGTT TGGAATCCGC GTGTCGGCTC CGTGTCTGAC GGTTCATCGG     300

TCTAAATTCC GTCACGAGCG TACCATACTG ATTGGGTCGT AGAGTTACAC ACATATCCTC     360

GTTAGGTACT GTTGC ATG TTG GAG TTA TTG CCA ACA GCA GTG GAG GGG GTA     411
                Met Leu Glu Leu Leu Pro Thr Ala Val Glu Gly Val
                  1               5                  10

TCG CAG GCC CAG ATC ACC GGA CGT CCG GAG TGG ATC TGG CTA GCG CTC     459
Ser Gln Ala Gln Ile Thr Gly Arg Pro Glu Trp Ile Trp Leu Ala Leu
     15                  20                  25

GGT ACG GCG CTA ATG GGA CTC GGG ACG CTC TAT TTC CTC GTG AAA GGG     507
Gly Thr Ala Leu Met Gly Leu Gly Thr Leu Tyr Phe Leu Val Lys Gly
         30                  35                  40

ATG GGC GTC TCG GAC CCA GAT GCA AAG AAA TTC TAC GCC ATC ACG ACG     555
Met Gly Val Ser Asp Pro Asp Ala Lys Lys Phe Tyr Ala Ile Thr Thr
 45                  50                  55                  60
```

```
CTC GTC CCA GCC ATC GCG TTC ACG ATG TAC CTC TCG ATG CTG CTG GGG              603
Leu Val Pro Ala Ile Ala Phe Thr Met Tyr Leu Ser Met Leu Leu Gly
                 65                  70                  75

TAT GGC CTC ACA ATG GTA CCG TTC GGT GGG GAG CAG AAC CCC ATC TAC              651
Tyr Gly Leu Thr Met Val Pro Phe Gly Gly Glu Gln Asn Pro Ile Tyr
             80                  85                  90

TGG GCG CGG TAC GCT GAC TGG CTG TTC ACC ACG CCG CTG TTG TTG TTA              699
Trp Ala Arg Tyr Ala Asp Trp Leu Phe Thr Thr Pro Leu Leu Leu Leu
         95                 100                 105

GAC CTC GCG TTG CTC GTT GAC GCG GAT CAG GGA ACG ATC CTT GCG CTC              747
Asp Leu Ala Leu Leu Val Asp Ala Asp Gln Gly Thr Ile Leu Ala Leu
        110                 115                 120

GTC GGT GCC GAC GGC ATC ATG ATC GGG ACC GGC CTG GTC GGC GCA CTG              795
Val Gly Ala Asp Gly Ile Met Ile Gly Thr Gly Leu Val Gly Ala Leu
125                 130                 135                 140

ACG AAG GTC TAC TCG TAC CGC TTC GTG TGG TGG GCG ATC AGC ACC GCA              843
Thr Lys Val Tyr Ser Tyr Arg Phe Val Trp Trp Ala Ile Ser Thr Ala
                145                 150                 155

GCG ATG CTG TAC ATC CTG TAC GTG CTG TTC TTC GGG TTC ACC TCG AAG              891
Ala Met Leu Tyr Ile Leu Tyr Val Leu Phe Phe Gly Phe Thr Ser Lys
            160                 165                 170

GCC GAA AGC ATG CGC CCC GAG GTC GCA TCC ACG TTC AAA GTA CTG CGT              939
Ala Glu Ser Met Arg Pro Glu Val Ala Ser Thr Phe Lys Val Leu Arg
        175                 180                 185

AAC GTT ACC GTT GTG TTG TGG TCC GCG TAT CCC GTC GTG TGG CTG ATC              987
Asn Val Thr Val Val Leu Trp Ser Ala Tyr Pro Val Val Trp Leu Ile
        190                 195                 200

GGC AGC GAA GGT GCG GGA ATC GTG CCG CTG AAC ATC GAG ACG CTG CTG             1035
Gly Ser Glu Gly Ala Gly Ile Val Pro Leu Asn Ile Glu Thr Leu Leu
205                 210                 215                 220

TTC ATG GTG CTT GAC GTG AGC GCG AAG GTC GGC TTC GGG CTC ATC CTC             1083
Phe Met Val Leu Asp Val Ser Ala Lys Val Gly Phe Gly Leu Ile Leu
                225                 230                 235

CTG CGC AGT CGT GCG ATC TTC GGC GAA GCC GAA GCG CCG GAG CCG TCC             1131
Leu Arg Ser Arg Ala Ile Phe Gly Glu Ala Glu Ala Pro Glu Pro Ser
            240                 245                 250

GCC GGC GAC GGC GCG GCC GCG ACC AGC GAC TGATCGCACA CGCAGGACAG              1181
Ala Gly Asp Gly Ala Ala Ala Thr Ser Asp
        255                 260

CCCCACAACC GGCGCGGCTG TGTTCAACGA CACACGATGA GTCCCCCACT CGGTCTTGTA          1241

CTCGGATCCT TTT                                                              1254

(2) INFORMATION FOR SEQ ID NO:2:

(i) SEQUENCE CHARACTERISTICS:
        (A) LENGTH: 262 amino acids
        (B) TYPE: amino acid
        (D) TOPOLOGY: linear (ii) MOLECULE TYPE: protein (xi) SEQUENCE DESCRIPTION: SEQ ID NO:2:

Met Leu Glu Leu Leu Pro Thr Ala Val Glu Gly Val Ser Gln Ala Gln
 1               5                  10                  15

Ile Thr Gly Arg Pro Glu Trp Ile Trp Leu Ala Leu Gly Thr Ala Leu
            20                  25                  30

Met Gly Leu Gly Thr Leu Tyr Phe Leu Val Lys Gly Met Gly Val Ser
        35                  40                  45

Asp Pro Asp Ala Lys Lys Phe Tyr Ala Ile Thr Thr Leu Val Pro Ala
    50                  55                  60
```

```
Ile Ala Phe Thr Met Tyr Leu Ser Met Leu Leu Gly Tyr Gly Leu Thr
 65              70                  75                  80

Met Val Pro Phe Gly Gly Glu Gln Asn Pro Ile Tyr Trp Ala Arg Tyr
                 85                  90                  95

Ala Asp Trp Leu Phe Thr Thr Pro Leu Leu Leu Asp Leu Ala Leu
                100             105             110

Leu Val Asp Ala Asp Gln Gly Thr Ile Leu Ala Leu Val Gly Ala Asp
            115                 120                 125

Gly Ile Met Ile Gly Thr Gly Leu Val Gly Ala Leu Thr Lys Val Tyr
    130                 135                 140

Ser Tyr Arg Phe Val Trp Trp Ala Ile Ser Thr Ala Ala Met Leu Tyr
145                 150                 155                 160

Ile Leu Tyr Val Leu Phe Phe Gly Phe Thr Ser Lys Ala Glu Ser Met
                165                 170                 175

Arg Pro Glu Val Ala Ser Thr Phe Lys Val Leu Arg Asn Val Thr Val
            180                 185                 190

Val Leu Trp Ser Ala Tyr Pro Val Val Trp Leu Ile Gly Ser Glu Gly
            195                 200                 205

Ala Gly Ile Val Pro Leu Asn Ile Glu Thr Leu Leu Phe Met Val Leu
    210                 215                 220

Asp Val Ser Ala Lys Val Gly Phe Gly Leu Ile Leu Leu Arg Ser Arg
225                 230                 235                 240

Ala Ile Phe Gly Glu Ala Glu Ala Pro Glu Pro Ser Ala Gly Asp Gly
                245                 250                 255

Ala Ala Ala Thr Ser Asp
            260

(2) INFORMATION FOR SEQ ID NO:3:

(i) SEQUENCE CHARACTERISTICS:
        (A) LENGTH: 248 amino acids
        (B) TYPE: amino acid
        (C) STRANDEDNESS: single
        (D) TOPOLOGY: linear (ii) MOLECULE TYPE: protein (ix) FEATURE:
        (A) NAME/KEY: Region
        (B) LOCATION: 225..248
        (D) OTHER INFORMATION: /note= "Cytoplasmic C-terminal
            region of bacteriorhodopsin."

(ix) FEATURE:
        (A) NAME/KEY: Region
        (B) LOCATION: 1
        (D) OTHER INFORMATION: /note= "Pyroglutamate."

(xi) SEQUENCE DESCRIPTION: SEQ ID NO:3:

Xaa Ala Gln Ile Thr Gly Arg Pro Glu Trp Ile Trp Leu Ala Leu Gly
 1               5                  10                  15

Thr Ala Leu Met Gly Leu Gly Thr Leu Tyr Phe Leu Val Lys Gly Met
                 20                  25                  30

Gly Val Ser Asp Pro Asp Ala Lys Lys Phe Tyr Ala Ile Thr Thr Leu
                 35                  40                  45

Val Pro Ala Ile Ala Phe Thr Met Tyr Leu Ser Met Leu Leu Gly Tyr
     50                  55                  60

Gly Leu Thr Met Val Pro Phe Gly Gly Glu Gln Asn Pro Ile Tyr Trp
 65                  70                  75                  80

Ala Arg Tyr Ala Asp Trp Leu Phe Thr Thr Pro Leu Leu Leu Leu Asp
                 85                  90                  95
```

```
Leu Ala Leu Leu Val Asp Ala Asp Gln Gly Thr Ile Leu Ala Leu Val
            100                 105                 110

Gly Ala Asp Gly Ile Met Ile Gly Thr Gly Leu Val Gly Ala Leu Thr
        115                 120                 125

Lys Val Tyr Ser Tyr Arg Phe Val Trp Trp Ala Ile Ser Thr Ala Ala
130                 135                 140

Met Leu Tyr Ile Leu Tyr Val Leu Phe Phe Gly Phe Thr Ser Lys Ala
145                 150                 155                 160

Glu Ser Met Arg Pro Glu Val Ala Ser Thr Phe Lys Val Leu Arg Asn
                165                 170                 175

Val Thr Val Val Leu Trp Ser Ala Tyr Pro Val Val Trp Leu Ile Gly
        180                 185                 190

Ser Glu Gly Ala Gly Ile Val Pro Leu Asn Ile Glu Thr Leu Leu Phe
        195                 200                 205

Met Val Leu Asp Val Ser Ala Lys Val Gly Phe Gly Leu Ile Leu Leu
210                 215                 220

Arg Ser Arg Ala Ile Phe Gly Glu Ala Glu Ala Pro Glu Pro Ser Ala
225                 230                 235                 240

Gly Asp Gly Ala Ala Ala Thr Ser
                245

(2) INFORMATION FOR SEQ ID NO:4:

(i) SEQUENCE CHARACTERISTICS:
        (A) LENGTH: 4 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:4:

Ile Glu Gly Arg
1

(2) INFORMATION FOR SEQ ID NO:5:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:5:

Glu Glu Glu Glu Tyr Met Pro Met Glu
1               5

(2) INFORMATION FOR SEQ ID NO:6:

(i) SEQUENCE CHARACTERISTICS:
        (A) LENGTH: 1956 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 376..1812

(ix) FEATURE:
        (A) NAME/KEY: misc_feature
```

(B) LOCATION: 376..414
                (D) OTHER INFORMATION: /note= "Bacteriorhodopsin
                    pre-sequence."

(ix) FEATURE:
                (A) NAME/KEY: terminator
                (B) LOCATION: 1864..1866
                (D) OTHER INFORMATION: /note= "Bacteriorhodopsin stop
                    codon."

(ix) FEATURE:
                (A) NAME/KEY: mutation
                (B) LOCATION: replace(213, "")
                (D) OTHER INFORMATION: /note= "G to T mutation removes
                    AlwNI restriction site."

(ix) FEATURE:
                (A) NAME/KEY: misc_feature
                (B) LOCATION: 427..435
                (D) OTHER INFORMATION: /note= "AlwNI cloning site."

(ix) FEATURE:
                (A) NAME/KEY: mutation
                (B) LOCATION: replace(930, "")
                (D) OTHER INFORMATION: /note= "G to A mutation removes
                    AlwNI restriction site."

(ix) FEATURE:
                (A) NAME/KEY: mutation
                (B) LOCATION: replace(1179, "")
                (D) OTHER INFORMATION: /note= "T to A mutation removes
                    AlwNI site."

(ix) FEATURE:
                (A) NAME/KEY: mutation
                (B) LOCATION: replace(1245, "")
                (D) OTHER INFORMATION: /note= "G to A mutation removes
                    PstI restriction site."

(ix) FEATURE:
                (A) NAME/KEY: misc_signal
                (B) LOCATION: 374
                (D) OTHER INFORMATION: /note= "RNA start site."

(ix) FEATURE:
                (A) NAME/KEY: mutation
                (B) LOCATION: replace(1863, "")
                (D) OTHER INFORMATION: /note= "C to T mutation removes
                    AlwNI restriction site."

(ix) FEATURE:
                (A) NAME/KEY: terminator
                (B) LOCATION: 1813..1815
                (D) OTHER INFORMATION: /note= "Muscarinic "OM1" stop
                    codon."

(xi) SEQUENCE DESCRIPTION: SEQ ID NO:6:

```
ATCTGCAGGA TGGGTGCAAC CGTGAAGTCC GTCACGGCTG CGTCACGACA GGAGCCGACC      60

AGCGACACCC AGAAGGTGCG AACGGTTGAG TGCCGCAACG ATCACGAGTT TTTCGTGCGC     120

TTCGAGTGGT AACACGCGTG CACGCATCGA CTTCACCGCG GGTGTTTCGA CGCCAGCCGG     180

CCGTTGAACC AGCAGGCAGC GGGCATTTCA CATCCGCTGT GGCCCACACA CTCGGTGGGG     240

TGCGCTATTT TGGTATGGTT TGGAATCCGC GTGTCGGCTC CGTGTCTGAC GGTTCATCGG     300

TCTAAATTCC GTCACGAGCG TACCATACTG ATTGGGTCGT AGAGTTACAC ACATATCCTC     360

GTTAGGTACT GTTGC ATG TTG GAG TTA TTG CCA ACA GCA GTG GAG GGG GTA     411
                Met Leu Glu Leu Leu Pro Thr Ala Val Glu Gly Val
                 1               5                  10

TCG CAG GCC CAG ATC CAG GCG CTG ATG AAC ACT TCA GCC CCA CCT GCT     459
Ser Gln Ala Gln Ile Gln Ala Leu Met Asn Thr Ser Ala Pro Pro Ala
     15                  20                  25

GTC AGC CCC AAC ATC ACC GTC CTG GCA CCA GGA AAG GGT CCC TGG CAA     507
Val Ser Pro Asn Ile Thr Val Leu Ala Pro Gly Lys Gly Pro Trp Gln
```

```
              30                    35                    40
GTG GCC TTC ATT GGG ATC ACC ACG GGC CTC CTG TCG CTA GCC ACA GTG       555
Val Ala Phe Ile Gly Ile Thr Thr Gly Leu Leu Ser Leu Ala Thr Val
 45              50                  55                  60

ACA GGC AAC CTG CTG GTA CTC ATC TCT TTC AAG GTC AAC ACG GAG CTC       603
Thr Gly Asn Leu Leu Val Leu Ile Ser Phe Lys Val Asn Thr Glu Leu
                 65                  70                  75

AAG ACA GTC AAT AAC TAC TTC CTG CTG AGC CTG GCC TGT GCT GAC CTC       651
Lys Thr Val Asn Asn Tyr Phe Leu Leu Ser Leu Ala Cys Ala Asp Leu
                 80                  85                  90

ATC ATC GGT ACC TTC TCC ATG AAC CTC TAT ACC ACG TAC CTG CTC ATG       699
Ile Ile Gly Thr Phe Ser Met Asn Leu Tyr Thr Thr Tyr Leu Leu Met
             95                 100                 105

GGC CAC TGG GCT CTG GGC ACG CTG GCT TGT GAC CTC TGG CTG GCC CTG       747
Gly His Trp Ala Leu Gly Thr Leu Ala Cys Asp Leu Trp Leu Ala Leu
         110                 115                 120

GAC TAT GTG GCC AGC AAT GCC TCC GTC ATG AAT CTG CTG CTC ATC AGC       795
Asp Tyr Val Ala Ser Asn Ala Ser Val Met Asn Leu Leu Leu Ile Ser
125                 130                 135                 140

TTT GAC CGC TAC TTC TCC GTG ACT CGG CCC CTG AGC TAC CGT GCC AAG       843
Phe Asp Arg Tyr Phe Ser Val Thr Arg Pro Leu Ser Tyr Arg Ala Lys
                145                 150                 155

CGC ACA CCC CGC CGC GCA GCT CTG ATG ATC GGC CTG GCC TGG CTG GTT       891
Arg Thr Pro Arg Arg Ala Ala Leu Met Ile Gly Leu Ala Trp Leu Val
            160                 165                 170

TCC TTT GTG CTC TGG GCC CCA GCC ATC CTC TTC TGG CAA TAC CTG GTA       939
Ser Phe Val Leu Trp Ala Pro Ala Ile Leu Phe Trp Gln Tyr Leu Val
            175                 180                 185

GGG GAG CGG ACG ATG CTA GCT GGG CAG TGC TAC ATC CAG TTC CTC TCC       987
Gly Glu Arg Thr Met Leu Ala Gly Gln Cys Tyr Ile Gln Phe Leu Ser
        190                 195                 200

CAG CCC ATC ATC ACC TTT GGC ACA GCC ATG GCT GCC TTC TAC CTC CCT      1035
Gln Pro Ile Ile Thr Phe Gly Thr Ala Met Ala Ala Phe Tyr Leu Pro
205                 210                 215                 220

GTC ACA GTC ATG TGC ACG CTC TAC TGG CGC ATC TAC CGG GAG ACA GAG      1083
Val Thr Val Met Cys Thr Leu Tyr Trp Arg Ile Tyr Arg Glu Thr Glu
                225                 230                 235

AAC CGA GCA CGG GAG CTG GCA GCC CTT CAG GGC TCC GAG ACG CCA GGC      1131
Asn Arg Ala Arg Glu Leu Ala Ala Leu Gln Gly Ser Glu Thr Pro Gly
            240                 245                 250

AAA GGG GGT GGC AGC AGC AGC TCA GAG AGG TCT CAG CCA GGG GCA          1179
Lys Gly Gly Gly Ser Ser Ser Ser Glu Arg Ser Gln Pro Gly Ala
            255                 260                 265

GAG GGC TCA CCA GAG ACT CCT CCA GGC CGC TGC TGT CGC TGC TGC CGG      1227
Glu Gly Ser Pro Glu Thr Pro Pro Gly Arg Cys Cys Arg Cys Cys Arg
        270                 275                 280

GCC CCA AGG CTG CTG CAA GCC TAC AGC TGG AAG GAA GAA GAG GAA GAG      1275
Ala Pro Arg Leu Leu Gln Ala Tyr Ser Trp Lys Glu Glu Glu Glu Glu
285                 290                 295                 300

GAC GAA GGC TCC ATG GAG TCC CTC ACA TCC TCA GAG GGA GAG GAG CCT      1323
Asp Glu Gly Ser Met Glu Ser Leu Thr Ser Ser Glu Gly Glu Glu Pro
                305                 310                 315

GGC TCC GAA GTG GTG ATC AAG ATG CCA ATG GTG GAC CCC GAG GCA CAG      1371
Gly Ser Glu Val Val Ile Lys Met Pro Met Val Asp Pro Glu Ala Gln
            320                 325                 330

GCC CCC ACC AAG CAG CCC CCA CGG AGC TCC CCA AAT ACA GTC AAG AGG      1419
Ala Pro Thr Lys Gln Pro Pro Arg Ser Ser Pro Asn Thr Val Lys Arg
        335                 340                 345

CCG ACT AAG AAA GGG CGT GAT CGA GCT GGC AAG GGC CAG AAG CCC CGT      1467
Pro Thr Lys Lys Gly Arg Asp Arg Ala Gly Lys Gly Gln Lys Pro Arg
```

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
|     | 350 |     |     |     |     | 355 |     |     |     |     | 360 |     |     |     |     |      |
| GGA | AAG | GAG | CAG | CTG | GCC | AAG | CGG | AAG | ACC | TTC | TCG | CTG | GTC | AAG | GAG | 1515 |
| Gly | Lys | Glu | Gln | Leu | Ala | Lys | Arg | Lys | Thr | Phe | Ser | Leu | Val | Lys | Glu |      |
| 365 |     |     |     |     | 370 |     |     |     |     | 375 |     |     |     |     | 380 |      |
| AAG | AAG | GCG | GCT | CGG | ACC | CTG | AGT | GCC | ATC | CTC | CTG | GCC | TTC | ATC | CTC | 1563 |
| Lys | Lys | Ala | Ala | Arg | Thr | Leu | Ser | Ala | Ile | Leu | Leu | Ala | Phe | Ile | Leu |      |
|     |     |     |     | 385 |     |     |     |     | 390 |     |     |     |     | 395 |     |      |
| ACC | TGG | ACA | CCG | TAC | AAC | ATC | ATG | GTG | CTG | GTG | TCC | ACC | TTC | TGC | AAG | 1611 |
| Thr | Trp | Thr | Pro | Tyr | Asn | Ile | Met | Val | Leu | Val | Ser | Thr | Phe | Cys | Lys |      |
|     |     |     | 400 |     |     |     |     | 405 |     |     |     |     | 410 |     |     |      |
| GAC | TGT | GTT | CCC | GAG | ACC | CTG | TGG | GAG | CTG | GGC | TAC | TGG | CTG | TGC | TAC | 1659 |
| Asp | Cys | Val | Pro | Glu | Thr | Leu | Trp | Glu | Leu | Gly | Tyr | Trp | Leu | Cys | Tyr |      |
|     |     | 415 |     |     |     |     | 420 |     |     |     |     | 425 |     |     |     |      |
| GTC | AAC | AGC | ACC | ATC | AAC | CCC | ATG | TGC | TAC | GCA | CTC | TGC | AAC | AAA | GCC | 1707 |
| Val | Asn | Ser | Thr | Ile | Asn | Pro | Met | Cys | Tyr | Ala | Leu | Cys | Asn | Lys | Ala |      |
|     |     | 430 |     |     |     |     | 435 |     |     |     |     | 440 |     |     |     |      |
| TTC | CGG | GAC | ACC | TTT | CGC | CTG | CTG | CTT | TGC | CGC | TGG | GAC | AAG | AGA | CGC | 1755 |
| Phe | Arg | Asp | Thr | Phe | Arg | Leu | Leu | Leu | Cys | Arg | Trp | Asp | Lys | Arg | Arg |      |
| 445 |     |     |     |     | 450 |     |     |     |     | 455 |     |     |     |     | 460 |      |
| TGG | CGC | AAG | ATC | CCC | AAG | CGC | CCT | GGC | TCC | GTG | CAC | CGC | ACT | CCC | TCC | 1803 |
| Trp | Arg | Lys | Ile | Pro | Lys | Arg | Pro | Gly | Ser | Val | His | Arg | Thr | Pro | Ser |      |
|     |     |     |     | 465 |     |     |     |     | 470 |     |     |     |     | 475 |     |      |

CGC CAA TGC TGATAGTCCC CTCTCCTGCA TCCCTCCACC CCAGCGGCCG    1852
Arg Gln Cys

CGACCAGCGA TTGATCGCAC ACGCAGGACA GCCCCACAAC CGGCGCGGCT GTGTTCAACG    1912

ACACACGATG AGTCCCCCAC TCGGTCTTGT ACTCGGATCC TTTT    1956

(2) INFORMATION FOR SEQ ID NO:7:

(i) SEQUENCE CHARACTERISTICS:
        (A) LENGTH: 479 amino acids
        (B) TYPE: amino acid
        (D) TOPOLOGY: linear (ii) MOLECULE TYPE: protein (xi) SEQUENCE DESCRIPTION: SEQ ID NO:7:

Met Leu Glu Leu Leu Pro Thr Ala Val Glu Gly Val Ser Gln Ala Gln
 1               5                  10                  15

Ile Gln Ala Leu Met Asn Thr Ser Ala Pro Pro Ala Val Ser Pro Asn
             20                  25                  30

Ile Thr Val Leu Ala Pro Gly Lys Gly Pro Trp Gln Val Ala Phe Ile
         35                  40                  45

Gly Ile Thr Thr Gly Leu Leu Ser Leu Ala Thr Val Thr Gly Asn Leu
     50                  55                  60

Leu Val Leu Ile Ser Phe Lys Val Asn Thr Glu Leu Lys Thr Val Asn
 65                  70                  75                  80

Asn Tyr Phe Leu Leu Ser Leu Ala Cys Ala Asp Leu Ile Ile Gly Thr
                 85                  90                  95

Phe Ser Met Asn Leu Tyr Thr Thr Tyr Leu Leu Met Gly His Trp Ala
            100                 105                 110

Leu Gly Thr Leu Ala Cys Asp Leu Trp Leu Ala Leu Asp Tyr Val Ala
        115                 120                 125

Ser Asn Ala Ser Val Met Asn Leu Leu Leu Ile Ser Phe Asp Arg Tyr
    130                 135                 140

Phe Ser Val Thr Arg Pro Leu Ser Tyr Arg Ala Lys Arg Thr Pro Arg
145                 150                 155                 160

Arg Ala Ala Leu Met Ile Gly Leu Ala Trp Leu Val Ser Phe Val Leu

```
                    165                 170                 175
Trp Ala Pro Ala Ile Leu Phe Trp Gln Tyr Leu Val Gly Glu Arg Thr
                180                 185                 190
Met Leu Ala Gly Gln Cys Tyr Ile Gln Phe Leu Ser Gln Pro Ile Ile
            195                 200                 205
Thr Phe Gly Thr Ala Met Ala Ala Phe Tyr Leu Pro Val Thr Val Met
        210                 215                 220
Cys Thr Leu Tyr Trp Arg Ile Tyr Arg Glu Thr Glu Asn Arg Ala Arg
225                 230                 235                 240
Glu Leu Ala Ala Leu Gln Gly Ser Glu Thr Pro Gly Lys Gly Gly Gly
                245                 250                 255
Ser Ser Ser Ser Ser Glu Arg Ser Gln Pro Gly Ala Glu Gly Ser Pro
            260                 265                 270
Glu Thr Pro Pro Gly Arg Cys Cys Arg Cys Cys Arg Ala Pro Arg Leu
        275                 280                 285
Leu Gln Ala Tyr Ser Trp Lys Glu Glu Glu Glu Asp Glu Gly Ser
290                 295                 300
Met Glu Ser Leu Thr Ser Ser Glu Gly Glu Glu Pro Gly Ser Glu Val
305                 310                 315                 320
Val Ile Lys Met Pro Met Val Asp Pro Glu Ala Gln Ala Pro Thr Lys
                325                 330                 335
Gln Pro Pro Arg Ser Ser Pro Asn Thr Val Lys Arg Pro Thr Lys Lys
                340                 345                 350
Gly Arg Asp Arg Ala Gly Lys Gly Gln Lys Pro Arg Gly Lys Glu Gln
                355                 360                 365
Leu Ala Lys Arg Lys Thr Phe Ser Leu Val Lys Glu Lys Lys Ala Ala
370                 375                 380
Arg Thr Leu Ser Ala Ile Leu Leu Ala Phe Ile Leu Thr Trp Thr Pro
385                 390                 395                 400
Tyr Asn Ile Met Val Leu Val Ser Thr Phe Cys Lys Asp Cys Val Pro
                405                 410                 415
Glu Thr Leu Trp Glu Leu Gly Tyr Trp Leu Cys Tyr Val Asn Ser Thr
                420                 425                 430
Ile Asn Pro Met Cys Tyr Ala Leu Cys Asn Lys Ala Phe Arg Asp Thr
            435                 440                 445
Phe Arg Leu Leu Leu Cys Arg Trp Asp Lys Arg Arg Trp Arg Lys Ile
        450                 455                 460
Pro Lys Arg Pro Gly Ser Val His Arg Thr Pro Ser Arg Gln Cys
465                 470                 475

(2) INFORMATION FOR SEQ ID NO:8:

(i) SEQUENCE CHARACTERISTICS:
        (A) LENGTH: 1581 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 376..1437

(ix) FEATURE:
        (A) NAME/KEY: misc_feature
        (B) LOCATION: 376..414
        (D) OTHER INFORMATION: /note= "Bacteriorhodopsin
            pre-sequence."
```

(ix) FEATURE:
    (A) NAME/KEY: terminator
    (B) LOCATION: 1489..1491
    (D) OTHER INFORMATION: /note= "Bacteriorhodopsin stop
        codon."

(ix) FEATURE:
    (A) NAME/KEY: mutation
    (B) LOCATION: replace(213, "")
    (D) OTHER INFORMATION: /note= "G to T mutation removes
        AlwNI restriction site."

(ix) FEATURE:
    (A) NAME/KEY: misc_feature
    (B) LOCATION: 427..435
    (D) OTHER INFORMATION: /note= "AlwNI cloning site."

(ix) FEATURE:
    (A) NAME/KEY: mutation
    (B) LOCATION: replace(930, "")
    (D) OTHER INFORMATION: /note= "G to A mutation removes
        AlwNI site."

(ix) FEATURE:
    (A) NAME/KEY: misc_signal
    (B) LOCATION: 374
    (D) OTHER INFORMATION: /note= "RNA start site."

(ix) FEATURE:
    (A) NAME/KEY: terminator
    (B) LOCATION: 1438..1440
    (D) OTHER INFORMATION: /note= "Muscarinic stop codon."

(ix) FEATURE:
    (A) NAME/KEY: mutation
    (B) LOCATION: replace(1488, "")
    (D) OTHER INFORMATION: /note= "C to T mutation removes
        AlwNI restriction site."

(xi) SEQUENCE DESCRIPTION: SEQ ID NO:8:

```
ATCTGCAGGA TGGGTGCAAC CGTGAAGTCC GTCACGGCTG CGTCACGACA GGAGCCGACC      60

AGCGACACCC AGAAGGTGCG AACGGTTGAG TGCCGCAACG ATCACGAGTT TTTCGTGCGC     120

TTCGAGTGGT AACACGCGTG CACGCATCGA CTTCACCGCG GGTGTTTCGA CGCCAGCCGG     180

CCGTTGAACC AGCAGGCAGC GGGCATTTCA CATCCGCTGT GGCCCACACA CTCGGTGGGG     240

TGCGCTATTT TGGTATGGTT TGGAATCCGC GTGTCGGCTC CGTGTCTGAC GGTTCATCGG     300

TCTAAATTCC GTCACGAGCG TACCATACTG ATTGGGTCGT AGAGTTACAC ACATATCCTC     360

GTTAGGTACT GTTGC ATG TTG GAG TTA TTG CCA ACA GCA GTG GAG GGG GTA     411
              Met Leu Glu Leu Leu Pro Thr Ala Val Glu Gly Val
                1               5                  10

TCG CAG GCC CAG ATC CAG GCG CTG ATG AAC ACT TCA GCC CCA CCT GCT     459
Ser Gln Ala Gln Ile Gln Ala Leu Met Asn Thr Ser Ala Pro Pro Ala
     15                  20                  25

GTC AGC CCC AAC ATC ACC GTC CTG GCA CCA GGA AAG GGT CCC TGG CAA     507
Val Ser Pro Asn Ile Thr Val Leu Ala Pro Gly Lys Gly Pro Trp Gln
 30                  35                  40

GTG GCC TTC ATT GGG ATC ACC ACG GGC CTC CTG TCG CTA GCC ACA GTG     555
Val Ala Phe Ile Gly Ile Thr Thr Gly Leu Leu Ser Leu Ala Thr Val
 45                  50                  55                  60

ACA GGC AAC CTG CTG GTA CTC ATC TCT TTC AAG GTC AAC ACG GAG CTC     603
Thr Gly Asn Leu Leu Val Leu Ile Ser Phe Lys Val Asn Thr Glu Leu
             65                  70                  75

AAG ACA GTC AAT AAC TAC TTC CTG CTG AGC CTG GCC TGT GCT GAC CTC     651
Lys Thr Val Asn Asn Tyr Phe Leu Leu Ser Leu Ala Cys Ala Asp Leu
         80                  85                  90

ATC ATC GGT ACC TTC TCC ATG AAC CTC TAT ACC ACG TAC CTG CTC ATG     699
Ile Ile Gly Thr Phe Ser Met Asn Leu Tyr Thr Thr Tyr Leu Leu Met
     95                 100                 105
```

```
GGC CAC TGG GCT CTG GGC ACG CTG GCT TGT GAC CTC TGG CTG GCC CTG     747
Gly His Trp Ala Leu Gly Thr Leu Ala Cys Asp Leu Trp Leu Ala Leu
        110                 115                 120

GAC TAT GTG GCC AGC AAT GCC TCC GTC ATG AAT CTG CTG CTC ATC AGC     795
Asp Tyr Val Ala Ser Asn Ala Ser Val Met Asn Leu Leu Leu Ile Ser
125                 130                 135                 140

TTT GAC CGC TAC TTC TCC GTG ACT CGG CCC CTG AGC TAC CGT GCC AAG     843
Phe Asp Arg Tyr Phe Ser Val Thr Arg Pro Leu Ser Tyr Arg Ala Lys
                145                 150                 155

CGC ACA CCC CGC CGC GCA GCT CTG ATG ATC GGC CTG GCC TGG CTG GTT     891
Arg Thr Pro Arg Arg Ala Ala Leu Met Ile Gly Leu Ala Trp Leu Val
            160                 165                 170

TCC TTT GTG CTC TGG GCC CCA GCC ATC CTC TTC TGG CAA TAC CTG GTA     939
Ser Phe Val Leu Trp Ala Pro Ala Ile Leu Phe Trp Gln Tyr Leu Val
        175                 180                 185

GGG GAG CGG ACG ATG CTA GCT GGG CAG TGC TAC ATC CAG TTC CTC TCC     987
Gly Glu Arg Thr Met Leu Ala Gly Gln Cys Tyr Ile Gln Phe Leu Ser
    190                 195                 200

CAG CCC ATC ATC ACC TTT GGC ACA GCC ATG GCT GCC TTC TAC CTC CCT    1035
Gln Pro Ile Ile Thr Phe Gly Thr Ala Met Ala Ala Phe Tyr Leu Pro
205                 210                 215                 220

GTC ACA GTC ATG TGC ACG CTC TAC TGG CGC ATC TAC CGG GAG ACA GAG    1083
Val Thr Val Met Cys Thr Leu Tyr Trp Arg Ile Tyr Arg Glu Thr Glu
                225                 230                 235

AAC CGA GCA CGG GAG CTG GCA GCC CTT CAG GGC TCC GAG ACG CCA GGC    1131
Asn Arg Ala Arg Glu Leu Ala Ala Leu Gln Gly Ser Glu Thr Pro Gly
                240                 245                 250

AAA AAG GAG AAG AAG GCG GCT CGG ACC CTG AGT GCC ATC CTC CTG GCC    1179
Lys Lys Glu Lys Lys Ala Ala Arg Thr Leu Ser Ala Ile Leu Leu Ala
            255                 260                 265

TTC ATC CTC ACC TGG ACA CCG TAC AAC ATC ATG GTG CTG GTG TCC ACC    1227
Phe Ile Leu Thr Trp Thr Pro Tyr Asn Ile Met Val Leu Val Ser Thr
        270                 275                 280

TTC TGC AAG GAC TGT GTT CCC GAG ACC CTG TGG GAG CTG GGC TAC TGG    1275
Phe Cys Lys Asp Cys Val Pro Glu Thr Leu Trp Glu Leu Gly Tyr Trp
285                 290                 295                 300

CTG TGC TAC GTC AAC AGC ACC ATC AAC CCC ATG TGC TAC GCA CTC TGC    1323
Leu Cys Tyr Val Asn Ser Thr Ile Asn Pro Met Cys Tyr Ala Leu Cys
                305                 310                 315

AAC AAA GCC TTC CGG GAC ACC TTT CGC CTG CTG CTT TGC CGC TGG GAC    1371
Asn Lys Ala Phe Arg Asp Thr Phe Arg Leu Leu Leu Cys Arg Trp Asp
                320                 325                 330

AAG AGA CGC TGG CGC AAG ATC CCC AAG CGC CCT GGC TCC GTG CAC CGC    1419
Lys Arg Arg Trp Arg Lys Ile Pro Lys Arg Pro Gly Ser Val His Arg
            335                 340                 345

ACT CCC TCC CGC CAA TGC TGATAGTCCC CTCTCCTGCA TCCCTCCACC           1467
Thr Pro Ser Arg Gln Cys
        350

CCAGCGGCCG CGACCAGCGA TTGATCGCAC ACGCAGGACA GCCCCACAAC CGGCGCGGCT  1527

GTGTTCAACG ACACACGATG AGTCCCCCAC TCGGTCTTGT ACTCGGATCC TTTT        1581

(2) INFORMATION FOR SEQ ID NO:9:

(i) SEQUENCE CHARACTERISTICS:
        (A) LENGTH: 354 amino acids
        (B) TYPE: amino acid
        (D) TOPOLOGY: linear (ii) MOLECULE TYPE: protein (xi) SEQUENCE DESCRIPTION: SEQ ID NO:9:
```

Met Leu Glu Leu Leu Pro Thr Ala Val Glu Gly Val Ser Gln Ala Gln
 1               5                  10                  15

Ile Gln Ala Leu Met Asn Thr Ser Ala Pro Pro Ala Val Ser Pro Asn
                 20                  25                  30

Ile Thr Val Leu Ala Pro Gly Lys Gly Pro Trp Gln Val Ala Phe Ile
             35                  40                  45

Gly Ile Thr Thr Gly Leu Leu Ser Leu Ala Thr Val Thr Gly Asn Leu
         50                  55                  60

Leu Val Leu Ile Ser Phe Lys Val Asn Thr Glu Leu Lys Thr Val Asn
 65                  70                  75                  80

Asn Tyr Phe Leu Leu Ser Leu Ala Cys Ala Asp Leu Ile Ile Gly Thr
                 85                  90                  95

Phe Ser Met Asn Leu Tyr Thr Thr Tyr Leu Leu Met Gly His Trp Ala
            100                 105                 110

Leu Gly Thr Leu Ala Cys Asp Leu Trp Leu Ala Leu Asp Tyr Val Ala
            115                 120                 125

Ser Asn Ala Ser Val Met Asn Leu Leu Leu Ile Ser Phe Asp Arg Tyr
130                 135                 140

Phe Ser Val Thr Arg Pro Leu Ser Tyr Arg Ala Lys Arg Thr Pro Arg
145                 150                 155                 160

Arg Ala Ala Leu Met Ile Gly Leu Ala Trp Leu Val Ser Phe Val Leu
                165                 170                 175

Trp Ala Pro Ala Ile Leu Phe Trp Gln Tyr Leu Val Gly Glu Arg Thr
            180                 185                 190

Met Leu Ala Gly Gln Cys Tyr Ile Gln Phe Leu Ser Gln Pro Ile Ile
            195                 200                 205

Thr Phe Gly Thr Ala Met Ala Ala Phe Tyr Leu Pro Val Thr Val Met
210                 215                 220

Cys Thr Leu Tyr Trp Arg Ile Tyr Arg Glu Thr Glu Asn Arg Ala Arg
225                 230                 235                 240

Glu Leu Ala Ala Leu Gln Gly Ser Glu Thr Pro Gly Lys Lys Glu Lys
                245                 250                 255

Lys Ala Ala Arg Thr Leu Ser Ala Ile Leu Leu Ala Phe Ile Leu Thr
            260                 265                 270

Trp Thr Pro Tyr Asn Ile Met Val Leu Val Ser Thr Phe Cys Lys Asp
            275                 280                 285

Cys Val Pro Glu Thr Leu Trp Glu Leu Gly Tyr Trp Leu Cys Tyr Val
            290                 295                 300

Asn Ser Thr Ile Asn Pro Met Cys Tyr Ala Leu Cys Asn Lys Ala Phe
305                 310                 315                 320

Arg Asp Thr Phe Arg Leu Leu Leu Cys Arg Trp Asp Lys Arg Arg Trp
                325                 330                 335

Arg Lys Ile Pro Lys Arg Pro Gly Ser Val His Arg Thr Pro Ser Arg
            340                 345                 350

Gln Cys (2) INFORMATION FOR SEQ ID NO:10:

(i) SEQUENCE CHARACTERISTICS:
     (A) LENGTH: 1848 base pairs
     (B) TYPE: nucleic acid
     (C) STRANDEDNESS: single
     (D) TOPOLOGY: linear (ii) MOLECULE TYPE: cDNA (ix) FEATURE:
      (A) NAME/KEY: misc_feature
      (B) LOCATION: 376..414
      (D) OTHER INFORMATION: /note= "Bacteriorhodopsin
           pre-sequence."

(ix) FEATURE:
      (A) NAME/KEY: terminator
      (B) LOCATION: 1756..1758
      (D) OTHER INFORMATION: /note= "Bacteriorhodopsin stop
           codon."

(ix) FEATURE:
      (A) NAME/KEY: misc_feature
      (B) LOCATION: 517..591
      (D) OTHER INFORMATION: /note= "Helix I of rat serotonin
           receptor protein (Type 1C)."

(ix) FEATURE:
      (A) NAME/KEY: misc_feature
      (B) LOCATION: 625..690
      (D) OTHER INFORMATION: /note= "Helix II of rat serotonin
           receptor protein (Type 1C)."

(ix) FEATURE:
      (A) NAME/KEY: misc_feature
      (B) LOCATION: 736..807
      (D) OTHER INFORMATION: /note= "Helix III of rat serotonin
           receptor protein (Type 1C)."

(ix) FEATURE:
      (A) NAME/KEY: misc_feature
      (B) LOCATION: 868..939
      (D) OTHER INFORMATION: /note= "Helix IV of rat serotonin
           receptor protein (Type 1C)."

(ix) FEATURE:
      (A) NAME/KEY: misc_feature
      (B) LOCATION: 997..1059
      (D) OTHER INFORMATION: /note= "Helix V of rat serotonin
           receptor protein (Type 1C)."

(ix) FEATURE:
      (A) NAME/KEY: misc_feature
      (B) LOCATION: 1297..1362
      (D) OTHER INFORMATION: /note= "Helix VI of rat serotonin
           receptor protein (Type 1C)."

(ix) FEATURE:
      (A) NAME/KEY: misc_feature
      (B) LOCATION: 1411..1476
      (D) OTHER INFORMATION: /note= "Helix VII of rat serotonin
           receptor protein (Type 1C)."

(ix) FEATURE:
      (A) NAME/KEY: mutation
      (B) LOCATION: replace(213, "")
      (D) OTHER INFORMATION: /note= "G to A mutation removes
           AlwNI restriction site."

(ix) FEATURE:
      (A) NAME/KEY: misc_feature
      (B) LOCATION: 1732..1734
      (D) OTHER INFORMATION: /note= "Codon encoding the
           C-terminal amino acid of the rat serotonin
           receptor protein (Type 1C)."

(ix) FEATURE:
      (A) NAME/KEY: misc_signal
      (B) LOCATION: 374
      (D) OTHER INFORMATION: /note= "RNA start site."

(ix) FEATURE:
      (A) NAME/KEY: CDS
      (B) LOCATION: 376..1734

(ix) FEATURE:
      (A) NAME/KEY: terminator
      (B) LOCATION: 1735..1737
      (D) OTHER INFORMATION: /note= "Serotonin stop codon."

-continued (ix) FEATURE:
    (A) NAME/KEY: repeat_region
    (B) LOCATION: 436..462
    (D) OTHER INFORMATION: /note= "Sequence encoding
        polyaspartic acid."

(ix) FEATURE:
    (A) NAME/KEY: mutation
    (B) LOCATION: replace(1755, "")
    (D) OTHER INFORMATION: /note= "C to T mutation removes
        AlwNI restriction site."

(xi) SEQUENCE DESCRIPTION: SEQ ID NO:10:

```
ATCTGCAGGA TGGGTGCAAC CGTGAAGTCC GTCACGGCTG CGTCACGACA GGAGCCGACC      60

AGCGACACCC AGAAGGTGCG AACGGTTGAG TGCCGCAACG ATCACGAGTT TTTCGTGCGC     120

TTCGAGTGGT AACACGCGTG CACGCATCGA CTTCACCGCG GGTGTTTCGA CGCCAGCCGG     180

CCGTTGAACC AGCAGGCAGC GGGCATTTCA CATCCGCTGT GGCCCACACA CTCGGTGGGG     240

TGCGCTATTT TGGTATGGTT TGGAATCCGC GTGTCGGCTC CGTGTCTGAC GGTTCATCGG     300

TCTAAATTCC GTCACGAGCG TACCATACTG ATTGGGTCGT AGAGTTACAC ACATATCCTC     360

GTTAGGTACT GTTGC ATG TTG GAG TTA TTG CCA ACA GCA GTG GAG GGG GTA     411
               Met Leu Glu Leu Leu Pro Thr Ala Val Glu Gly Val
                 1               5                  10

TCG CAG GCC CAG ATC CAG GCG CTG GAC TAC AAG GAC GAT GAT GAC GTC      459
Ser Gln Ala Gln Ile Gln Ala Leu Asp Tyr Lys Asp Asp Asp Asp Val
         15                  20                  25

GAC ACT TTT AAT TCC TCC GAT GGT GGA CGC TTG TTT CAA TTC CCG GAC      507
Asp Thr Phe Asn Ser Ser Asp Gly Gly Arg Leu Phe Gln Phe Pro Asp
 30                  35                  40

GGG GTA CAA AAC TGG CCA GCA CTT TCA ATC GTC GTG ATT ATA ATC ATG      555
Gly Val Gln Asn Trp Pro Ala Leu Ser Ile Val Val Ile Ile Ile Met
 45                  50                  55                  60

ACA ATA GGG GGC AAC ATT CTT GTT ATC ATG GCA GTA AGC ATG GAG AAG      603
Thr Ile Gly Gly Asn Ile Leu Val Ile Met Ala Val Ser Met Glu Lys
             65                  70                  75

AAA CTG CAC AAT GCA ACC AAT TAC TTC TTA ATG TCC CTA GCC ATT GCT      651
Lys Leu His Asn Ala Thr Asn Tyr Phe Leu Met Ser Leu Ala Ile Ala
             80                  85                  90

GAT ATG CTG GTG GGA CTA CTT GTC ATG CCC CTG TCC CTG CTT GCT ATT      699
Asp Met Leu Val Gly Leu Leu Val Met Pro Leu Ser Leu Leu Ala Ile
     95                 100                 105

CTT TAT GAT TAT GTC TGG CCT TTA CCT AGA TAT TTG TGC CCC GTC TGG      747
Leu Tyr Asp Tyr Val Trp Pro Leu Pro Arg Tyr Leu Cys Pro Val Trp
110                 115                 120

ATT TCA CTA GAT GTG CTA TTT TCA ACT GCG TCC ATC ATG CAC CTC TGC      795
Ile Ser Leu Asp Val Leu Phe Ser Thr Ala Ser Ile Met His Leu Cys
125                 130                 135                 140

GCC ATA TCG CTG GAC CGG TAT GTA GCA ATA CGT AAT CCT ATT GAG CAT      843
Ala Ile Ser Leu Asp Arg Tyr Val Ala Ile Arg Asn Pro Ile Glu His
                145                 150                 155

AGC CGG TTC AAT TCG CGG ACT AAG GCC ATC ATG AAG ATT GCC ATC GTT      891
Ser Arg Phe Asn Ser Arg Thr Lys Ala Ile Met Lys Ile Ala Ile Val
            160                 165                 170

TGG GCA ATA TCA ATA GGA GTT TCA GTT CCT ATC CCT GTG ATT GGA CTG      939
Trp Ala Ile Ser Ile Gly Val Ser Val Pro Ile Pro Val Ile Gly Leu
        175                 180                 185

AGG GAC GAA AGC AAA GTG TTC GTG AAT AAC ACC ACG TGC GTG CTC AAT      987
Arg Asp Glu Ser Lys Val Phe Val Asn Asn Thr Thr Cys Val Leu Asn
        190                 195                 200

GAC CCC AAC TTC GTT CTC ATC GGG TCC TTC GTG GCA TTC TTC ATC CCG     1035
```

```
Asp Pro Asn Phe Val Leu Ile Gly Ser Phe Val Ala Phe Phe Ile Pro
205                 210                 215                 220

TTG ACG ATT ATG GTG ATC ACC TAC TTC TTA ACG ATC TAC GTC CTG CGC    1083
Leu Thr Ile Met Val Ile Thr Tyr Phe Leu Thr Ile Tyr Val Leu Arg
                    225                 230                 235

CGT CAA ACT CTG ATG TTA CTT CGA GGT CAC ACC GAG GAG GAA CTG GCT    1131
Arg Gln Thr Leu Met Leu Leu Arg Gly His Thr Glu Glu Glu Leu Ala
                240                 245                 250

AAT ATG AGC CTG AAC TTT CTG AAC TGC TGC TGC AAG AAG AAT GGT GGT    1179
Asn Met Ser Leu Asn Phe Leu Asn Cys Cys Cys Lys Lys Asn Gly Gly
                255                 260                 265

GAG GAA GAG AAC GCT CCG AAC CCT AAT CCA GAT CAG AAA CCA CGT CGA    1227
Glu Glu Glu Asn Ala Pro Asn Pro Asn Pro Asp Gln Lys Pro Arg Arg
270                 275                 280

AAG AAG AAA GAA AAG CGT CCC AGA GGC ACC ATG CAA GCT ATC AAC AAC    1275
Lys Lys Lys Glu Lys Arg Pro Arg Gly Thr Met Gln Ala Ile Asn Asn
285                 290                 295                 300

GAA AAG AAA GCT TCC AAA GTC CTT GGC ATT GTA TTC TTT GTG TTT CTG    1323
Glu Lys Lys Ala Ser Lys Val Leu Gly Ile Val Phe Phe Val Phe Leu
                    305                 310                 315

ATC ATG TGG TGC CCG TTT TTC ATC ACC AAT ATC CTG TCG GTT CTT TGT    1371
Ile Met Trp Cys Pro Phe Phe Ile Thr Asn Ile Leu Ser Val Leu Cys
                320                 325                 330

GGG AAG GCC TGT AAC CAA AAG CTA ATG GAG AAG CTT CTC AAT GTG TTT    1419
Gly Lys Ala Cys Asn Gln Lys Leu Met Glu Lys Leu Leu Asn Val Phe
            335                 340                 345

GTG TGG ATT GGC TAT GTG TGT TCA GGC ATC AAT CCT CTG GTG TAC ACT    1467
Val Trp Ile Gly Tyr Val Cys Ser Gly Ile Asn Pro Leu Val Tyr Thr
        350                 355                 360

CTC TTT AAT AAA ATT TAC CGA AGG GCT TTC TCT AAA TAT TTG CGC TGC    1515
Leu Phe Asn Lys Ile Tyr Arg Arg Ala Phe Ser Lys Tyr Leu Arg Cys
365                 370                 375                 380

GAT TAT AAG CCA GAC AAA AAG CCT CCT GTT CGA CAG ATT CCT AGG GTT    1563
Asp Tyr Lys Pro Asp Lys Lys Pro Pro Val Arg Gln Ile Pro Arg Val
                385                 390                 395

GCT GCC ACT GCT TTG TCT GGG AGG GAG CTC AAT GTT AAC ATT TAT CGG    1611
Ala Ala Thr Ala Leu Ser Gly Arg Glu Leu Asn Val Asn Ile Tyr Arg
                400                 405                 410

CAT ACC AAT GAA CGT GTG GCT AGG AAA GCT AAT GAC CCT GAG CCT GGC    1659
His Thr Asn Glu Arg Val Ala Arg Lys Ala Asn Asp Pro Glu Pro Gly
            415                 420                 425

ATA GAG ATG CAG GTG GAG AAC TTA GAG CTG CCA GTC AAC CCC TCT AAT    1707
Ile Glu Met Gln Val Glu Asn Leu Glu Leu Pro Val Asn Pro Ser Asn
        430                 435                 440

GTG GTC AGC GAG AGG ATT AGT AGT GTG TGAGCGGCCG CGACCAGCGA          1754
Val Val Ser Glu Arg Ile Ser Ser Val
445                 450

TTGATCGCAC ACGCAGGACA GCCCCACAAC CGGCGCGGCT GTGTTCAACG ACACACGATG  1814

AGTCCCCCAC TCGGTCTTGT ACTCGGATCC TTTT                              1848

(2) INFORMATION FOR SEQ ID NO:11:

(i) SEQUENCE CHARACTERISTICS:
        (A) LENGTH: 453 amino acids
        (B) TYPE: amino acid
        (D) TOPOLOGY: linear (ii) MOLECULE TYPE: protein (xi) SEQUENCE DESCRIPTION: SEQ ID NO:11:

Met Leu Glu Leu Leu Pro Thr Ala Val Glu Gly Val Ser Gln Ala Gln
```

```
                1               5                  10                 15
        Ile Gln Ala Leu Asp Tyr Lys Asp Asp Asp Val Asp Thr Phe Asn
                         20                 25                 30

Ser Ser Asp Gly Gly Arg Leu Phe Gln Phe Pro Asp Gly Val Gln Asn
                     35                 40                 45

Trp Pro Ala Leu Ser Ile Val Val Ile Ile Met Thr Ile Gly Gly
                 50                 55                 60

Asn Ile Leu Val Ile Met Ala Val Ser Met Glu Lys Lys Leu His Asn
         65                 70                 75                 80

Ala Thr Asn Tyr Phe Leu Met Ser Leu Ala Ile Ala Asp Met Leu Val
                         85                 90                 95

Gly Leu Leu Val Met Pro Leu Ser Leu Leu Ala Ile Leu Tyr Asp Tyr
                     100                105                110

Val Trp Pro Leu Pro Arg Tyr Leu Cys Pro Val Trp Ile Ser Leu Asp
                 115                120                125

Val Leu Phe Ser Thr Ala Ser Ile Met His Leu Cys Ala Ile Ser Leu
         130                135                140

Asp Arg Tyr Val Ala Ile Arg Asn Pro Ile Glu His Ser Arg Phe Asn
        145                150                155                160

Ser Arg Thr Lys Ala Ile Met Lys Ile Ala Ile Val Trp Ala Ile Ser
                     165                170                175

Ile Gly Val Ser Val Pro Ile Pro Val Ile Gly Leu Arg Asp Glu Ser
                     180                185                190

Lys Val Phe Val Asn Asn Thr Thr Cys Val Leu Asn Asp Pro Asn Phe
                     195                200                205

Val Leu Ile Gly Ser Phe Val Ala Phe Phe Ile Pro Leu Thr Ile Met
                     210                215                220

Val Ile Thr Tyr Phe Leu Thr Ile Tyr Val Leu Arg Arg Gln Thr Leu
        225                230                235                240

Met Leu Leu Arg Gly His Thr Glu Glu Leu Ala Asn Met Ser Leu
                         245                250                255

Asn Phe Leu Asn Cys Cys Cys Lys Lys Asn Gly Gly Glu Glu Glu Asn
                         260                265                270

Ala Pro Asn Pro Asn Pro Asp Gln Lys Pro Arg Arg Lys Lys Lys Glu
                     275                280                285

Lys Arg Pro Arg Gly Thr Met Gln Ala Ile Asn Asn Glu Lys Lys Ala
                     290                295                300

Ser Lys Val Leu Gly Ile Val Phe Phe Val Phe Leu Ile Met Trp Cys
        305                310                315                320

Pro Phe Phe Ile Thr Asn Ile Leu Ser Val Leu Cys Gly Lys Ala Cys
                         325                330                335

Asn Gln Lys Leu Met Glu Lys Leu Leu Asn Val Phe Val Trp Ile Gly
                     340                345                350

Tyr Val Cys Ser Gly Ile Asn Pro Leu Val Tyr Thr Leu Phe Asn Lys
                     355                360                365

Ile Tyr Arg Arg Ala Phe Ser Lys Tyr Leu Arg Cys Asp Tyr Lys Pro
                     370                375                380

Asp Lys Lys Pro Pro Val Arg Gln Ile Pro Arg Val Ala Ala Thr Ala
        385                390                395                400

Leu Ser Gly Arg Glu Leu Asn Val Asn Ile Tyr Arg His Thr Asn Glu
                         405                410                415

Arg Val Ala Arg Lys Ala Asn Asp Pro Glu Pro Gly Ile Glu Met Gln
                     420                425                430
```

```
Val Glu Asn Leu Glu Leu Pro Val Asn Pro Ser Asn Val Val Ser Glu
        435                 440                 445

Arg Ile Ser Ser Val
    450

(2) INFORMATION FOR SEQ ID NO:12:

(i) SEQUENCE CHARACTERISTICS:
        (A) LENGTH: 1764 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: repeat_region
        (B) LOCATION: 436..462
        (D) OTHER INFORMATION: /note= "Sequence encoding
            polyaspartic acid."

(ix) FEATURE:
        (A) NAME/KEY: misc_feature
        (B) LOCATION: 463..465
        (D) OTHER INFORMATION: /note= "Codon encoding the
            N-terminal amino acid of the human thrombin
            receptor protein."

(ix) FEATURE:
        (A) NAME/KEY: misc_feature
        (B) LOCATION: 1630..1632
        (D) OTHER INFORMATION: /note= "Codon encoding the
            C-terminal amino acid of the human thrombin
            receptor protein. "

(ix) FEATURE:
        (A) NAME/KEY: repeat_region
        (B) LOCATION: 1633..1650
        (D) OTHER INFORMATION: /note= "Sequence encoding
            polyhistidine."

(ix) FEATURE:
        (A) NAME/KEY: misc_feature
        (B) LOCATION: 648..656
        (D) OTHER INFORMATION: /note= "Deleted AlwNI restriction
            site."

(ix) FEATURE:
        (A) NAME/KEY: misc_feature
        (B) LOCATION: 893..898
        (D) OTHER INFORMATION: /note= "Deleted PstI restriction
            site."

(ix) FEATURE:
        (A) NAME/KEY: misc_feature
        (B) LOCATION: 1301..1309
        (D) OTHER INFORMATION: /note= "Deleted AlwNI restriction
            site."

(ix) FEATURE:
        (A) NAME/KEY: misc_feature
        (B) LOCATION: 1394..1402
        (D) OTHER INFORMATION: /note= "Deleted AlwNI restriction
            site."

(ix) FEATURE:
        (A) NAME/KEY: misc_signal
        (B) LOCATION: 374
        (D) OTHER INFORMATION: /note= "RNA start site."

(ix) FEATURE:
        (A) NAME/KEY: mutation
        (B) LOCATION: replace(1671, "")
        (D) OTHER INFORMATION: /note= "C to T mutation removes
            AlwNI site."

(ix) FEATURE:
        (A) NAME/KEY: CDS
```

-continued

```
         (B) LOCATION: 376..1650

(ix) FEATURE:
         (A) NAME/KEY: misc_feature
         (B) LOCATION: 376..414
         (D) OTHER INFORMATION: /note= "Bacteriorhodopsin
             pre-sequence."

(ix) FEATURE:
         (A) NAME/KEY: terminator
         (B) LOCATION: 1672..1674
         (D) OTHER INFORMATION: /note= "Bacteriorhodopsin stop
             codon."

(ix) FEATURE:
         (A) NAME/KEY: terminator
         (B) LOCATION: 1651..1653
         (D) OTHER INFORMATION: /note= "Thrombin stop codon."

(xi) SEQUENCE DESCRIPTION: SEQ ID NO:12:

ATCTGCAGGA TGGGTGCAAC CGTGAAGTCC GTCACGGCTG CGTCACGACA GGAGCCGACC        60

AGCGACACCC AGAAGGTGCG AACGGTTGAG TGCCGCAACG ATCACGAGTT TTTCGTGCGC       120

TTCGAGTGGT AACACGCGTG CACGCATCGA CTTCACCGCG GGTGTTTCGA CGCCAGCCGG       180

CCGTTGAACC AGCAGGCAGC GGGCATTTCA CATCCGCTGT GGCCCACACA CTCGGTGGGG       240

TGCGCTATTT TGGTATGGTT TGGAATCCGC GTGTCGGCTC CGTGTCTGAC GGTTCATCGG       300

TCTAAATTCC GTCACGAGCG TACCATACTG ATTGGGTCGT AGAGTTACAC ACATATCCTC       360

GTTAGGTACT GTTGC ATG TTG GAG TTA TTG CCA ACA GCA GTG GAG GGG GTA       411
                Met Leu Glu Leu Leu Pro Thr Ala Val Glu Gly Val
                  1               5                  10

TCG CAG GCC CAG ATC CAG GCG CTG GAC TAC AAG GAC GAT GAT GAC GTC        459
Ser Gln Ala Gln Ile Gln Ala Leu Asp Tyr Lys Asp Asp Asp Asp Val
            15                  20                  25

GAC GCC ACC TTA GAT CCC CGG TCA TTT CTT CTC AGG AAC CCC AAT GAT        507
Asp Ala Thr Leu Asp Pro Arg Ser Phe Leu Leu Arg Asn Pro Asn Asp
        30                  35                  40

AAA TAT GAA CCA TTT TGG GAG GAT GAG GAG AAA AAT GAA AGT GGG TTA        555
Lys Tyr Glu Pro Phe Trp Glu Asp Glu Glu Lys Asn Glu Ser Gly Leu
 45                  50                  55                  60

ACT GAA TAC AGA TTA GTC TCC ATC AAT AAA AGC AGT CCT CTT CAA AAA        603
Thr Glu Tyr Arg Leu Val Ser Ile Asn Lys Ser Ser Pro Leu Gln Lys
                65                  70                  75

CAA CTT CCT GCA TTC ATC TCA GAA GAT GCC TCC GGA TAT TTG ACC AGC        651
Gln Leu Pro Ala Phe Ile Ser Glu Asp Ala Ser Gly Tyr Leu Thr Ser
            80                  85                  90

TCC TGG CTG ACA CTC TTT GTC CCA TCT GTG TAC ACC GGA GTG TTT GTA        699
Ser Trp Leu Thr Leu Phe Val Pro Ser Val Tyr Thr Gly Val Phe Val
        95                 100                 105

GTC AGC CTC CCA CTA AAC ATC ATG GCC ATC GTT GTG TTC ATC CTG AAA        747
Val Ser Leu Pro Leu Asn Ile Met Ala Ile Val Val Phe Ile Leu Lys
    110                 115                 120

ATG AAG GTC AAG AAG CCG GCG GTG GTG TAC ATG CTG CAC CTG GCC ACG        795
Met Lys Val Lys Lys Pro Ala Val Val Tyr Met Leu His Leu Ala Thr
125                 130                 135                 140

GCA GAT GTG CTG TTT GTG TCT GTG CTC CCC TTT AAG ATC AGC TAT TAC        843
Ala Asp Val Leu Phe Val Ser Val Leu Pro Phe Lys Ile Ser Tyr Tyr
                145                 150                 155

TTT TCC GGC AGT GAT TGG CAG TTT GGG TCT GAA TTG TGT CGC TTC GTC        891
Phe Ser Gly Ser Asp Trp Gln Phe Gly Ser Glu Leu Cys Arg Phe Val
            160                 165                 170

ACT GCA GCA TTT TAC TGT AAC ATG TAC GCC TCT ATC TTG CTC ATG ACA        939
Thr Ala Ala Phe Tyr Cys Asn Met Tyr Ala Ser Ile Leu Leu Met Thr
        175                 180                 185
```

```
GTC ATA AGC ATT GAC CGG TTT CTG GCT GTG GTG TAT CCC ATG CAG TCC        987
Val Ile Ser Ile Asp Arg Phe Leu Ala Val Val Tyr Pro Met Gln Ser
    190                 195                 200

CTC TCC TGG CGT ACT CTG GGA AGG GCT TCC TTC ACT TGT CTG GCC ATC       1035
Leu Ser Trp Arg Thr Leu Gly Arg Ala Ser Phe Thr Cys Leu Ala Ile
205                 210                 215                 220

TGG GCT TTG GCC ATC GCA GGG GTA GTG CCT CTC GTC CTC AAG GAG CAA       1083
Trp Ala Leu Ala Ile Ala Gly Val Val Pro Leu Val Leu Lys Glu Gln
                225                 230                 235

ACC ATC CAG GTG CCC GGG CTC AAC ATC ACT ACC TGT CAT GAT GTG CTC       1131
Thr Ile Gln Val Pro Gly Leu Asn Ile Thr Thr Cys His Asp Val Leu
        240                 245                 250

AAT GAA ACC CTG CTC GAA GGC TAC TAT GCC TAC TAC TTC TCA GCC TTC       1179
Asn Glu Thr Leu Leu Glu Gly Tyr Tyr Ala Tyr Tyr Phe Ser Ala Phe
            255                 260                 265

TCT GCT GTC TTC TTT TTT GTG CCG CTG ATC ATT TCC ACG GTC TGT TAT       1227
Ser Ala Val Phe Phe Phe Val Pro Leu Ile Ile Ser Thr Val Cys Tyr
270                 275                 280

GTG TCT ATC ATT CGA TGT CTT AGC TCT TCC GCA GTT GCC AAC CGC AGC       1275
Val Ser Ile Ile Arg Cys Leu Ser Ser Ser Ala Val Ala Asn Arg Ser
285                 290                 295                 300

AAG AAG TCC CGG GCT TTG TTC CTG TCA GCT GCT GTT TTC TGC ATC TTC       1323
Lys Lys Ser Arg Ala Leu Phe Leu Ser Ala Ala Val Phe Cys Ile Phe
                305                 310                 315

ATC ATT TGC TTC GGA CCC ACA AAC GTC CTC CTG ATT GCG CAT TAC TCA       1371
Ile Ile Cys Phe Gly Pro Thr Asn Val Leu Leu Ile Ala His Tyr Ser
        320                 325                 330

TTC CTT TCT CAC ACT TCC ACC ACA GAG GCT GCC TAC TTT GCC TAC CTC       1419
Phe Leu Ser His Thr Ser Thr Thr Glu Ala Ala Tyr Phe Ala Tyr Leu
            335                 340                 345

CTC TGT GTC TGT GTC AGC AGC ATA AGC TCG TGC ATC GAC CCC CTA ATT       1467
Leu Cys Val Cys Val Ser Ser Ile Ser Ser Cys Ile Asp Pro Leu Ile
350                 355                 360

TAC TAT TAC GCT TCC TCT GAG TGC CAG AGG TAC GTC TAC AGT ATC TTA       1515
Tyr Tyr Tyr Ala Ser Ser Glu Cys Gln Arg Tyr Val Tyr Ser Ile Leu
365                 370                 375                 380

TGC TGC AAA GAA AGT TCC GAT CCC AGC AGT TAT AAC AGC AGT GGG CAG       1563
Cys Cys Lys Glu Ser Ser Asp Pro Ser Ser Tyr Asn Ser Ser Gly Gln
                385                 390                 395

TTG ATG GCA AGT AAA ATG GAT ACC TGC TCT AGT AAC CTG AAT AAC AGC       1611
Leu Met Ala Ser Lys Met Asp Thr Cys Ser Ser Asn Leu Asn Asn Ser
        400                 405                 410

ATA TAC AAA AAG CTG TTA ACT CAC CAC CAC CAC CAC CAC TGAGCGGCCG       1660
Ile Tyr Lys Lys Leu Leu Thr His His His His His His
            415                 420                 425

CGACCAGCGA TTGATCGCAC ACGCAGGACA GCCCCACAAC CGGCGCGGCT GTGTTCAACG     1720

ACACACGATG AGTCCCCCAC TCGGTCTTGT ACTCGGATCC TTTT                     1764

(2) INFORMATION FOR SEQ ID NO:13:

(i) SEQUENCE CHARACTERISTICS:
        (A) LENGTH: 425 amino acids
        (B) TYPE: amino acid
        (D) TOPOLOGY: linear (ii) MOLECULE TYPE: protein (xi) SEQUENCE DESCRIPTION: SEQ ID NO:13:

Met Leu Glu Leu Leu Pro Thr Ala Val Glu Gly Val Ser Gln Ala Gln
1               5                   10                  15
```

```
Ile Gln Ala Leu Asp Tyr Lys Asp Asp Asp Val Asp Ala Thr Leu
         20                  25                  30

Asp Pro Arg Ser Phe Leu Leu Arg Asn Pro Asn Asp Lys Tyr Glu Pro
         35                  40                  45

Phe Trp Glu Asp Glu Lys Asn Glu Ser Gly Leu Thr Glu Tyr Arg
 50                  55                  60

Leu Val Ser Ile Asn Lys Ser Ser Pro Leu Gln Lys Gln Leu Pro Ala
 65                  70                  75                  80

Phe Ile Ser Glu Asp Ala Ser Gly Tyr Leu Thr Ser Ser Trp Leu Thr
                 85                  90                  95

Leu Phe Val Pro Ser Val Tyr Thr Gly Val Phe Val Val Ser Leu Pro
                100                 105                 110

Leu Asn Ile Met Ala Ile Val Phe Ile Leu Lys Met Lys Val Lys
                115                 120                 125

Lys Pro Ala Val Val Tyr Met Leu His Leu Ala Thr Ala Asp Val Leu
130                 135                 140

Phe Val Ser Val Leu Pro Phe Lys Ile Ser Tyr Tyr Phe Ser Gly Ser
145                 150                 155                 160

Asp Trp Gln Phe Gly Ser Glu Leu Cys Arg Phe Val Thr Ala Ala Phe
                165                 170                 175

Tyr Cys Asn Met Tyr Ala Ser Ile Leu Leu Met Thr Val Ile Ser Ile
                180                 185                 190

Asp Arg Phe Leu Ala Val Val Tyr Pro Met Gln Ser Leu Ser Trp Arg
                195                 200                 205

Thr Leu Gly Arg Ala Ser Phe Thr Cys Leu Ala Ile Trp Ala Leu Ala
210                 215                 220

Ile Ala Gly Val Val Pro Leu Val Leu Lys Glu Gln Thr Ile Gln Val
225                 230                 235                 240

Pro Gly Leu Asn Ile Thr Thr Cys His Asp Val Leu Asn Glu Thr Leu
                245                 250                 255

Leu Glu Gly Tyr Tyr Ala Tyr Tyr Phe Ser Ala Phe Ser Ala Val Phe
                260                 265                 270

Phe Phe Val Pro Leu Ile Ile Ser Thr Val Cys Tyr Val Ser Ile Ile
                275                 280                 285

Arg Cys Leu Ser Ser Ser Ala Val Ala Asn Arg Ser Lys Lys Ser Arg
290                 295                 300

Ala Leu Phe Leu Ser Ala Ala Val Phe Cys Ile Phe Ile Ile Cys Phe
305                 310                 315                 320

Gly Pro Thr Asn Val Leu Leu Ile Ala His Tyr Ser Phe Leu Ser His
                325                 330                 335

Thr Ser Thr Thr Glu Ala Ala Tyr Phe Ala Tyr Leu Leu Cys Val Cys
                340                 345                 350

Val Ser Ser Ile Ser Ser Cys Ile Asp Pro Leu Ile Tyr Tyr Tyr Ala
                355                 360                 365

Ser Ser Glu Cys Gln Arg Tyr Val Tyr Ser Ile Leu Cys Cys Lys Glu
370                 375                 380

Ser Ser Asp Pro Ser Ser Tyr Asn Ser Ser Gly Gln Leu Met Ala Ser
385                 390                 395                 400

Lys Met Asp Thr Cys Ser Ser Asn Leu Asn Asn Ser Ile Tyr Lys Lys
                405                 410                 415

Leu Leu Thr His His His His His
                420                 425

(2) INFORMATION FOR SEQ ID NO:14:
```

(i) SEQUENCE CHARACTERISTICS:
    (A) LENGTH: 2147 base pairs
    (B) TYPE: nucleic acid
    (C) STRANDEDNESS: single
    (D) TOPOLOGY: linear (ii) MOLECULE TYPE: cDNA (ix) FEATURE:
    (A) NAME/KEY: misc_signal
    (B) LOCATION: 378..380
    (D) OTHER INFORMATION: /note= "Bacteriorhodopsin start
        codon."

(ix) FEATURE:
    (A) NAME/KEY: misc_feature
    (B) LOCATION: 378..416
    (D) OTHER INFORMATION: /note= "Bacteriorhodopsin
        pre-sequence."

(ix) FEATURE:
    (A) NAME/KEY: CDS
    (B) LOCATION: 378..2054

(ix) FEATURE:
    (A) NAME/KEY: misc_feature
    (B) LOCATION: 417..419
    (D) OTHER INFORMATION: /note= "Codon encoding N-terminal
        amino acid of mature bacteriorhodopsin."

(ix) FEATURE:
    (A) NAME/KEY: misc_feature
    (B) LOCATION: 1122..1124
    (D) OTHER INFORMATION: /note= "Codon encoding amino acid
        number 236 of bacteriorhodopsin."

(ix) FEATURE:
    (A) NAME/KEY: misc_feature
    (B) LOCATION: 1137..1139
    (D) OTHER INFORMATION: /note= "Codon encoding amino acid
        number 6 of the catalytic subunit of E. coli
        Aspartate Transcarbamylase."

(ix) FEATURE:
    (A) NAME/KEY: misc_feature
    (B) LOCATION: 1125..1178
    (D) OTHER INFORMATION: /note= "Synthetic DNA fragment."

(ix) FEATURE:
    (A) NAME/KEY: misc_feature
    (B) LOCATION: 1125..1136
    (D) OTHER INFORMATION: /note= "Sequence encoding Factor Xa
        proteolytic site."

(ix) FEATURE:
    (A) NAME/KEY: misc_feature
    (B) LOCATION: 2037..2039
    (D) OTHER INFORMATION: /note= "Codon encoding amino acid
        number 306 of E. coli Aspartate Transcarbamylase."

(ix) FEATURE:
    (A) NAME/KEY: misc_feature
    (B) LOCATION: 2040..2054
    (D) OTHER INFORMATION: /note= "Sequence encoding
        bacteriorhodopsin C-terminal amino acid numbers
        245 through 249. "

(ix) FEATURE:
    (A) NAME/KEY: terminator
    (B) LOCATION: 2055..2057
    (D) OTHER INFORMATION: /note= "Bacteriorhodopsin stop
        codon."

(xi) SEQUENCE DESCRIPTION: SEQ ID NO:14:

TAATCTGCAG GATGGGTGCA ACCGTGAAGT CCGTCACGGC TGCGTCACGA CAGGAGCCGA    60

CCAGCGACAC CCAGAAGGTG CGAACGGTTG AGTGCCGCAA CGATCACGAG TTTTTCGTGC    120

-continued

```
GCTTCGAGTG GTAACACGCG TGCACGCATC GACTTCACCG CGGGTGTTTC GACGCCAGCC       180

GGCCGTTGAA CCAGCAGGCA GCGGGCATTT CACAGCCGCT GTGGCCCACA CACTCGGTGG       240

GGTGCGCTAT TTTGGTATGG TTTGGAATCC GCGTGTCGGC TCCGTGTCTG ACGGTTCATC       300

GGTCTAAATT CCGTCACGAG CGTACCATAC TGATTGGGTC GTAGAGTTAC ACACATATCC       360

TCGTTAGGTA CTGTTGC ATG TTG GAG TTA TTG CCA ACA GCA GTG GAG GGG         410
                    Met Leu Glu Leu Leu Pro Thr Ala Val Glu Gly
                     1               5                      10

GTA TCG CAG GCC CAG ATC ACC GGA CGT CCG GAG TGG ATC TGG CTA GCG         458
Val Ser Gln Ala Gln Ile Thr Gly Arg Pro Glu Trp Ile Trp Leu Ala
             15                  20                  25

CTC GGT ACG GCG CTA ATG GGA CTC GGG ACG CTC TAT TTC CTC GTG AAA         506
Leu Gly Thr Ala Leu Met Gly Leu Gly Thr Leu Tyr Phe Leu Val Lys
         30                  35                  40

GGG ATG GGC GTC TCG GAC CCA GAT GCA AAG AAA TTC TAC GCC ATC ACG         554
Gly Met Gly Val Ser Asp Pro Asp Ala Lys Lys Phe Tyr Ala Ile Thr
     45                  50                  55

ACG CTC GTC CCA GCC ATC GCG TTC ACG ATG TAC CTC TCG ATG CTG CTG         602
Thr Leu Val Pro Ala Ile Ala Phe Thr Met Tyr Leu Ser Met Leu Leu
 60                  65                  70                  75

GGG TAT GGC CTC ACA ATG GTA CCG TTC GGT GGG GAG CAG AAC CCC ATC         650
Gly Tyr Gly Leu Thr Met Val Pro Phe Gly Gly Glu Gln Asn Pro Ile
                 80                  85                  90

TAC TGG GCG CGG TAC GCT GAC TGG CTG TTC ACC ACG CCG CTG TTG TTG         698
Tyr Trp Ala Arg Tyr Ala Asp Trp Leu Phe Thr Thr Pro Leu Leu Leu
             95                  100                 105

TTA GAC CTC GCG TTG CTC GTT GAC GCG GAT CAG GGA ACG ATC CTT GCG         746
Leu Asp Leu Ala Leu Leu Val Asp Ala Asp Gln Gly Thr Ile Leu Ala
         110                 115                 120

CTC GTC GGT GCC GAC GGC ATC ATG ATC GGG ACC GGC CTG GTC GGC GCA         794
Leu Val Gly Ala Asp Gly Ile Met Ile Gly Thr Gly Leu Val Gly Ala
     125                 130                 135

CTG ACG AAG GTC TAC TCG TAC CGC TTC GTG TGG TGG GCA ATC AGC ACC         842
Leu Thr Lys Val Tyr Ser Tyr Arg Phe Val Trp Trp Ala Ile Ser Thr
140                 145                 150                 155

GCA GCG ATG CTG TAC ATC CTG TAC GTG CTG TTC TTC GGG TTC ACC TCG         890
Ala Ala Met Leu Tyr Ile Leu Tyr Val Leu Phe Phe Gly Phe Thr Ser
                 160                 165                 170

AAG GCC GAA AGC ATG CGC CCC GAG GTC GCA TCC ACG TTC AAA GTA CTG         938
Lys Ala Glu Ser Met Arg Pro Glu Val Ala Ser Thr Phe Lys Val Leu
             175                 180                 185

CGT AAC GTT ACC GTT GTG TTG TGG TCC GCG TAT CCC GTC GTG TGG CTG         986
Arg Asn Val Thr Val Val Leu Trp Ser Ala Tyr Pro Val Val Trp Leu
         190                 195                 200

ATC GGC AGC GAA GGT GCG GGA ATC GTG CCG CTG AAC ATC GAG ACG CTG        1034
Ile Gly Ser Glu Gly Ala Gly Ile Val Pro Leu Asn Ile Glu Thr Leu
     205                 210                 215

CTG TTC ATG GTG CTT GAC GTG AGC GCG AAG GTC GGC TTC GGG CTC ATC        1082
Leu Phe Met Val Leu Asp Val Ser Ala Lys Val Gly Phe Gly Leu Ile
220                 225                 230                 235

CTC CTG CGC AGT CGT GCG ATC TTC GGC GAA GCC GAA GCG CCG ATC GAA        1130
Leu Leu Arg Ser Arg Ala Ile Phe Gly Glu Ala Glu Ala Pro Ile Glu
                 240                 245                 250

GGT CGT CAG AAA CAT ATC ATT TCC ATA AAC GAC CTT AGT CGC GAT GAC        1178
Gly Arg Gln Lys His Ile Ile Ser Ile Asn Asp Leu Ser Arg Asp Asp
             255                 260                 265

CTT AAT CTG GTG CTG GCG ACA GCG GCG AAA CTG AAA GCA AAC CCG CAA        1226
Leu Asn Leu Val Leu Ala Thr Ala Ala Lys Leu Lys Ala Asn Pro Gln
         270                 275                 280
```

| | | | | | | | | | | | | | | | |
|---|---|---|---|---|---|---|---|---|---|---|---|---|---|---|---|
|CCA|GAG|CTG|TTG|AAG|CAC|AAA|GTC|ATT|GCC|AGC|TGT|TTC|TTC|GAA|GCC|1274
|Pro|Glu|Leu|Leu|Lys|His|Lys|Val|Ile|Ala|Ser|Cys|Phe|Phe|Glu|Ala|
|285| | | | |290| | | | |295| | | | | |

```
CCA GAG CTG TTG AAG CAC AAA GTC ATT GCC AGC TGT TTC TTC GAA GCC    1274
Pro Glu Leu Leu Lys His Lys Val Ile Ala Ser Cys Phe Phe Glu Ala
285                 290                 295

TCT ACC CGT ACC CGC CTC TCT TTT CAA ACA TCT ATG CAC CGC CTG GGG    1322
Ser Thr Arg Thr Arg Leu Ser Phe Gln Thr Ser Met His Arg Leu Gly
300                 305                 310                 315

GCC AGC GTG GTG GGC TTC TCC GAC AGC GCC AAT ACA TCA CTG GGT AAA    1370
Ala Ser Val Val Gly Phe Ser Asp Ser Ala Asn Thr Ser Leu Gly Lys
                320                 325                 330

AAA GGC GAA ACG CTT GCC GAT ACC ATT TCA GTT ATC AGC ACT TAC GTC    1418
Lys Gly Glu Thr Leu Ala Asp Thr Ile Ser Val Ile Ser Thr Tyr Val
            335                 340                 345

GAT GCG ATA GTG ATG CGT CAT CCG CAG GAA GGT GCG GCG CGC CTG GCC    1466
Asp Ala Ile Val Met Arg His Pro Gln Glu Gly Ala Ala Arg Leu Ala
350                 355                 360

ACC GAG TTT TCC GGC AAT GTA CCG GTA CTG AAT GCC GGT GAT GGC TCC    1514
Thr Glu Phe Ser Gly Asn Val Pro Val Leu Asn Ala Gly Asp Gly Ser
365                 370                 375

AAC CAA CAT CCG ACG CAA ACC TTG CTG GAC TTA TTC ACT ATT CAG GAA    1562
Asn Gln His Pro Thr Gln Thr Leu Leu Asp Leu Phe Thr Ile Gln Glu
380                 385                 390                 395

ACC CAG GGG CGT CTG GAC AAT CTC CAC GTC GCA ATG GTT GGT GAC CTG    1610
Thr Gln Gly Arg Leu Asp Asn Leu His Val Ala Met Val Gly Asp Leu
                400                 405                 410

AAA TAT GGT CGC ACC GTT CAC TCC CTG ACT CAG GCG TTA GCT AAG TTC    1658
Lys Tyr Gly Arg Thr Val His Ser Leu Thr Gln Ala Leu Ala Lys Phe
            415                 420                 425

GAC GGC AAC CGT TTT TAC TTC ATC GCG CCG GAC GCG CTG GCA ATG CCG    1706
Asp Gly Asn Arg Phe Tyr Phe Ile Ala Pro Asp Ala Leu Ala Met Pro
430                 435                 440

CAA TAC ATT CTG GAT ATG CTC GAT GAA AAA GGG ATC GCA TGG AGT CTG    1754
Gln Tyr Ile Leu Asp Met Leu Asp Glu Lys Gly Ile Ala Trp Ser Leu
445                 450                 455

CAC AGC TCT ATT GAA GAA GTG ATG GTG GAA GTA GAC ATC CTG TAC ATG    1802
His Ser Ser Ile Glu Glu Val Met Val Glu Val Asp Ile Leu Tyr Met
460                 465                 470                 475

ACC CGC GTG CAA AAA GAG CGT CTG GAC CCG TCC GAG TAC GCC AAC GTG    1850
Thr Arg Val Gln Lys Glu Arg Leu Asp Pro Ser Glu Tyr Ala Asn Val
                480                 485                 490

AAA GCG CAG TTT GTT CTT CGC GCC AGT GAT CTC CAC AAC GCC AAA GCC    1898
Lys Ala Gln Phe Val Leu Arg Ala Ser Asp Leu His Asn Ala Lys Ala
            495                 500                 505

AAT ATG AAA GTG CTG CAT CCG TTG CCG CGT GTT GAT GAG ATT GCG ACG    1946
Asn Met Lys Val Leu His Pro Leu Pro Arg Val Asp Glu Ile Ala Thr
510                 515                 520

GAT GTT GAT AAA ACG CCA CAC GCC TGG TAC TTC CAG CAG GCA GGC AAC    1994
Asp Val Asp Lys Thr Pro His Ala Trp Tyr Phe Gln Gln Ala Gly Asn
525                 530                 535

GGG ATT TTC GCT CTG CAA GCG TTA CTG GCA CTG GTT CTG AAT CGG GCC    2042
Gly Ile Phe Ala Leu Gln Ala Leu Leu Ala Leu Val Leu Asn Arg Ala
540                 545                 550                 555

GCG ACC AGC GAC TGATCGCACA CGCAGGACAG CCCCACAACC GGCGCGGCTG        2094
Ala Thr Ser Asp

TGTTCAACGA CACACGATGA GTCCCCCACT CGGTCTTGTA CTCGGATCCT TTT          2147
```

(2) INFORMATION FOR SEQ ID NO:15:

(i) SEQUENCE CHARACTERISTICS:
        (A) LENGTH: 559 amino acids
        (B) TYPE: amino acid
        (D) TOPOLOGY: linear (ii) MOLECULE TYPE: protein (xi) SEQUENCE DESCRIPTION: SEQ ID NO:15:

| | | | | | | | | | | | | | | |
|---|---|---|---|---|---|---|---|---|---|---|---|---|---|---|
| Met | Leu | Glu | Leu | Leu | Pro | Thr | Ala | Val | Glu | Gly | Val | Ser | Gln | Ala | Gln |
| 1 | | | | 5 | | | | | 10 | | | | | 15 | |
| Ile | Thr | Gly | Arg | Pro | Glu | Trp | Ile | Trp | Leu | Ala | Leu | Gly | Thr | Ala | Leu |
| | | | 20 | | | | | 25 | | | | | 30 | | |
| Met | Gly | Leu | Gly | Thr | Leu | Tyr | Phe | Leu | Val | Lys | Gly | Met | Gly | Val | Ser |
| | | 35 | | | | | 40 | | | | | 45 | | | |
| Asp | Pro | Asp | Ala | Lys | Lys | Phe | Tyr | Ala | Ile | Thr | Thr | Leu | Val | Pro | Ala |
| | 50 | | | | | 55 | | | | | 60 | | | | |
| Ile | Ala | Phe | Thr | Met | Tyr | Leu | Ser | Met | Leu | Leu | Gly | Tyr | Gly | Leu | Thr |
| 65 | | | | 70 | | | | | 75 | | | | | 80 | |
| Met | Val | Pro | Phe | Gly | Gly | Glu | Gln | Asn | Pro | Ile | Tyr | Trp | Ala | Arg | Tyr |
| | | | | 85 | | | | | 90 | | | | | 95 | |
| Ala | Asp | Trp | Leu | Phe | Thr | Thr | Pro | Leu | Leu | Leu | Leu | Asp | Leu | Ala | Leu |
| | | | 100 | | | | | 105 | | | | | 110 | | |
| Leu | Val | Asp | Ala | Asp | Gln | Gly | Thr | Ile | Leu | Ala | Leu | Val | Gly | Ala | Asp |
| | | 115 | | | | | 120 | | | | | 125 | | | |
| Gly | Ile | Met | Ile | Gly | Thr | Gly | Leu | Val | Gly | Ala | Leu | Thr | Lys | Val | Tyr |
| | 130 | | | | | 135 | | | | | 140 | | | | |
| Ser | Tyr | Arg | Phe | Val | Trp | Trp | Ala | Ile | Ser | Thr | Ala | Ala | Met | Leu | Tyr |
| 145 | | | | 150 | | | | | 155 | | | | | 160 | |
| Ile | Leu | Tyr | Val | Leu | Phe | Phe | Gly | Phe | Thr | Ser | Lys | Ala | Glu | Ser | Met |
| | | | | 165 | | | | | 170 | | | | | 175 | |
| Arg | Pro | Glu | Val | Ala | Ser | Thr | Phe | Lys | Val | Leu | Arg | Asn | Val | Thr | Val |
| | | | 180 | | | | | 185 | | | | | 190 | | |
| Val | Leu | Trp | Ser | Ala | Tyr | Pro | Val | Val | Trp | Leu | Ile | Gly | Ser | Glu | Gly |
| | | 195 | | | | | 200 | | | | | 205 | | | |
| Ala | Gly | Ile | Val | Pro | Leu | Asn | Ile | Glu | Thr | Leu | Leu | Phe | Met | Val | Leu |
| | 210 | | | | | 215 | | | | | 220 | | | | |
| Asp | Val | Ser | Ala | Lys | Val | Gly | Phe | Gly | Leu | Ile | Leu | Leu | Arg | Ser | Arg |
| 225 | | | | 230 | | | | | 235 | | | | | 240 | |
| Ala | Ile | Phe | Gly | Glu | Ala | Glu | Ala | Pro | Ile | Glu | Gly | Arg | Gln | Lys | His |
| | | | | 245 | | | | | 250 | | | | | 255 | |
| Ile | Ile | Ser | Ile | Asn | Asp | Leu | Ser | Arg | Asp | Asp | Leu | Asn | Leu | Val | Leu |
| | | | 260 | | | | | 265 | | | | | 270 | | |
| Ala | Thr | Ala | Ala | Lys | Leu | Lys | Ala | Asn | Pro | Gln | Pro | Glu | Leu | Leu | Lys |
| | | 275 | | | | | 280 | | | | | 285 | | | |
| His | Lys | Val | Ile | Ala | Ser | Cys | Phe | Phe | Glu | Ala | Ser | Thr | Arg | Thr | Arg |
| | 290 | | | | | 295 | | | | | 300 | | | | |
| Leu | Ser | Phe | Gln | Thr | Ser | Met | His | Arg | Leu | Gly | Ala | Ser | Val | Val | Gly |
| 305 | | | | 310 | | | | | 315 | | | | | 320 | |
| Phe | Ser | Asp | Ser | Ala | Asn | Thr | Ser | Leu | Gly | Lys | Lys | Gly | Glu | Thr | Leu |
| | | | | 325 | | | | | 330 | | | | | 335 | |
| Ala | Asp | Thr | Ile | Ser | Val | Ile | Ser | Thr | Tyr | Val | Asp | Ala | Ile | Val | Met |
| | | | 340 | | | | | 345 | | | | | 350 | | |
| Arg | His | Pro | Gln | Glu | Gly | Ala | Ala | Arg | Leu | Ala | Thr | Glu | Phe | Ser | Gly |
| | | 355 | | | | | 360 | | | | | 365 | | | |
| Asn | Val | Pro | Val | Leu | Asn | Ala | Gly | Asp | Gly | Ser | Asn | Gln | His | Pro | Thr |
| | 370 | | | | | 375 | | | | | 380 | | | | |
| Gln | Thr | Leu | Leu | Asp | Leu | Phe | Thr | Ile | Gln | Glu | Thr | Gln | Gly | Arg | Leu |
| 385 | | | | 390 | | | | | 395 | | | | | 400 | |

```
Asp Asn Leu His Val Ala Met Val Gly Asp Leu Lys Tyr Gly Arg Thr
            405             410                 415

Val His Ser Leu Thr Gln Ala Leu Ala Lys Phe Asp Gly Asn Arg Phe
            420             425             430

Tyr Phe Ile Ala Pro Asp Ala Leu Ala Met Pro Gln Tyr Ile Leu Asp
        435             440                 445

Met Leu Asp Glu Lys Gly Ile Ala Trp Ser Leu His Ser Ser Ile Glu
    450             455                 460

Glu Val Met Val Glu Val Asp Ile Leu Tyr Met Thr Arg Val Gln Lys
465             470                 475                 480

Glu Arg Leu Asp Pro Ser Glu Tyr Ala Asn Val Lys Ala Gln Phe Val
            485             490                 495

Leu Arg Ala Ser Asp Leu His Asn Ala Lys Ala Asn Met Lys Val Leu
            500             505                 510

His Pro Leu Pro Arg Val Asp Glu Ile Ala Thr Asp Val Asp Lys Thr
        515             520                 525

Pro His Ala Trp Tyr Phe Gln Gln Ala Gly Asn Gly Ile Phe Ala Leu
    530             535                 540

Gln Ala Leu Leu Ala Leu Val Leu Asn Arg Ala Ala Thr Ser Asp
545             550             555
```